US012749556B2

(12) United States Patent
Nicosia et al.

(10) Patent No.: US 12,749,556 B2
(45) Date of Patent: Sep. 29, 2026

(54) SELECTION OF CANCER MUTATIONS FOR GENERATION OF A PERSONALIZED CANCER VACCINE

(71) Applicant: NOUSCOM AG, Basel (CH)

(72) Inventors: Alfredo Nicosia, Naples (IT); Elisa Scarselli, Rome (IT); Armin Lahm, Rome (IT); Guido Leoni, Rome (IT)

(73) Assignee: NOUSCOM AG, Basel (CH)

( * ) Notice: Subject to any disclaimer, the term of this patent is extended or adjusted under 35 U.S.C. 154(b) by 1177 days.

(21) Appl. No.: 17/282,080

(22) PCT Filed: Nov. 15, 2019

(86) PCT No.: PCT/EP2019/081428

§ 371 (c)(1),
(2) Date: Apr. 1, 2021

(87) PCT Pub. No.: WO2020/099614

PCT Pub. Date: May 22, 2020

(65) Prior Publication Data

US 2021/0379170 A1 Dec. 9, 2021

(30) Foreign Application Priority Data

Nov. 15, 2018 (EP) .................................... 18206599

(51) Int. Cl.

| | |
|---|---|
| ***G16B 20/20*** | (2019.01) |
| ***A61K 39/00*** | (2006.01) |
| ***A61P 35/00*** | (2006.01) |
| ***C07K 14/47*** | (2006.01) |
| ***C12Q 1/6886*** | (2018.01) |
| ***G16B 15/30*** | (2019.01) |

(52) U.S. Cl.

CPC .......... *G16B 20/20* (2019.02); *A61K 39/0011* (2013.01); *A61P 35/00* (2018.01); *C07K 14/4748* (2013.01); *C12Q 1/6886* (2013.01); *G16B 15/30* (2019.02); *A61K 2039/53* (2013.01); *A61K 2039/55516* (2013.01); *C12Q 2600/156* (2013.01); *C12Q 2600/158* (2013.01)

(58) Field of Classification Search

None
See application file for complete search history.

(56) References Cited

U.S. PATENT DOCUMENTS

| | | | |
|---|---|---|---|
| 10,055,540 | B2 * | 8/2018 | Yelensky et al. |
| 11,912,743 | B2 * | 2/2024 | Nicosa et al. |
| 2017/0016075 | A1 | 1/2017 | Velculescu |
| 2018/0318409 | A1 * | 11/2018 | Valiante et al. |
| 2019/0008938 | A1 * | 1/2019 | Ciaramella et al. |

FOREIGN PATENT DOCUMENTS

| | | | |
|---|---|---|---|
| WO | 2016/128376 | A1 | 2/2016 |
| WO | 2017/011660 | A1 | 1/2017 |
| WO | 2017/106638 | | 6/2017 |

OTHER PUBLICATIONS

Bjerregaard, Anne-Mette et al. "MuPeXI: prediction of neo-epitopes from tumor sequencing data." Cancer Immunology, Immunotherapy 66.9 (2017): 1123-1130. Web. (Year: 2017).*

Kreiter, Sebastian et al. "Mutant MHC Class II Epitopes Drive Therapeutic Immune Responses to Cancer." Nature 520.7549 (2015): 692-696. Web. (Year: 2015).*

Wagner, Günter P, Koryu Kin, and Vincent J Lynch. "Measurement of mRNA Abundance Using RNA-Seq Data: RPKM Measure Is Inconsistent among Samples." Theory in biosciences= Theorie in den Biowissenschaften 131.4 (2012): 281-285. Web. (Year: 2012).*

Leoni, Guido et al. "VENUS, a Novel Selection Approach to Improve the Accuracy of Neoantigens' Prediction." Vaccines 9.8 (2021): 880-. Web. (Year: 2021).*

Hundal, Jasreet et al. "pVAC-Seq: A Genome-Guided in Silico Approach to Identifying Tumor Neoantigens." Genome medicine 8.1 (2016): 11-11. Web. (Year: 2016).*

Rubinsteyn, Alex et al. "Computational Pipeline for the PGV-001 Neoantigen Vaccine Trial." Frontiers in immunology 8 (2018): 1807-1807. Web. (Year: 2018).*

Anagnostou, Valsamo et al. "Evolution of Neoantigen Landscape during Immune Checkpoint Blockade in Non-Small Cell Lung Cancer." Cancer discovery 7.3 (2017): 264-276. Web. (Year: 2017).*

MRNA (2016) Analysis Pipeline "https://docs.gdc.cancer.gov/Data/Bioinformatics_Pipelines/Expression_mRNA_Pipeline/# file-access-and-availability" (Year: 2016).*

Scholtalbers, Jelle et al. "TCLP: An Online Cancer Cell Line Catalogue Integrating HLA Type, Predicted Neo-Epitopes, Virus and Gene Expression." Genome medicine 7.120 (2015): 118-118. Web (Year: 2015).*

Jurtz, Vanessa et al. "NetMHCpan-4.0: Improved Peptide-MHC Class I Interaction Predictions Integrating Eluted Ligand and Peptide Binding Affinity Data." The Journal of Immunology 199.9 (2017): 3360-3368. Web. (Year: 2017).*

Rech, et al., "Tumor Immunity and Survival as a Function of Alternative Neopeptides in Human Cancer," Cancer Immunol Res; 6(3) Mar. 2018, pp. 276-287.

(Continued)

*Primary Examiner* — Anna Skibinsky
*Assistant Examiner* — Joseph Pulliam
(74) *Attorney, Agent, or Firm* — McDonnell Boehnen Hulbert & Berghoff LLP

(57) ABSTRACT

The present invention relates to a method for selecting cancer neoantigens for use in a personalized vaccine. This invention relates as well to a method for constructing a vector or collection of vectors carrying the neoantigens for a personalized vaccine. This invention further relates to vector and collection of vectors comprising the personalized genetic vaccine and the use of said vectors in cancer treatment.

10 Claims, 12 Drawing Sheets

Figure 1A:
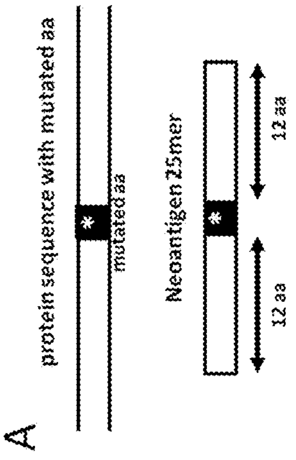

Specification includes a Sequence Listing.

(56) References Cited

OTHER PUBLICATIONS

Office Action in corresponding Korean Patent Application No. 10-2021-7012084, mailed Apr. 22, 2025, English translation.

Sahin U. et al. , Personalized RNA mutanome vaccines mobilize poly-specific therapeutic immunity against cancer. Nature , Jul. 5, 2017, vol. 547, pp. 222-226.

Boyle S.M. et al. , Accurately identifying neoantigens utilizing both DNA and PNA somatic variants in an enhanced platform. Cancer Res, Jul. 1, 2017, vol. 77, No. 13 Supplement, p. 554.

Karasaki, et al., "Prediction and prioritization of neoantigens: integration of RNA sequencing data with whole-exome sequencing," Cancer Sci., Feb. 2017, vol. 108, No. 2, pp. 170-177.

Finn, et al., "Is It Possible to Develop Cancer Vaccines to Neoantigens, What Are the Major Challenges, and How Can These Be Overcome?" Cold Spring Harb Perspect Biol 2018; 10:a028829.

The International Search Report (ISR) with Written Opinion for PCT/EP2019/081428 Apr. 8, 2020, pp. 1-20.

Aurisicchio et al. "The perfect personalized cancer therapy: cancer vaccines against neoantigens" Journal of Experimental and Clinical Cancer Research (2018) vol. 37(1), 10 pages.

Ott et al. "An immunogenic personal neoantigen vaccine for patients with melanoma" Nature (2017) vol. 547 (7662), 22 pages.

Shin et al. "Prevalence and detection of low-allele-fraction variants in clinical cancer samples" Nature Communications (2017) vol. 8(1), pp. 1-10.

* cited by examiner

Figure 3

Rank neoantigens according to mutant allele Frequency

| | RFREQ |
|---|---|
| SNV101 | 1 |
| SNV16 | 2 |
| SNV34 | 3 |
| SNV87 | 4 |
| SNV23 | 5 |
| FSP4_5 | 6 |
| SNV120 | 7 |
| SNV11 | 8 |
| SNV67 | 9 |
| SNV18 | 9 |
| ...... | |

Rank neoantigens according to corrTPM

| | REXPR |
|---|---|
| SNV11 | 1 |
| SNV88 | 2 |
| SNV34 | 3 |
| SNV67 | 4 |
| SNV23 | 5 |
| SNV55 | 6 |
| SNV63 | 7 |
| SNV34 | 8 |
| SNV18 | 9 |
| FSP4_5 | 10 |
| ...... | |

Rank neoantigens according to MHC I binding prediction (IC50)

| | RIC50 |
|---|---|
| SNV67 | 1 |
| SNV11 | 2 |
| SNV23 | 3 |
| SNV61 | 4 |
| SNV26 | 5 |
| SNV105 | 6 |
| SNV69 | 7 |
| SNV18 | 8 |
| SNV34 | 9 |
| FSP4_5 | 10 |
| ...... | |

Rank neoantigens by weighted sum of ranks:

RSUM = (RFREQ + REXPR + (k + RIC50)) * WF

| | RFREQ | REXPR | RIC50 | WF | RSUM | Final Rank |
|---|---|---|---|---|---|---|
| SNV11 | 8 | 1 | 2 | 1 | 11 | 1 |
| SNV23 | 5 | 5 | 3 | 1 | 13 | 2 |
| SNV67 | 9 | 4 | 1 | 1 | 14 | 3 |
| SNV34 | 3 | 8 | 9 | 1 | 20 | 4 |
| SNV18 | 9 | 9 | 8 | 1 | 26 | 5 |
| FSP4_5 | 6 | 10 | 10 | 1 | 26 | 6 |
| ...... | | | | | | |
| SNV38 | 57 | 123 | 89 | 1 | 269 | 132 |

Figure 6

```
Merged FSP example 1:

complete FSP chr11:1758971 (SEQ ID NO: 1)
GSLSGYLSQDTVGALPVSVVSLCPGRCQSGGEAGLWGGHQAARHHLHRSQVRWHPGHGLPPHLRQQRAARLRQPDAAEAGGPEHLLLLPEQGPRCAAWG

GSLSGYLSQDTVGALPVSVVSLCPGRCQSG    merged FSP Pos 23 Final Rank (SEQ ID NO: 2)

GSLSGYLSQDTVGALPVSVVSLC           23 FSP-1_chr11:1758971 (SEQ ID NO: 3)
  LSGYLSQDTVGALPVSVVSLCPGRC       53 FSP-4_chr11:1758971 (SEQ ID NO: 4)
   SGYLSQDTVGALPVSVVSLCPGRCQ      59 FSP-6_chr11:1758971 (SEQ ID NO: 5)
     YLSQDTVGALPVSVVSLCPGRCQSG    52 FSP-3_chr11:1758971 (SEQ ID NO: 6)

                                 (SEQ ID NO: 7)    PGHGLPPHLRQQRAARLRQPDAAEA 54 FSP-5_chr11:1758971

                                 (SEQ ID NO: 8)      29 FSP-2_chr11:1758971   PEHLLLLPEQGPRCAAWG

Merged FSP example 2:

complete FSP chr6:168310205 (SEQ ID NO: 9)
ARPPGSVEDAGQAVGHILAQACVYRAVQCSR    merged FSP Pos 28 Final Rank

ARPPGSVEDAGQAVGHILAQAC           51 FSP-15_chr6:168310205 (SEQ ID NO: 10)
       EDAGQAVGHILAQACVYRAVQCSR 28 FSP-14_chr6:168310205 (SEQ ID NO: 11)
```

SELECTION OF CANCER MUTATIONS FOR GENERATION OF A PERSONALIZED CANCER VACCINE

CROSS REFERENCE TO RELATED APPLICATION

This application is a U.S. national phase of International Application No. PCT/EP2019/081428, filed Nov. 15, 2019, which claims priority to European Patent Application No. 18206599.5, filed Nov. 15, 2018, both of which are incorporated by reference herein in their entirety.

The present invention relates to a method for selecting cancer neoantigens for use in a personalized vaccine. This invention relates as well to a method for constructing a vector or collection of vectors carrying the neoantigens for a personalized vaccine. This invention further relates to vectors and collection of vectors comprising the personalized vaccine and the use of said vectors in cancer treatment.

BACKGROUND OF THE INVENTION

Several tumor antigens have been identified and classified into different categories: cancer-germ-line, tissue differentiation antigens and neoantigens derived from mutated self-proteins (Anderson et al., 2012). Whether the immune responses against self-antigens have an impact on tumor growth is a matter of debate (reviewed in Anderson et al., 2012). In contrast, recent compelling evidences support the notion that neoantigens, generated in the tumor as a consequence of mutations in coding sequences of expressed genes, represent a promising target for vaccination against cancer (Fritsch et al., 2014).

Cancer neoantigens are antigens present exclusively on tumor cells and not on normal cells. Neoantigens are generated by DNA mutations in tumor cells and have been shown to play a significant role in recognition and killing of tumor cells by the T cell mediated immune response, mainly by $CD8^+$ T cells (Yarchoan et al., 2017). The advent of massively parallel sequencing methods commonly referred to as next generation sequencing (NGS), which allows to determine the complete sequence of a cancer genome in a timely and inexpensive manner, unveiled the mutational spectra of human tumors (Kandoth et al., 2013). The most frequent type of mutation is a single nucleotide variant and the median number of single nucleotide variants found in tumors varies considerably according to their histology. Since very few mutations are generally shared among patients, the identification of mutations generating neoantigens requires a personalized approach.

Many mutations are indeed not seen by the immune system because either potential epitopes are not processed/presented by the tumor cells or because immune tolerance led to elimination of T cells reactive with the mutated sequence. Therefore, it is beneficial to select, among all potential neoantigens, those having the highest chance to be immunogenic, to define the optimal number to be encoded by a vaccine and finally a preferred vaccine layout for optimizing immunogenicity. Furthermore not only neoantigens generated by single nucleotide variant mutations but also neoantigens generated by insertions/deletion mutations that generate a frameshift peptide are important, the latter is expected to be particular immunogenic. Recently two different personalized vaccination approaches based either on RNA or on peptides have been evaluated in phase-I clinical studies. The data obtained shows that vaccination indeed can both expand pre-existing neoantigen-specific T cells and induce a broader repertoire of new T-cell specificity in cancer patients (Sahin et al., 2017). The main limitation of both approaches is the maximum number of neoantigens that are targeted by the vaccination. The upper limit for the peptide-based approach, based on their published data, is of twenty peptides and was not reached in all patients because in some cases peptides could not be synthesized. The described upper limit for the RNA-based approach is even lower, since they include only 10 mutations in each vaccine (Sahin et al., 2017).

The challenge for a cancer vaccine in curing cancer is to induce a diverse population of immune T cells capable of recognizing and eliminating as large a number of cancer cells as possible at once, to decrease the chance that cancer cells can "escape" the T cell response and are not being recognized by the immune response. Therefore, it is desirable that the vaccine encodes a large number of cancer specific antigens, i.e. neoantigens. This is particular relevant for a personalized genetic vaccine approach based on cancer specific neoantigens of an individual. In order to optimize the probability of success as many neoantigens as possible should be targeted by the vaccine. Moreover, experimental data support the notion that effective immunogenic neoantigens in patients cover a broad range of predicted affinities for the patient's MHC alleles (e.g. Gros et al., 2016). Most of the current prioritization methods instead apply an affinity threshold, for example the frequently used 500 nM limit, that may limit the selection of immunogenic neoantigens. There is therefore a need for a priorization method that avoids the limitations of current methods (e.g. exclusion due to low predicted affinity) and for a vaccination approach that allows for a personalized vaccine targeting a large and therefore broader and more complete set of neoantigens.

SUMMARY OF THE INVENTION

In a first aspect, the present invention provides a method for selecting cancer neoantigens for use in a personalized vaccine comprising the steps of:

(a) determining neoantigens in a sample of cancerous cells obtained from an individual, wherein each neoantigen
 is comprised within a coding sequence,
 comprises at least one mutation in the coding sequence resulting in a change of the encoded amino acid sequence that is not present in a sample of non-cancerous cells of said individual, and
 consists of 9 to 40, preferably 19 to 31, more preferably 23 to 25, most preferably 25 contiguous amino acids of the coding sequence in the sample of cancerous cells, (b) determine for each neoantigen the mutation allele frequency of each of said mutations of step (a) within the coding sequence, (c) determining the expression level of each coding sequence comprising at least one of said mutations,
 (i) in said sample of cancerous cells, or
 (ii) from an expression database of the same cancer type as the sample of cancerous cells, (d) predicting the MHC class I binding affinity of the neoantigens, wherein
 (I) the HLA class I alleles are determined from the sample of non-cancerous cells of said individual,
 (II) for each HLA class I allele determined in (I) the MHC class I binding affinity of each fragment consisting of 8 to 15, preferably 9 to 10, more preferably 9, contiguous amino acids of the neoantigen is predicted, wherein each fragment is comprising at least one amino acid change caused by the mutation of step (a), and (III) the fragment with the highest MHC class I binding affinity determines the MHC class I binding affinity of the neoantigen, (e) ranking the neoantigens according to the values determined in steps (b) to (d) for each neoantigen from highest to lowest values, yielding a first, a second and a third list of ranks, (f) calculating a rank sum from said first, second and third list of ranks and ordering the neoantigens by increasing rank sum, yielding a ranked list of neoantigens, (g) selecting 30-240, preferably 40-80, more preferably 60, neoantigens from the ranked list of neoantigens obtained in (f) starting with the lowest rank.

In a second aspect, the present invention provides a method for constructing a personalized vector encoding a combination of neoantigens according to the first aspect of the invention for use as a vaccine, comprising the steps of:

(i) ordering the list of neoantigens in at least 10ˆ5-10ˆ8, preferably 10ˆ6 different combinations, (ii) generating all possible pairs of neoantigen junction segments for each combination, wherein each junction segment comprises 15 adjoining contiguous amino acids on either side of the junction, (iii) predicting the MHC class I and/or class II binding affinity for all epitopes in junction segments wherein only HLA alleles are tested that are present in the individual the vector is designed for, and (iv) selecting the combination of neoantigens with the lowest number of junctional epitopes with an IC50 of ≤1500 nM and wherein if multiple combinations have the same lowest number of junctional epitopes the combination first encountered is selected.

In a third aspect, the present invention provides a vector encoding the list of neoantigens according to the first aspect of the invention or the combination of neoantigens according to the second aspect of the invention.

In a fourth aspect, the present invention provides a collection of vectors encoding each a different set of neoantigens according to the first aspect of the invention or the combination of neoantigens according to the second aspect of the invention, wherein the collection comprises 2 to 4, preferably 2, vectors and preferably wherein the vector inserts encoding the portion of the list are of about equal size in number of amino acids.

In a fifth aspect, the present invention provides a vector according to the third aspect of the invention or a collection of vectors according to the fourth aspect of the invention for use in cancer vaccination.

LIST OF FIGURES

In the following, the content of the figures comprised in this specification is described. In this context please also refer to the detailed description of the invention above and/or below.

Figure 1B:
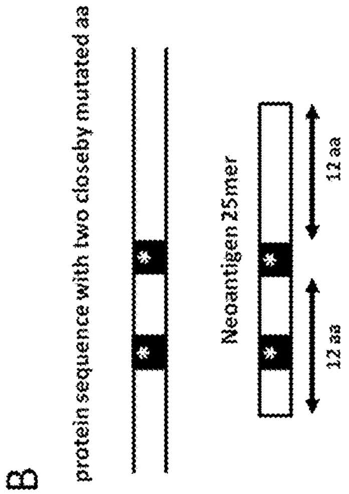
Figure 1C:
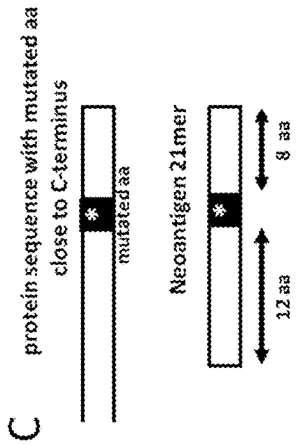

FIG. 1: Generation of neoantigens derived from a SNV: (A) generation of 25mer neoantigens with the mutation centered and flanked by 12 wt aa upstream and downstream, (B) generation of 25mer neoantigens including more than one mutation and (C) generation of a neoantigen shorter than a 25mer when the mutation is close to the end or start of the protein sequence.

Figure 2A:
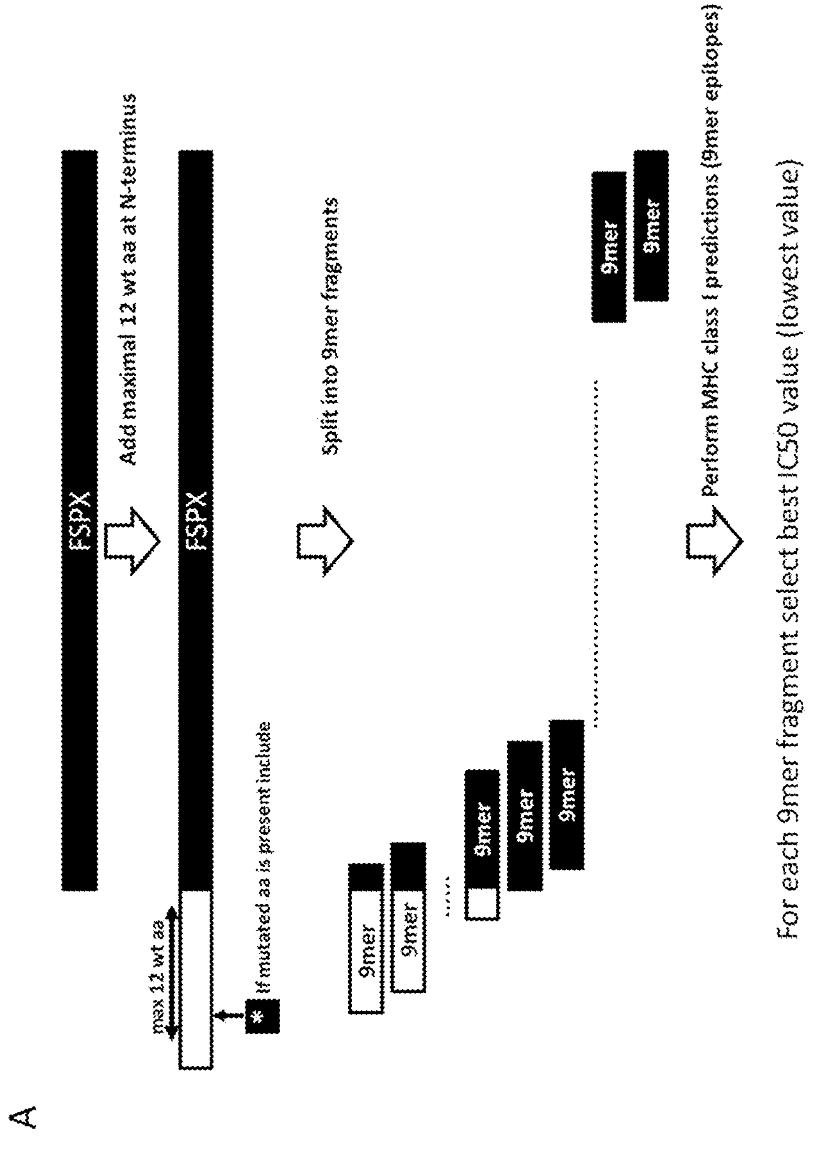

FIG. 2: Generation of neoantigens derived from indels generating a frameshift peptide (FSP). The process comprises splitting of FSPs into smaller fragments, preferably 25mers.

FIG. 3: Schematic description of the generation of the RSUM ranked list from the three individual rank scores FIG. 4: Schematic description of the procedure to optimize the length of overlapping neoantigens derived from a FSP.

Figure 5:
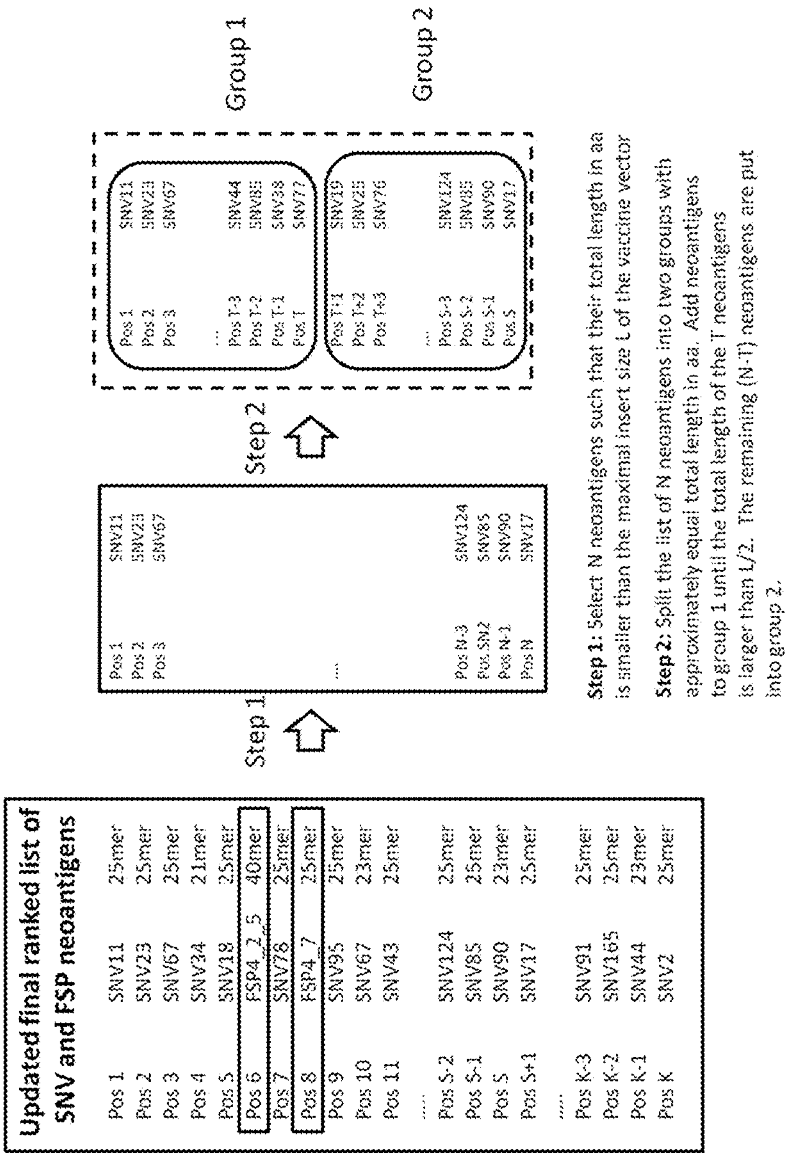

FIG. 5: Schematic description of the procedure to split K (preferably 60) neoantigens into two smaller lists of approximately equal overall length.

FIG. 6: Examples of FSP fragment merging: Example 1 refers to the FSP generated by the 2 nucleotide deletion chr11:1758971_AC. Four neoantigen sequences (FSP fragments) are merged into one 30 amino acid long neoantigen. Example 2 refers to the FSP generated by the one nucleotide insertion chr6:168310205_-_T. two neoantigen sequences (FSP fragments) are merged into one 31 amino acid long neoantigen.

FIG. 7: Validation of the prioritization method: Mutations from 14 cancer patients were ranked applying the prioritization method from Example 1. The figure reports the position in the ranked list for mutations that have been experimentally shown to induce an immune response. Ranks are indicated by a circle (A) or a square (B) for RSUM ranking including the patients' NGS-RNA data (A) or without the patients' NGS-RNA data (B)

Figure 8:
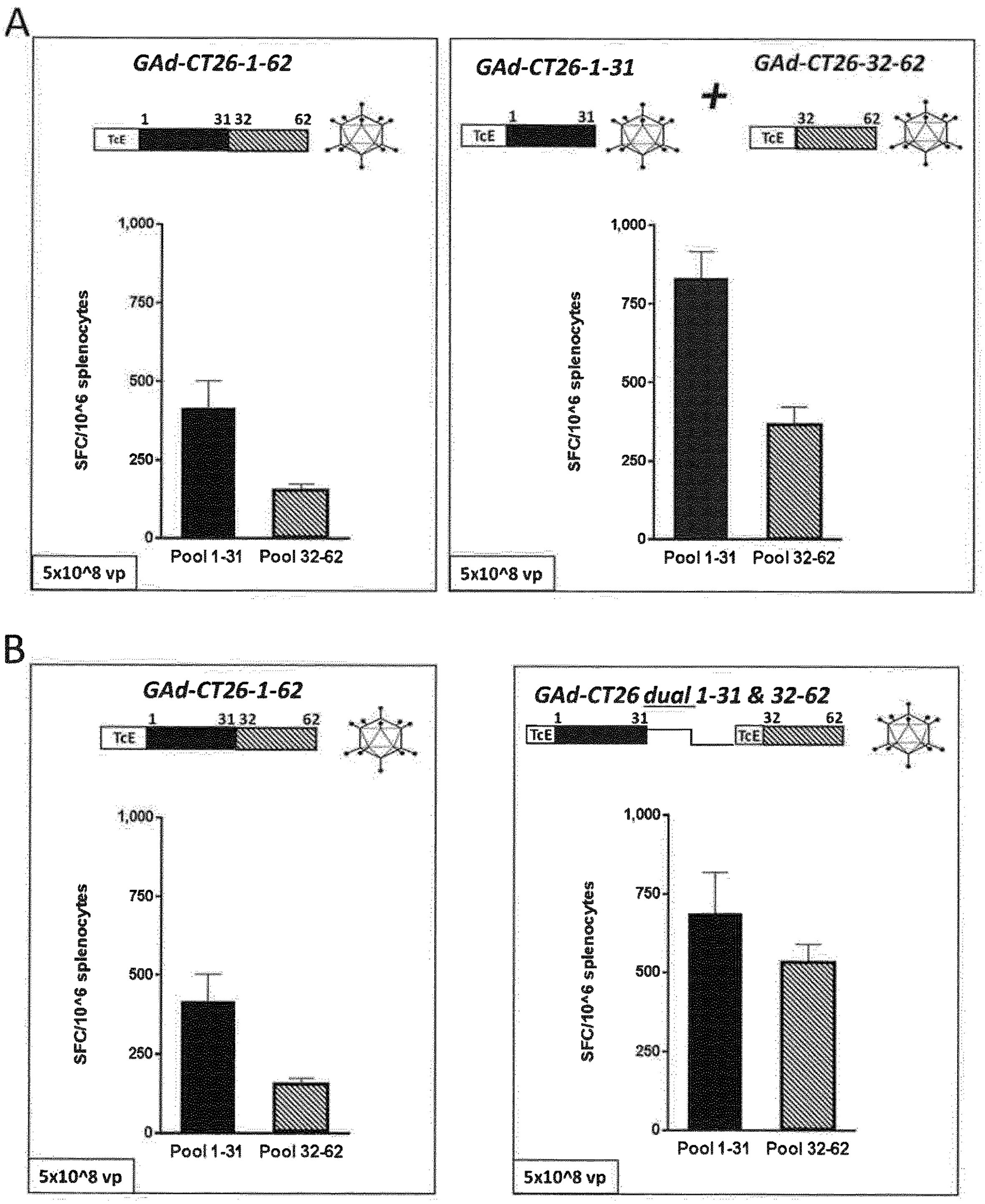

FIG. 8: Immunogenicity of a single GAd vector or two GAd vectors encoding 62 neoantigens. One GAd vector encoding all 62 neoantigens in a single expression cassette (GAd-CT26-1-62) induces a weaker immune response compared to two co-administered GAd vectors each encoding 31 neoantigens (GAd-CT26-1-31+GAd-CT26-32-62) or one GAd vector encoding for two cassettes of 31 neoantigens each (GAd-CT26 dual 1-31 & 32-62). BalbC mice (6 mice/group) were immunized intramuscularly with (A) 5×10ˆ8 vp of GAd-CT26-1-62 or by co-administration of two vectors GAd-CT26-1-31+GAd-CT26-32-62 (5×10ˆ8 vp each) and (B) 5×10ˆ8 vp of GAd-CT26-1-62 or 5×10ˆ8 vp of dual cassette vector GAd-CT26 dual 1-31 & 32-62. T cell responses were measured on splenocytes of vaccinated mice at the peak of the response (2 weeks post vaccination) by ex-vivo IFNγ ELISpot. Responses were evaluated by using 2 peptide pools, each composed of 31 peptides encoded by the vaccine constructs (pool 1-31 neoantigens 1 to 31; pool 32-62 neoantigens 32 to 62). Each of the polyneoantigen vectors comprises a T cell enhancer sequence (TPA) added to the N-terminus of the assembled polyneoantigens and an influenza HA tag at the C-terminus for monitoring expression.

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU- PAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

In the context of the present specification, the term "major histocompatibility complex" (MHC) is used in its meaning known in the art of cell biology and immunology; it refers to a cell surface molecule that displays a specific fraction (peptide), also referred to as an epitope, of a protein. There a two major classes of MHC molecules: class I and class II. Within the MHC class I two groups can be distinguished based on their polymorphism: a) the classical (MHC-Ia) with corresponding polymorphic HLA-A, HLA-B, and HLA-C genes, and b) the non-classical (MHC-Ib) with corresponding less polymorphic HLA-E, HLA-F, HLA-G and HLA-H genes.

MHC class I heavy chain molecules occur as an alpha chain linked to a unit of the non-MHC molecule β2-microglobulin. The alpha chain comprises, in direction from the N-terminus to the C-terminus, a signal peptide, three extracellular domains (α1-3, with α1 being at the N terminus), a transmembrane region and a C-terminal cytoplasmic tail. The peptide being displayed or presented is held by the peptide-binding groove, in the central region of the α1/α2 domains.

The term "β2-microglobulin domain" refers to a non-MHC molecule that is part of the MHC class I heterodimer molecule. In other words, it constitutes the β chain of the MHC class I heterodimer.

Classical MHC-Ia molecules principle function is to present peptides as part of the adaptive immune response. MHC-Ia molecules are trimeric structures comprising a membrane-bound heavy chain with three extracellular domains (α1, α2 and α3) that associates non-covalently with β2-microglobulin (β2m) and a small peptide which is derived from self-proteins, viruses or bacteria. The α1 and α2 domains are highly polymorphic and form a platform that gives rise to the peptide-binding groove. Juxtaposed to the conserved α3 domain is a transmembrane domain followed by an intracellular cytoplasmic tail.

To initiate an immune response classical MHC-Ia molecules present specific peptides to be recognized by TCR (T cell receptor) present on $CD8^+$ cytotoxic T lymphocytes (CTLs), while NK cell receptors present in natural killer cells (NK) recognize peptide motifs, rather than individual peptides. Under normal physiological conditions, MHC-Ia molecules exist as heterotrimeric complexes in charge of presenting peptides to CD8 and NK cells, however, The term "human leukocyte antigen" (HLA) is used in its meaning known in the art of cell biology and biochemistry; it refers to gene loci encoding the human MHC class I proteins. The three major classical MHC-Ia genes are HLA-A, HLA-B and HLA-C, and all of these genes have a varying number of alleles. Closely related alleles are combined in subgroups of a certain allele. The full or partial sequence of all known HLA genes and their respective alleles are available to the person skilled in the art in specialist databases such as IMGT/HLA (ebi.ac.uk/ipd/imgt/hla/).

Humans have MHC class I molecules comprising the classical (MHC-Ia) HLA-A, HLA-B, and HLA-C, and the non-classical (MHC-Ib) HLA-E, HLA-F, HLA-G and HLA-H molecules. Both categories are similar in their mechanisms of peptide binding, presentation and induced T-cell responses. The most remarkable feature of the classical MHC-Ia is their high polymorphism, while the non-classical MHC-Ib are usually non-polymorphic and tend to show a more restricted pattern of expression than their MHC-Ia counterparts.

The HLA nomenclature is given by the particular name of gene locus (e.g. HLA-A) followed by the allele family serological antigen (e.g. HLA-A*02), and allele subtypes assigned in numbers and in the order in which DNA sequences have been determined (e.g. HLA-A*02:01). Alleles that differ only by synonymous nucleotide substitutions (also called silent or non-coding substitutions) within the coding sequence are distinguished by the use of the third set of digits (e.g. HLA-A*02:01:01). Alleles that only differ by sequence polymorphisms in the introns, or in the 5' or 3' untranslated regions that flank the exons and introns, are distinguished by the use of the fourth set of digits (e.g. HLA-A*02:01:01:02L).

MHC class I and class II binding affinity prediction; example of methods known in the art for the prediction of MHC class I or II epitopes and for the prediction of MHC class I and II binding affinity are Moutaftsi et al., 2006; Lundegaard et al., 2008; Hoof et al., 2009; Andreatta & Nielsen, 2016; Jurtz et al., 2017. Preferably the method described in Andreatta & Nielsen, 2016 is used and, in case this method does not cover one of the patients's MHC alleles, the alternative method described by Jurtz et al., 2017 is used.

Genes and epitopes related to human autoimmune reactions and the associated MHC alleles can be identified in the IEDB database (iedb.org) by applying the following query criteria: "Linear epitopes" for category Epitope, "Humans" for category Host and "Autoimmune disease" for category Disease.

The term "T cell enhancer element" refers to a polypeptide or polypeptide sequence that, when fused to an antigenic sequence or peptide, increases the induction of T cells against neo-antigens in the context of a genetic vaccination. Examples of T cell enhancers are an invariant chain sequence or fragment thereof; a tissue-type plasminogen activator leader sequence optionally including six additional downstream amino acid residues; a PEST sequence; a cyclin destruction box; an ubiquitination signal; a SUMOylation signal. Specific examples of T-cell enhancer elements are those of SEQ ID NOs 173 to 182.

The term 'coding sequence' refers to a nucleotide sequence that is transcribed and translated into a protein. Genes encoding proteins are a particular example for coding sequences.

The term 'allele frequency' refers to the relative frequency of a particular allele at a particular locus within a multitude of elements, such as a population or a population of cells. The allele frequency is expressed as a percentage or ratio. For example the allele frequency of a mutation in a coding sequence would be determined by the ratio of mutated versus non-mutated reads at the position of the mutation. A mutation allele frequency wherein at the location of the mutation 2 reads determined the mutated allele and 18 reads showed the non-mutated allele would define a mutation allele frequency of 10%. The mutation allele frequency for neoantigens generated from frameshift peptides is that of the insertion or deletion mutation causing the frameshift peptide, i.e. all mutated amino acids within the FSP would have the same mutation allele frequency, which is that of the frameshift causing insertion/deletion mutation.

The term 'neoantigen' refers to cancer-specific antigens that are not present in normal non-cancerous cells.

The term 'cancer vaccine' refers in the context of the present invention to a vaccine that is designed to induce an immune response against cancer cells.

The term 'personalized vaccine' refers to a vaccine that comprises antigenic sequences that are specific for a particular individual. Such a personalized vaccine is of particular interest for a cancer vaccine using neoantigens, since many neoantigens are specific for the particular cancer cells of an individual.

The term "mutation" in a coding sequence refers in the context of the present invention to a change in the nucleotide sequence of a coding sequence when comparing the nucleotide sequence of a cancerous cell to that of a non-cancerous cell. Changes in the nucleotide sequence that does not result in a change in the amino acid sequence of the encoded peptide, i.e. a 'silent' mutation, is not regarded as a mutation in the context of the present invention. Types of mutations that can result in the change of the amino acid sequence are without being limited to non-synonymous single nucleotide variants (SNV), wherein a single nucleotide of a coding triplet is changed resulting in a different amino acid in the translated sequence. A further example of a mutation resulting in a change in the amino acid sequence are insertion/deletion (indel) mutations, wherein one or more nucleotides are either inserted into the coding sequence or deleted from it. Of particular relevance are indel mutations that result in the shift of the reading frame which occurs if a number of nucleotides are inserted or deleted that are not dividable by three. Such a mutation causes a major change in the amino acid sequence downstream of the mutation which is referred to as a frameshift peptide (FSP).

The term 'Shannon entropy' refers to the entropy associated with the number of conformations of a molecule, e.g. a protein. Methods known in the art to calculate the Shannon entropy are Strait & Dewey, 1996 and Shannon 1996. For a polypeptide the Shannon entropy (SE) can be calculated as $SE=(-\Sigma p_c(aa_i)\cdot\log(p_c(aa_i)))/N$ wherein $p_c(aa_i)$ is the frequency of amino acid i in the polypeptide and the sum is calculated over all 20 different amino acids and N is the length of the polypeptide.

The term "expression cassette" is used in the context of the present invention to refer to a nucleic acid molecule which comprises at least one nucleic acid sequence that is to be expressed, e.g. a nucleic acid encoding a selection of neoantigens of the present invention or a part thereof, operably linked to transcription and translation control sequences. Preferably, an expression cassette includes cis-regulating elements for efficient expression of a given gene, such as promoter, initiation-site and/or polyadenylation-site. Preferably, an expression cassette contains all the additional elements required for the expression of the nucleic acid in the cell of a patient. A typical expression cassette thus contains a promoter operatively linked to the nucleic acid sequence to be expressed and signals required for efficient polyadenylation of the transcript, ribosome binding sites, and translation termination. Additional elements of the cassette may include, for example enhancers. An expression cassette preferably also contains a transcription termination region downstream of the structural gene to provide for efficient termination. The termination region may be obtained from the same gene as the promoter sequence or may be obtained from a different gene.

The "IC50" value refers to the half maximal inhibitory concentration of a substance and is thus a measure of the effectiveness of a substance in inhibiting a specific biological or biochemical function. The values are typically expressed as molar concentration. The IC50 of a molecule can be determined experimentally in functional antagonistic assays by constructing a dose-response curve and examining the inhibitory effect of the examined molecule at different concentrations. Alternatively, competition binding assays may be performed in order to determine the IC50 value. Typically, neoantigen fragments of the present invention exhibit an IC50 value of between 1500 nM-1 pM, more preferably 1000 nM to 10 pM, and even more preferably between 500 nM and 100 pM.

The term "massively parallel sequencing" refers to high-throughput sequencing methods for nucleic acids. Massively parallel sequencing methods are also referred to as next-generation sequencing (NGS) or second-generation sequencing. Many different massively parallel sequencing methods are known in the art that differ in setup and used chemistry. However, all these methods have in common that they perform a very large number of sequencing reactions in parallel to increase the speed of sequencing.

The term "Transcripts Per Kilobase Million" (TPM) refers to a gene-centered metric used in massively parallel sequencing of RNA samples that normalizes for sequencing depth and gene length. It is calculated by dividing the read counts by the length of each gene in kilobases, resulting in reads per kilobases (RPK). Divide the number of all RPK values in a sample by 1,000,000 resulting in a 'per million scaling factor'. Divide the RPK values by the 'per million scaling factor' resulting in a TPM for each gene.

The overall expresion level of the gene harboring the mutation is expressed as TPM. Preferably, the "mutation-specific" expression values (corrTPM) is then determined from the number of mutated and non-mutated reads reads at the position of the mutation.

The corrected expression value corrTPM is calculated as corrTPM=TPM*(M+c)/(M+W+c). M is the number of reads spanning the location of the mutation generating the neoantigen and W is the number of reads without the mutation spanning the location of the mutation generating the neoantigens. The value c is a constant larger than 0, preferably 0.1. The value c is particular important if M and/or W is 0.

EMBODIMENTS

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. In a first aspect, the present invention provides a method for selecting cancer neoantigens for use in a personalized vaccine comprising the steps of:

- (a) determining neoantigens in a sample of cancerous cells obtained from an individual, wherein each neoantigen
  - is comprised within a coding sequence,
  - comprises at least one mutation in the coding sequence resulting in a change of the encoded amino acid sequence that is not present in a sample of non-cancerous cells of said individual, and
  - consists of 9 to 40, preferably 19 to 31, more preferably 23 to 25, most preferably 25 contiguous amino acids of the coding sequence in the sample of cancerous cells,
- (b) determine for each neoantigen the mutation allele frequency of each of said mutations of step (a) within the coding sequence,
- (c) determining the expression level of each coding sequence comprising at least one of said mutations,
  - (i) in said sample of cancerous cells, or
  - (ii) from an expression database of the same cancer type as the sample of cancerous cells,
- (d) predicting the MHC class I binding affinity of the neoantigens, wherein
  - (I) the HLA class I alleles are determined from the sample of non-cancerous cells of said individual,
  - (II) for each HLA class I allele determined in (I) the MHC class I binding affinity of each fragment consisting of 8 to 15, preferably 9 to 10, more preferably 9, contiguous amino acids of the neoantigen is predicted, wherein each fragment is comprising at least one amino acid change caused by the mutation of step (a), and
  - (III) the fragment with the highest MHC class I binding affinity determines the MHC class I binding affinity of the neoantigen,
- (e) ranking the neoantigens according to the values determined in steps (b) to (d) for each neoantigen from highest to lowest values, yielding a first, a second and a third list of ranks,
- (f) calculating a rank sum from said first, second and third list of ranks and ordering the neoantigens by increasing rank sum, yielding a ranked list of neoantigens,
- (g) selecting 30-240, preferably 40-80, more preferably 60, neoantigens from the ranked list of neoantigens obtained in (f) starting with the lowest rank.

Many cancer neoantigens are not 'seen' by the immune system because either potential epitopes are not processed/presented by the tumor cells or because immune tolerance led to elimination of T cells reactive with the mutated sequence. Therefore, it is beneficial to select, among all potential neoantigens, those having the highest chance to be immunogenic. Ideally a neoantigen would have to be present in a high number of cancer cells, being expressed in sufficient quantities and being presented efficiently to immune cells.

By selecting neoantigens comprising cancer specific mutations that have a certain mutation allele frequency, are abundantly expressed and are predicted to have a high binding affinity to MHC molecules, the chance of an immune response being induced is significantly increased. The present inventors have surprisingly found that these parameters can be most efficiently used to select suitable neoantigens elicits an increased immune response using a prioritizing method that the different parameters into account. Importantly, the method of the invention also considers neoantigens where allele frequency, expression level or predicted MHC binding affinity are not amongst the highest observed. For example a neoantigen with a high expression level and a high mutation allele frequency but a relatively low predicted MHC binding affinity can still be included in the list of selected neoantigens.

The method of the invention therefore does not use cut-off criteria commonly applied in selection processes but takes into account that neoantigens with a very high predicted suitability according to one parameter are not simply excluded from the list due to sub-optimal suitability in other parameters. This is in particular relevant for neoantigens with parameters only missing a certain cut-off criteria slightly.

Any mutation in a coding sequence (i.e. a genomic nucleic acid sequence being transcribed and translated) that is present only in cancer cells of an individual and not in healthy cells of the same individual are potentially of interest as immunogenic (i.e. capable of inducing an immune response) neoantigens. The mutation in the coding sequence must also result in changes in the translated amino acid sequence, i.e. a silent mutation only present on the nucleic acid level and without changing the amino acid sequence is therefore not suitable. Essential is that the mutation, regardless of the exact type of mutation (change of single nucleotides, insertion or deletions of single or multiple nucleotides, etc.), results in an altered amino acid sequences of the translated protein. Each amino acid present only in the altered amino acid sequence but not in the amino acid sequence resulting from the coding gene as present in the non-cancerous cells is considered to be a mutated amino acid in the context of this specification. For example mutations of the coding sequence such as insertion or deletion mutations resulting in frameshift peptides would result in a peptide wherein each amino acid that is encoded by a shifted reading frame is to be regarded as a mutated amino acid.

The mutation of the coding sequence can in principle be identified by any method of DNA sequencing of the sample obtained from an individual. A preferred method for obtaining the DNA sequence necessary to identify the mutation in the coding sequence of the individual is a massively parallel sequencing method.

The allele frequency of the mutation (i.e. the ratio of non-mutated vs mutated sequences at the position of the mutation) in the coding sequence is also an important factor for neoantigens being used in a vaccine. Neoantigens with a high allele frequency are present in a substantial number of cancer cells, resulting in neoantigens comprising these mutations being a promising target of a vaccine.

In a similar fashion it is of importance how abundantly a neoantigen is expressed within the cancer cells. The higher the expression of a neoantigen in cancer cells the more suitable is the neoantigen and the higher is the chance for a sufficient immune response against such cells. The present invention can be exercised with different ways of assessing the expression levels of neoantigens. The expression of the neoantigens can be assessed directly in the sample of cancerous cells. The expression can be measured by different methods that preferably represent the whole transcriptome, various such methods are known to the skilled person. Preferably, a method providing a fast, reliable and cost effective method to measure the transcriptome is used. One such preferred method is massively parallel sequencing.

Alternatively, if no direct measurement is available, which can e.g. be due to technical or economic reasons, expression databases can be used. The skilled person is aware of available expression databases containing gene expression data of different cancer types. A typical non-limiting example of such a database is TCGA (portal.gdc-.cancer.gov/). The expression of genes comprising the mutation identified in step (a) of the method in the same type of tumor as the individual the vaccine is designed for can be searched in these databases and can be used to determine an expression value.

It is further of importance that the selected neoantigens are efficiently presented to immune cells by MHC molecules on the cancer cells. There are different methods known in the art to predict the binding affinity of peptides to MHC class I (and class II) molecules (Moutaftsi et al., 2006; Lundegaard et al., 2008; Hoof et al., 2009; Andreatta & Nielsen, 2016; Jurtz et al., 2017). Since the MHC molecules are a highly polymorphic group of proteins with significant differences between individuals it is important to determine the MHC binding affinity for the type of MHC molecules present on the individual's cells. The MHC molecules are encoded by the group of highly polymorphic HLA genes. The method therefore uses the DNA sequencing results utilized in step (a) to identify the mutations in coding sequences to identify the HLA alleles present in the individual. For each MHC molecule corresponding to the identified HLA alleles in the individual, the MHC binding affinity to the neoantigens is determined. Towards these ends the amino acid sequence of the neoantigen is determined by in silico translation of the coding sequence. The resulting neoantigen amino acid sequence is then divided into fragments consisting of 8 to 15, preferably 9 to 10, more preferably 9, contiguous amino acids, wherein the fragment must contain at least one of the mutated amino acids of the neoantigen. The size of the fragment is restricted by the size of peptides the MHC molecule can present. For each fragment the MHC binding affinity is predicted. The MHC binding affinity is usually measured as half maximal inhibitory concentration (IC50 in [nM]). Hence, the lower the IC50 value is the higher is the binding affinity of the peptide to the MHC molecule. The fragment with the highest MHC binding affinity determines the MHC binding affinity of the neoantigen the fragment is derived from.

The method of the present invention then uses the parameters determined in steps (b) to (d), i.e. mutation allele frequency, expression level and predicted MHC class I binding affinity of the neoantigen, to select the most suitable neoantigens by applying a prioritization method to these parameters. Therefore the parameters are sorted on a ranked list. The neoantigen with the highest mutation allele frequency is assigned the first rank, i.e. rank 1, in a first list of ranks. The neoantigen with the second highest mutation allele frequency is assigned the second rank in the first list of ranks etc. until all identified neoantigens are assigned a rank on the first list of ranks.

Similarly the expression level of each coding sequence is ranked from highest to lowest, with the neoantigen with the highest expression value being assigned rank 1, the neoantigen with the second highest levels is assigned rank 2 etc. until all identified neoantigens are assigned a rank on the second list of ranks.

The MHC class I binding affinity of the neoantigens are ranked from highest to lowest binding affinity with the neoantigen with the highest MHC class I binding affinity is assigned rank 1, the neoantigen with the second highest binding affinity is assigned rank 2 etc. until all neoantigens are assigned a rank on the third list of ranks.

If any of the neoantigens has an identical mutation allele frequency, expression level and/or MHC class I binding affinity as another neoantigens, both antigens are assigned the same rank on the relevant list of ranks.

The method then uses a prioritization method that takes into account all three rankings by calculating a rank sum of the three lists of ranks. For example a neoantigen that has rank 3 on the first list of ranks, rank 13 on the second list of ranks and rank 2 on the third list or ranks has a rank sum of 18 (3+13+2). After the rank sum has been calculated for each neoantigen the rank sums are ranked according to their rank sum with the lowest rank sum being assigned rank 1 etc. yielding a ranked list of neoantigens. Neoantigens with an identical rank sum are assigned the same rank on the ranked list of neoantigens.

The final number of neoantigens present in the list is dependent on the number of mutations detected in each patient. The number of neoantigens to be used in a vaccine is limited by the vehicle or vehicles used to deliver the vaccine. For example if a single viral vector is used as a delivery vehicle, as can be the case for a genetic vaccine, the maximum insert size of this vector would limit the number of neoantigens that can be used in each vector.

Therefore, the method of the present invention selects 25-250, 30-240, 30-150, 35-80, preferably 55-65, more preferably 60 neoantigens from the list of ranked neoantigens starting with the neoantigen that has the lowest rank (i.e. lowest rank number, rank 1). In case the neoantigens are selected to be present in one set (e.g. single vehicle of a monovalent vaccine) 25-80, 30-70, 35-70, 40-70, 55-65, preferably 60 neoantigens are selected. The neoantigens not included in the first set can however be encoded by additional viral vectors for a multivalent vaccination based on co-administration of up to 4 viral vectors.

In a preferred embodiment of the first aspect of the present invention, steps (a) and (d)(I) are performed using massively parallel DNA sequencing of the samples.

In a preferred embodiment of the first aspect of the present invention, steps (a) and (d)(I) are performed using massively parallel DNA sequencing of the samples and the number of reads at the chromosomal position of the identified mutation is:

- in the sample of cancerous cells at least 2, preferably at least 3, 4, 5, or 6,
- in the sample of non-cancerous cells is 2 or less, i.e. 2, 1 or 0, preferably 0.

In an preferred alternative embodiment of the first aspect of the invention the number of reads at the chromosomal position of the identified mutation are higher in the sample of cancerous cells than in the sample of non-cancerous cells, wherein the difference between the samples is statistically significant. A statistically significant difference between two groups can be determined by a number of statistical tests known to the skilled person. One such example of a suitable statistical test is Fisher's exact test. For the purpose of the present invention two groups are considered to be different from each other if the p-value is below 0.05.

These criteria are applied to further select for neoantigens wherein the identified mutation is detected with a particular high technical reliability.

In a preferred embodiment of the first aspect of the present invention the method comprises a step (d') in addition to or alternatively to step (d), wherein step (d') comprises:

- determining the HLA class II alleles in the sample of non-cancerous cells of said individual,
- predicting the MHC class II binding affinity of the neoantigen, wherein
  - for each HLA class II allele determined the MHC class II binding affinity for each fragment of 11 to 30, preferably 15, contiguous amino acids of the neoantigen is predicted, wherein each fragment is comprising at least one mutated amino acid generated by the mutation of step (a), and
  - the fragment with the highest MHC class II binding affinity determines the MHC class II binding affinity of the neoantigen;

wherein the MHC class II binding affinity is ranked from highest to lowest MHC class II binding affinity, yielding a fourth list of ranks that is included in the rank sum of step (f).

In this embodiment an alternative or additional selection parameter is added. The MHC class II binding affinity is predicted in slightly larger fragments due to the peptides presented by MHC class II molecules being larger in size than those of MHC class I peptides. The MHC class II binding affinity is also ranked from the highest to the lowest binding affinity, with the neoantigen with the highest MHC class II binding affinity being assigned rank 1 etc. until all neoantigens are assigned a rank in the fourth list of ranks.

In case the MHC class II binding affinity is used as an additional selection parameter the fourth list is included additionally in the rank sum calculation. In case the MHC class II binding affinity is used as an alternative to the MHC class I binding affinity of step (d) the rank sum in step (f) is calculated on the first, second and fourth list of ranks only.

In a preferred embodiment of the first aspect of the present invention the at least one mutation of step (a) is a single nucleotide variant (SNV) or an insertion/deletion mutation resulting in a frame-shift peptide (FSP).

In a preferred embodiment of the first aspect of the present invention wherein the mutation is a SNV and the neoantigen has the total size defined in step (a) and consists of the amino acid caused by the mutation, flanked on each side by a number of adjoining contiguous amino acids, wherein the number on each side does not differ by more than one unless the coding sequence does not comprise a sufficient number of amino acids on either side, wherein the neoantigen has the total size defined in step (a). Preferably the mutated amino acid resulting from a SNV is located within the 'middle' of the neoantigen (i.e. flanked by an equal number of amino acids). This provides an equal chance of the mutation being present at the end or start of an epitope. The neoantigen is therefore selected with approximately (i.e. differ by not more than one) the same number of surrounding amino acids resulting from the coding sequence on each side of the mutated amino acids.

In a preferred embodiment of the first aspect of the present invention wherein the mutation results in a FSP and each single amino acid change caused by the mutation results in a neoantigen that has the total size defined in step (a) and consists of:

(i) said single amino acid change caused by the mutation and 7 to 14, preferably 8, N-terminally adjoining contiguous amino acids, and (ii) a number of contiguous amino acids adjoining the fragment of step (i) on either side, wherein the number of amino acids on either side differ by not more than one, unless the coding sequence does not comprise a sufficient number of amino acids on either side, wherein the MHC class I binding affinity of step (d) and/or the MHC class II binding affinity of step (d') is predicted for the fragment of step (i).

Each mutated amino acid of the FSP defines one distinct neoantigen. Each neoantigen consists of a mutated amino acid and a number of amino acids being one amino acid shorter than the size of the fragment used to determine MHC class I binding affinity (i.e. 7 to 14) which are located N-terminally of the mutated amino acid. The neoantigen further consists of a number of contiguous amino acids derived from the coding sequence that form with the sequence of the neoantigen fragment of step (i) a contiguous sequence in the coding sequence. The number of amino acids surrounding the neoantigen fragment of step (i) on either side differs by only one, wherein the total size of the neoantigen is as defined in step (a). The neoantigen fragment of step (i) is used to determine the MHC class I and/or class II binding affinity.

For example a mutated amino acid on relative position 20 of a translated coding sequence would define a neoantigen fragment including a contiguous amino acid sequence of 8 contiguous amino acids (i.e. fragment of step (i)) ranging from position 12 to 20. The complete neoantigen sequence of 25 amino acids according to step (ii) would consist of amino acids 4 to 28. The neoantigen fragment ranging from position 12 to 20 consisting of 9 amino acids would be used to determine the MHC binding affinity.

In a preferred embodiment of the first aspect of the present invention the mutation allele frequency of the neoantigen determined in step (b) in the sample of cancerous cells is at least 2%, preferably at least 5%, more preferably at least 10%.

In a preferred embodiment of the first aspect of the present invention step (g) further comprises removing neoantigens from genes linked to autoimmune disease, from the ranked list of neoantigens. The skilled person is aware of neoantigens associated with autoimmune diseases from public databases. One such example of a database is the IEDB database (iedb.org). Exclusion of a neoantigen candidate can be performed both at the gene level if the gene harboring the mutation belongs to one of those genes linked to autoimmune disease in the IEDB database or, in a less stringent manner, not only if the patient has a mutation in a gene known to be involved in autoimmunity but one of the patient's MHC alleles is also identical to the allele described in the IEDB database for the human autoimmune disease epitope in connection with the described autoimmune phenomenon.

In a preferred embodiment neoantigens associated with an autoimmune disease are not removed from the ranked list of neoantigens if the database specifies a certain MHC class I allele for this association and the corresponding HLA allele was not found in the individual in step (d)(I).

In a preferred embodiment of the first aspect of the present invention step (g) further comprises removing neoantigens with a Shannon entropy value for their amino acid sequence lower than 0.1 from said ranked list of neoantigens.

In a preferred embodiment of the first aspect of the present invention the expression level of said coding genes in step (c)(i) is determined by massively parallel transcriptome sequencing.

In a preferred embodiment of the first aspect of the present invention the expression level determined in step (c)(i) uses a corrected Transcripts Per Kilobase Million (corrTPM) value calculated according to the following formula $$corrTPM = TPM * \left(\frac{M + c}{M + W + c}\right)$$

wherein M is the number of reads spanning the location of the mutation of step (a) that comprise the mutation and W is the number of reads spanning the location of the mutation of step (a) without the mutation and TPM is the Transcripts Per Kilobase Million value of the gene comprising the mutation and the c is a constant larger than 0, preferably c is 0.1.

In a preferred embodiment of the first aspect of the present invention the rank sum in step (f) is a weighted rank sum, wherein the number of neoantigens determined in step (a) is added to the rank value of each neoantigen:

- in the third list of ranks for which the prediction of MHC class I binding affinity of step (d) resulted in an IC50 value higher than 1000 nM and/or
- in the fourth list of ranks for which the prediction of MHC class II binding affinity of step (d') resulted in an IC50 value higher than 1000 nM.

This weighing of the MHC binding affinity penalizes a very low MHC class I and/or class II binding affinity by adding ranks.

In a preferred embodiment of the first aspect of the present invention the rank sum in step (f) is a weighted rank sum, wherein in case of step (c)(i) being performed by massively parallel transcriptome sequencing, the rank sum of step (f) is multiplied by a weighing factor (WF), wherein WF is 1, if the number of mapped transcriptome reads for the mutation is >0, 2, if the number of mapped transcriptome reads for the mutation is 0 and the number of mapped reads for the non-mutated sequence is 0 and the transcripts-per-million (TPM) value is at least 0.5, 3, if the number of mapped transcriptome reads for the mutation is 0 and the number of mapped reads for the non-mutated sequence is >0 and the transcripts-per-million (TPM) value is at least 0.5, 4, if the number of mapped transcriptome reads for the mutation is 0 and the number of mapped reads for the non-mutated sequence is 0 and the transcripts-per-million (TPM) value is <0.5, or 5, if the number of mapped transcriptome reads for the mutation is 0 and the number of mapped reads for the non-mutated sequence is >0 and the transcripts-per-million (TPM) value is <0.5.

The weighing matrix penalizes certain neoantigens for which the sequencing results are either of poor quality (i.e. number of mapped reads is low) and/or if the expression value (i.e. TPM value) is below a certain threshold. This mode of weighing (i.e. prioritizing) certain parameters provides neoantigens with a better immunogenicity than using cutoff values for the single parameters, which would eliminate certain neoantigens due to a low suitability in one parameter even though other parameter qualifies the neoantigen as suitable.

In a preferred embodiment of the first aspect of the present invention step (g) comprises an alternative selection process, wherein the neoantigens are selected from the ranked list of neoantigens starting with the lowest rank until a set maximum size in total overall length in amino acids for all selected neoantigens is reached, wherein the maximum size is between 1200 and 1800, preferably 1500 amino acids for each vector. The process can be repeated in a multivalent vaccination approach, wherein the maximum size indicated above applies for each vehicle used in the multivalent approach. For example a multivalent approach based on 4 vectors could for example allow a total limit of 6000 amino acids. This embodiment takes the maximum size for neoantigens allowed by a certain delivery vehicle into account. Therefore, the number of neoantigens selected from the ranked list is not determined by the number of neoantigens but takes the size of neoantigens into account. A number of small neoantigens in the ranked list of antigens would allow to include more antigens within the list of selected antigens.

In a preferred embodiment of the first aspect of the present invention two or more neoantigens are merged into one new neoantigen if they comprise overlapping amino acid sequence segments. In some case neoantigens can contain overlapping amino acid sequences. This is particularly often the case for FSP derived neoantigens. In order to avoid redundant overlapping sequences the neoantigens are merged into a single new neoantigen that consists of the non-redundant portions of the merged neoantigens. A merged new neoantigen can have a size larger than defined in step (a) of the first aspect of the invention, depending on the number of neoantigens merged and the degree of overlap.

In a preferred embodiment of the first aspect of the present invention the personalized vaccine is a personalized genetic vaccine. The term 'genetic vaccine' is used synonymously to 'DNA vaccine' and refers to the use of genetic information as a vaccine and the cells of the vaccinated subject produce the antigen the vaccination is directed against.

In a preferred embodiment of the first aspect of the present invention the personalized vaccine is a personalized cancer vaccine.

In a second aspect, the present invention provides a method for constructing a personalized vector encoding a combination of neoantigens according to the first aspect of the invention for use as a vaccine, comprising the steps of:

(i) ordering the list of neoantigens in at least 10^5-10^8, preferably 10^6 different combinations, (ii) generating all possible pairs of neoantigen junction segments for each combination, wherein each junction segment comprises 15 adjoining contiguous amino acids on either side of the junction, (iii) predicting the MHC class I and/or class II binding affinity for all epitopes in junction segments wherein only HLA alleles are tested that are present in the individual the vector is designed for, and
(iv) selecting the combination of neoantigens with the lowest number of junctional epitopes with an IC50 of ≤1500 nM and wherein if multiple combinations have the same lowest number of junctional epitopes the combination first encountered is selected.

The list of selected neoantigens according to the first aspect of the invention can be arranged into a single combined neoantigen. The junctions where the individual neoantigens are joined can result in novel epitopes that may lead to unwanted off target effects not related to epitopes being present on cancerous cells. Therefore, it is advantageous if the epitopes created by the junction of individual neoantigens have a low immunogenicity. Towards these ends the neoantigens are arranged in different orders resulting in different junction epitopes and the MHC class I and class II binding affinity of those junction epitopes is predicted. The combination with the lowest number of junctional epitopes with an IC50 value of ≤1500 nM is selected. The number of different combinations of selected neoantigens is limited primarily by computing power available. A compromise between computing resources used and accuracy needed is if 10^5-10^8, preferably 10^6 different combinations of neoantigens are used wherein the MHC class I and/or class II binding affinity of the junctional epitopes of each neoantigen junction is predicted.

In an alternative second aspect, the present invention provides a method for constructing a personalized vector encoding a combination of neoantigens for use as a vaccine, comprising the steps of:
(i) ordering a list of neoantigens in at least 10^5-10^8, preferably 10^6 different combinations,
(ii) generating all possible pairs of neoantigen junction segments for each combination, wherein each junction segment comprises 15 adjoining contiguous amino acids on either side of the junction,
(iii) predicting the MHC class I and/or class II binding affinity for all epitopes in junction segments wherein only HLA alleles are tested that are present in the individual the vector is designed for, and
(iv) selecting the combination of neoantigens with the lowest number of junctional epitopes with an IC50 of ≤1500 nM and wherein if multiple combinations have the same lowest number of junctional epitopes the combination first encountered is selected.

The list of neoantigens can be arranged into a single combined neoantigen. The junctions where the individual neoantigens are joined can result in novel epitopes that may lead to unwanted off target effects not related to epitopes being present on cancerous cells. Therefore, it is advantageous if the epitopes created by the junction of individual neoantigens have a low immunogenicity. Towards these ends the neoantigens are arranged in different orders resulting in different junction epitopes and the MHC class I and class II binding affinity of those junction epitopes is predicted. The combination with the lowest number of junctional epitopes with an IC50 value of ≤1500 nM is selected. The number of different combinations of selected neoantigens is limited primarily by computing power available. A compromise between computing resources used and accuracy needed is if 10^5-10^8, preferably 10^6 different combinations of neoantigens are used wherein the MHC class I and/or class II binding affinity of the junctional epitopes of each neoantigen junction is predicted.

In a third aspect, the present invention provides a vector encoding the list of neoantigens according to the first aspect of the invention or the combination of neoantigens according to the second aspect of the invention.

It is preferred that the vector comprises one or more elements that enhance immunogenicity of the expression vector. Preferably such elements are expressed as a fusion to the neoantigens or neoantigens combination polypeptide or are encoded by another nucleic acid comprised in the vector, preferably in an expression cassette.

In a preferred embodiment of the third aspect of the invention the vector additionally comprises a T-cell enhancer element, preferably (SEQ ID NO: 173 to 182), more preferably SEQ ID NO: 175, that is fused to the N-terminus of the first neoantigen in the list.

The vector of the third aspect or the collection of vectors of the fourth aspect, wherein the vector in each case is independently selected from the group consisting of a plasmid; a cosmid; a liposomal particle, a viral vector or a virus like particle; preferably an alphavirus vector, a venezuelan equine encephalitis (VEE) virus vector, a sindbis (SIN) virus vector, a semliki forest virus (SFV) virus vector, a simian or human cytomegalovirus (CMV) vector, a Lymphocyte choriomeningitis virus (LCMV) vector, a retroviral vector, a lentiviral vector, an adenoviral vector, an adeno-associated virus vector a poxvirus vector, a vaccinia virus vector or a modified vaccinia ankara (MVA) vector. It is preferred that a collection of vectors, wherein each member of the collection comprises a polynucleotide encoding a different antigen or fragments thereof and, which is thus typically administered simultaneously uses the same vector type, e.g. an adenoviral derived vector.

The most preferred expression vectors are adenoviral vectors, in particular adenoviral vectors derived from human or non-human great apes. Preferred great apes from which the adenoviruses are derived are Chimpanzee (*Pan*), *Gorilla* (*Gorilla*) and orangutans (*Pongo*), preferably Bonobo (*Pan paniscus*) and common Chimpanzee (*Pan troglodytes*). Typically, naturally occurring non-human great ape adenoviruses are isolated from stool samples of the respective great ape. The most preferred vectors are non-replicating adenoviral vectors based on hAd5, hAd11, hAd26, hAd35, hAd49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3 vectors or replication-competent Ad4 and Ad7 vectors. The human adenoviruses hAd4, hAd5, hAd7, hAd11, hAd26, hAd35 and hAd49 are well known in the art. Vectors based on naturally occurring ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093. Vectors based on naturally occurring PanAd1, PanAd2, PanAd3, ChAd55, ChAd73, ChAd83, ChAd146, and ChAd147 are described in detail in WO 2010/086189.

In a preferred embodiment of the third aspect of the present invention, the vector comprises two independent expression cassettes wherein each expression cassette encodes a portion of the list of neoantigens according to the first aspect of the invention or the combination of neoantigens according to the second aspect of the invention. Preferably, the portion of the list encoded by the expression cassettes are of about equal size in number of amino acids.

In a preferred embodiment of the third aspect of the present invention the vector comprises an expression cassette encoding the selected neoantigens of the ranked list of neoantigens according to the first aspect of the invention wherein the list of selected neoantigens is split into two parts of approximately equal length, wherein the two parts are separated by an internal ribosome entry site (IRES) element or a viral 2A region (Luke et al., 2008), for example the aphtovirus Foot and Mouth Disease Virus 2A region (SEQ ID NO: 184 APVKQTLNFDLLKLAGDVESNPGP) which mediates polyprotein processing by a translational effect known as ribosomal skip (Donnelly et al., J. Gen. Virology 2001). Optionally in each of the two parts a T-cell enhancer element, preferably (SEQ ID NO: 173 to 182), more preferably SEQ ID NO: 175, is fused to the N-terminus of the first neoantigen in the list.

In a fourth aspect, the present invention provides a collection of vectors encoding each a portion of the list of neoantigens according to the first aspect of the invention or the combination of neoantigens according to the second aspect of the invention, wherein the collection comprises 2 to 4, preferably 2, vectors and preferably wherein the vector inserts encoding the portion of the list are of about equal size in number of amino acids.

In a fifth aspect, the present invention provides a vector according to the third aspect of the invention or a collection of vectors according to the fourth aspect of the invention for use in cancer vaccination.

The vector of the third aspect of the invention or the collection of vectors according to the fourth aspect of the invention for use in cancer vaccination, wherein the cancer is selected from the group consisting of malignant neoplasms of lip, oral cavity, pharynx, a digestive organ, respiratory organ, intrathoracic organ, bone, articular cartilage, skin, mesothelial tissue, soft tissue, breast, female genital organs, male genital organs, urinary tract, brain and other parts of central nervous system, thyroid gland, endocrine glands, lymphoid tissue, and haematopoietic tissue.

In a preferred embodiment of the fifth aspect of the invention the vaccination regimen is a heterologous prime boost with two different viral vectors. Preferred combinations are Great Apes derived adenoviral vector for priming and a poxvirus vector, a vaccinia virus vector or a modified vaccinia ankara (MVA) vector for boosting. Preferably these are administered sequentially with an interval of at least 1 week, preferably of 6 weeks.

EXAMPLES

The present invention describes a method to score tumor mutations for their likelihood to give rise to immunogenic neoantigens. This approach analyzes the next generation DNA sequencing (NGS-DNA) data and, optionally, the next generation RNA sequencing (NGS-RNA) data of a tumor specimen and the NGS-DNA data of a normal sample obtained from the same patient as described below.

The personalized approach relies on NGS data obtained by analyzing samples collected from a cancer patient. For each patient, NGS-DNA exome data from tumor DNA are compared to those obtained from normal DNA in order to identify somatic mutations confidently present in the tumor and not in the normal sample that generate changes in the amino acid sequence of a protein.

Normal exome DNA is further analyzed to determine the patient HLA class I and class II alleles. NGS-RNA data from the tumor sample, if available, is analyzed to determine the expression of genes harbouring the mutations.

The examples below refer to the following aspect of the invention:

Example 1: Description of the prioritization method

Example 2: Application of the prioritization method to an existing literature NGS dataset Example 3: Validation of the prioritization method Validation of the prioritization method was performed by measuring its performance against a dataset (published studies) in which both NGS data and immunogenic neoantigens are described. In the example the prioritization method a and b are used. This example shows that by selecting the top 60 neoantigens a very high portion of known immunogenic neoantigens are included in the vaccine, both by using method a (with patient NGS-RNA) or method b (no patient NGS-RNA).

Example 4: optimization of neoantigen layout for synthetic genes encoding neoantigens to be delivered by a genetic vaccine vector.

Demonstration that splitting 62 selected neoantigens obtained from a mouse model into two synthetic genes (total 31+31=62 neoantigens) results in improved immunogenicity compared to the use of one synthetic gene encoding for 62 neoantigens.

Example 1: Description of the Priorization Method

Step 1: Identification of Mutations that can Generate a Neoantigen

Mutations defined as confidently present in the tumor ideally but not exclusively fulfil the following criteria:

- mutation allele frequency (MF) in the tumor DNA sample>=10%,
- ratio of the MF between the tumor DNA sample and the control DNA sample>=5,
- number of mutated reads at the chromosomal position of somatic variant in the tumor DNA>2,
- number of mutated reads at the chromosomal position of somatic variant in the normal DNA<2, Two types of somatic mutations are considered within the method of the present invention: single nucleotide variants (SNVs) generating a non-synonymous codon change with a resulting mutated amino acid in a protein and insertions/deletions (indels) that generate frameshift peptides (FSPs) by changing the reading frame of a protein-encoding mRNA.

Step 2: Generate the Structure of Each Neoantigen

Step 2.1:

For each mutation a neoantigen peptide sequence is generated in the following way:

a) SNVs:

A 25 amino acid long sequence is generated with the mutated amino located in the centre and flanked, on both sides, by preferably A=12 non-mutated amino acids (FIG. 1). In cases where the mutation is localized close to the N-terminus or C-terminus of the protein less than A=12 non-mutated amino acids will be included. A minimal number of 8 non-mutated amino acids is added either upstream or downstream of the mutation. This ensures that the neoantigen can contain a 9mer neoepitope with at least 1 mutated amino acids. Adding for example 4 non-mutated amino acids upstream and 2 downstream is not possible, this would correspond to a very short protein.

Occasionally two (or even more) mutations, SNVs and/or indels, are present within a small distance (distance less than or equal to A amino acids) in the protein. In these cases the segment of the A non-mutated amino acids that is added N-terminal or C-terminal will be modified such that the additional mutation(s) is(are) present. (FIG. 1).

For each neoantigen a MHC class I 9mer epitope prediction is then performed with the patient's HLA alleles identified from the NGS-DNA exome data. The IC50 value associated with the neoantigen is then chosen as the one with the lowest IC50 value across all predicted epitopes that comprise at least 1 mutated amino acids and across all of the patient's class I alleles.

b) Frame-Shift Peptides (FSPs):

For FSPs maximal N=12 non-mutated amino acids are added at the N-terminus of the FSP (FIG. 2A); if less than 12 non-mutated amino acids are present upstream of the FSP only these are added. In case a SNV leading to a mutated amino acid is present within the added non-mutated segment the mutated amino acid is included. This generates an expanded FSP peptide sequence.

The resulting expanded FSP peptide sequence is then split into 9 amino acid long fragments and MHC class I 9mer epitope prediction is performed (with the patient's HLA alleles) on all fragments containing at least 1 mutated amino acid. The IC50 value associated with each fragment is then chosen as the lowest predicted IC50 value across all the alleles examined.

Figure 2B:
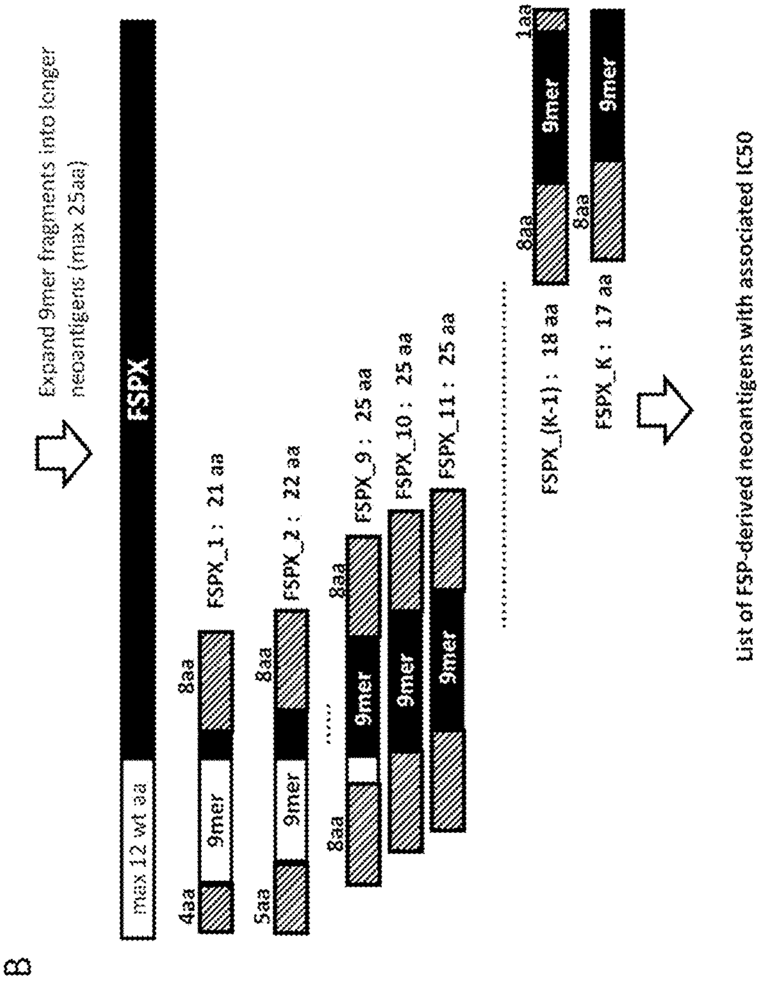

Each 9 amino acid fragment is then expanded into a 25 amino acid long neoantigen sequence by adding the 8 upstream and 8 downstream amino acids to the N-terminal and C-terminal end of the fragment, respectively (FIG. 2B). For 9 amino acid fragments close to the N- or C-terminal end of the expanded FSP less amino acids are added.

The resulting neoantigen sequences with their associated IC50 are then added to the list of neoantigen sequences obtained from the SNVs.

Step 2.2 (Optional)

An optional safety filter is then performed on the RSUM ranked list of neoantigens in order to remove those neoantigens that represent a potential risk of inducing autoimmunity. The filter examines if the gene encoding for the neoantigen is part of a black list of genes (for example retrieved from the IEDB database) containing known class I and class II MHC epitopes linked to autoimmune disease. If available, the list also contains the HLA allele of the epitope.

Neoantigens are removed if their originating mutation is from one of the genes in the black list and at the same time one of the HLA alleles of the patient corresponds to the HLA linked with the gene to autoimmunity disease.

For genes in the black list where no information on the epitope's HLA allele is available, the neoantigen is removed independently from the patient's HLA alleles.

Step 2.3 (Optional)

The list of candidate neoantigens is then filtered to remove neoantigens that encode peptides with a low complexity amino acid sequence (presence of segments in the sequence where one or more amino acid(s) are repeated multiple times).

Once converted into a nucleotide sequences these segments are likely to represent regions with a high content in G or C nucleotides. These regions can therefore generate problems either during the initial construction/synthesis of the vaccine expression cassette and/or they could also negatively affect expression of the encoded polypeptides.

The identification of low complexity amino acid sequences is performed by estimating the Shannon entropy of the neoantigen sequence divided by its length in amino acids. The Shannon entropy is a metric commonly used in information theory and measures the average minimum number of bits needed to encode a string of symbols based on the alphabet size and the frequency of the symbols.

In the present method the metric has been applied to the string of amino acids present in neoantigen sequence. Neoantigens that have a Shannon entropy value lower than 0.10 are removed from the list.

Step 3:

Description of the Process for Prioritization of a Patient's Neoantigens

Data required for performing the prioritization are

- List of M neoantigens (from non-synonymous SNVs or frameshift indels) from Step 2
- Mutant allele frequency data for each neoantigen from Step 1
- Expression data for each neoantigen: from RNA sequencing data (Step 1) or, as an alternative method (B) (if no NGS-RNA data is available from the tumor sample), from a general gene-level expression database of the same tumor type
- Predicted MHC class I binding affinity for the best mutated 9mer epitope for each neoantigen (from step 3).

The prioritization strategy is based on an overall score obtained by the combination of three separate independent rank score values (RFREQ, REXPR, RIC50). The three rank score values are obtained by ordering the list of M neoantigens independently according to one of the following parameters (the result will therefore be three different ordered lists of neoantigens, each list thus providing a rank score).

Step 3.1: Allele Frequency Rank Score (RFREQ)

Each neoantigens is associated with the observed tumor allele frequency of the mutation generating the neoantigen. The list of M neoantigens is ordered from the highest allele frequency to the lowest allele frequency. The neoantigen with the highest allele frequency has a rank score RFREQ equal to 1, the second highest a rank score RFREQ=2 and so on. If neoantigens with identical allele frequency are present they are given the same rank score RFREQ, i.e. the lowest rank score might be less than M (Table 1)

TABLE 1

Neoantigens with equal mutant allele frequency get the same rank score RFREQ

| | Mutant allele frequency | RFREQ |
|---|---|---|
| SNV101 | 0.48 | 1 |
| SNV16 | 0.43 | 2 |
| SNV34 | 0.35 | 3 |
| SNV87 | 0.33 | 4 |
| SNV23 | 0.32 | 5 |
| FSP4_5 | 0.3 | 6 |
| SNV120 | 0.28 | 7 |
| SNV11 | 0.26 | 8 |
| SNV67 | 0.21 | 9 |
| SNV18 | 0.21 | 9 |
| SNV109 | 0.2 | 10 |

Step 3.2: RNA Expression Rank Score (REXPR)

The expression level of each neoantigen is determined from the tumor NGS-RNA data by calculating the gene-centred Transcripts Per Kilobase Million (TPM) value (Li & Dewey, 2011) considering all mapped reads. The TPM value is then modified taking into account the number of mutated and wild type reads spanning the location of the mutation in the NGS-RNA transcriptome data (corrTPM):

$$corrTPM = TPM(\text{gene}) * \left( \frac{num \text{ reads } (mut) + 0.1}{num \text{ reads } (mut) + numreads(wt) + 0.1} \right)$$

A preferred value of 0.1 is added to both the numerator and enumerator in order to include also cases where no reads are present at the location of the mutation.

If no NGS-RNA sequencing data is available from the patient's tumor, the corrTPM is replaced, for each neoantigen, by the corresponding gene's median TPM value as present in an expression database from the same tumor type.

Neoantigens are then ranked according to the expression level as determined by the corrTPM value. Ordering is from highest expression (score REXP equal to 1) down to lowest expression. Neoantigens with the same corrTPM value are given the same rank score REXPR (Table 2).

TABLE 2

Neoantigens with equal expression value corrTPM get the same rank score REXPR

| | corrTPM | REXPR |
|---|---|---|
| SNV11 | 47.53 | 1 |
| SNV88 | 46.9 | 2 |
| SNV34 | 37.64 | 3 |
| SNV67 | 29.72 | 4 |

TABLE 2-continued

Neoantigens with equal expression value corrTPM get the same rank score REXPR

| | corrTPM | REXPR |
|---|---|---|
| SNV23 | 26.12 | 5 |
| SNV55 | 21.66 | 6 |
| SNV63 | 21.37 | 7 |
| SNV34 | 17.74 | 8 |
| SNV93 | 17.74 | 8 |
| SNV18 | 11.52 | 9 |
| FSP4_5 | 10.41 | 10 |

Step 3.3: HLA Class-I Binding Prediction (RIC50)

For each SNV or FSP-derived neoantigen peptide, the likelihood of MHC class I binding is defined as the best predicted (lowest) IC50 value among all predicted 9mer epitopes that include the mutated amino acid(s) or include one mutated amino acid from the FSP. Prediction is performed only against the MHC class I alleles present in the patient determined by analysis of the normal DNA sample.

The list of neoantigens is then ordered from the lowest predicted IC50 value (RIC50 score equal to 1) to the highest predicted IC50 value. Neoantigens with the same IC50 value are given the same rank score RIC50 (Table 3).

TABLE 3

Neoantigens with equal IC50 values get the same rank score RIC50

| | IC50 | RIC50 |
|---|---|---|
| SNV67 | 1 | 1 |
| SNV11 | 1.3 | 2 |
| SNV23 | 3.5 | 3 |
| SNV61 | 3.8 | 4 |
| SNV26 | 4.2 | 5 |
| SNV62 | 4.2 | 5 |
| SNV105 | 7.2 | 6 |
| SNV69 | 8.4 | 7 |
| SNV18 | 9.6 | 8 |
| SNV34 | 12.7 | 9 |
| FSP4_5 | 16.4 | 10 |

Step 3.4:

The final prioritization (ranking) of the neoantigens is then done by calculating a weighted sum (RSUM) of the 3 individual rank scores and ranking the neoantigens from lowest to highest RSUM value (FIG. 3). Weighting is applied in the following way:

$$RSUM=(RFREQ+REXPR+(k+RIC50))*WF \qquad \text{Formula (I):}$$

In formula (I) k is a constant value that is added to the RIC50 value in the case the predicted epitope has an IC50 value higher than 1000 nM (this penalizes neoantigens with a high RIC50 score value, i.e. with a high IC50 value).

The value for k is determined in the following way.

$$k = \begin{cases} M = \text{number of candidate neoantigens} & \text{if } MHCI_{IC50\ prediction} > 1000nM \\ 0 & \text{if } MHCI_{IC50\ prediction} \leq 1000nM \end{cases}$$

Occasionally NGS-RNA data, for technical reasons, does not provide coverage at the location of the mutation, neither for the non-mutated amino acids nor for the mutated amino acids in an otherwise expressed gene. WF is a down-weighting factor (down-weighting because the resulting RSUM value is increased and the neoantigen is ranked further down in the list) taking into account cases where no mutated reads were observed in the NGS-RNA transcriptome data.

$$WF = \begin{cases} 1 & mut \text{ reads } RNAseq > 0 \\ 2 & mut \text{ reads } RNAseq = 0;\ wt \text{ reads } RNAseq = 0;\ TPM \geq 0.50 \\ 3 & mut \text{ reads } RNAseq = 0;\ wt \text{ reads } RNAseq > 0;\ TPM \geq 0.50 \\ 4 & mut \text{ reads } RNAseq = 0;\ wt \text{ reads } RNAseq = 0;\ TPM < 0.50 \\ 5 & mut \text{ reads } RNAseq = 0;\ wt \text{ reads } RNAseq > 0;\ TPM < 0.50 \end{cases}$$

This generates a RSUM ranked list of neoantigens.

Neoantigens that have the same RSUM score are further prioritized according to their RIC50 score (FIG. 3). If both the RSUM score and the RIC50 score are identical neoantigens are further prioritized according to their REXPR score. In case the RSUM score, the RIC50 score and the REXPR score are identical neoantigens are further prioritized according to their RFREQ score. In case the RSUM score, the RIC50 score, the REXPR and the RFREQ score are identical neoantigens are further prioritized according to the uncorrected gene-level TPM value.

Step 4:

Step 4.1:

The final list of M ranked neoantigens is then analyzed by a method that determines which and how many neoantigens can be included in the vaccine vector.

Figure 4:
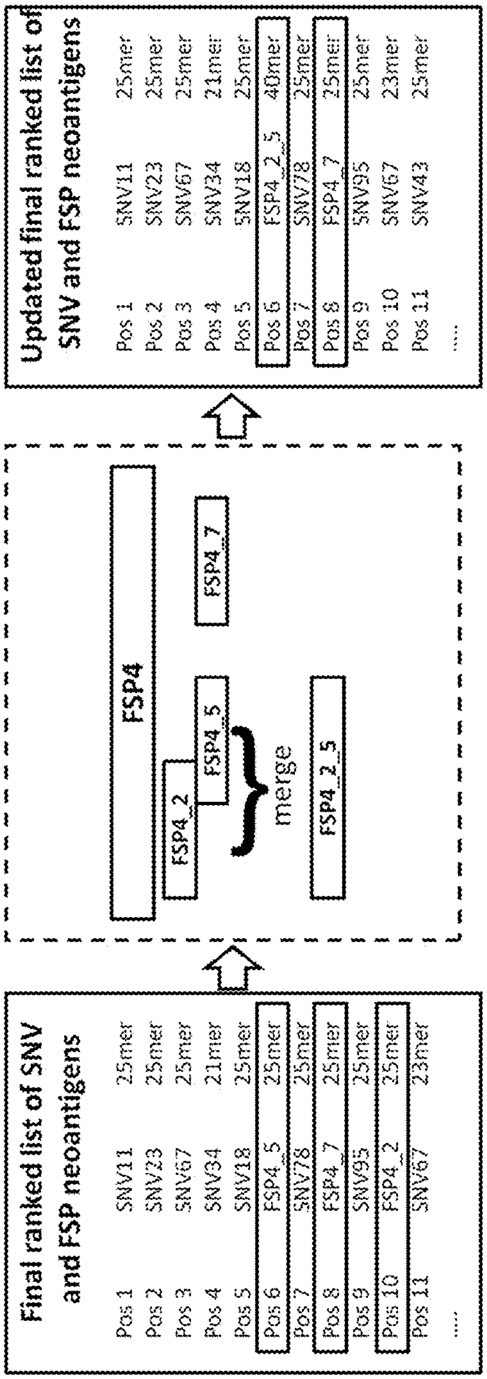

The method works with an iterative procedure. At each iteration a list of the N best ranked neoantigens necessary to reach the maximum insert size of L amino acids (preferably 1500 amino acids) is created. If the list of N neoantigens contains more than one partially overlapping neoantigens derived from the same FSP, a merging step is performed to avoid the inclusion of redundant stretch of the same amino acid sequence. (FIG. 4). If after the merging step, the total length of the included neoantigens still does not reach the maximum desired insert size, a new iteration is performed by adding the next neoantigen from the ranked list.

The procedure stops when adding the next neoantigen to the already selected list of N neoantigens would exceed the maximum desired insert size L.

The precise value of N can therefore decrease due to the presence of merged FSP-derived neoantigens (length longer than a 25mer) or increase due to the presence of neoantigens containing mutations close to the N- or C-terminus of the protein (these neoantigens will be shorter than a 25mer).

Output is a list of N neoantigens with a total length less or equal to L=1500aa.

Step 4.2:

The ordered list is then split into two parts of approximately equal length (FIG. 5). The skilled person is aware that a number of different ways are feasible how to split the list into two parts.

Step 4.3:

The list of N selected neoantigen sequences is then re-ordered according to a method that minimizes the formation of predicted junctional epitopes that may be generated by the juxtaposition of two adjacent neoantigen peptides in an assembled polyneoantigen polypeptide. One million of scrambled layouts of the assembled polyneoantigen are generated each with a different neoantigen order. Each layout is then analyzed to determine the number of predicted junctional epitopes with an IC50<=1500 nM for one of the patient's HLA alleles. While looping over all one million layouts the layout with the minimal number of predicted junctional epitopes encountered up to that point is remembered. If later on a second layout with the same minimal number of predicted junctional epitopes is found the layout first encountered is kept.

Example 2: Application of the Priorization Method to One Existing Literature Dataset The prioritization method described in Example 1 was applied to a NGS dataset from a pancreatic cancer sample (Pat_3942; Tran et al. 2015) for which one experimentally validated immunogenic reactivity has been reported. Tumor/normal exome and the tumor transcriptome NGS raw data were downloaded from the NCBI SRA database [SRA IDs:SRR2636946; SRR2636947; SRR4176783] and analyzed with a pipeline that characterizes the patient's mutanome.

The mutation detection pipeline utilized comprised 8 steps:

a) Quality control and optimization of reads:

Preliminary quality control of the raw sequence data was performed with FastQC 0.11.5 (Andrews, bioinformatics.babraham.ac.uk/projects/fastqc/) Paired reads with length less than 50 bp were filtered out. After visual inspection, the remaining reads were optionally trimmed at the 5' and 3' end using Trimmomatic-0.33 (Bolger et al., 2014) to remove sequenced bases with low quality and to improve the quality of reads suitable (QC-filtered reads) for alignment to the reference genome.

b) Read alignment against the reference genome:

The QC-filtered DNA reads were then aligned against the human reference genome version GRCh38/hg38 by using the BWA-mem algorithm (Li & Durbin, 2009) with default parameters. The QC-filtered RNA reads were aligned using the Hisat2 2.2.0.4 (Kim et al., 2015) software keeping all parameters as default. Read pairs for which only one read was aligned and paired reads that aligned to more than one genomic locus with the same mapping score were filtered out using Samtools 1.4 (Li et al., 2009).

c) Alignment optimization:

DNA read alignments were further processed by a procedure that optimized the local alignment around small insertions or deletions (indels), marked duplicated reads and recalibrated the final base quality score in the realigned regions. Indel realignment was performed using tools RealignerTargetCreator and IndelRealigner from the GATK software version 3.7 (McKenna et al., 2010). Duplicated reads were detected and marked using MarkDuplicates from Picard version 2.12 (broadinstitute.github.io/picard). Base quality score recalibration was performed using BaseRecalibrator and PrintReads of GATK version 3.7 (McKenna et al., 2010). Polymorphisms annotated in the human dbSNP138 release (ncbi.nlm.nih.gov/projects/SNP/snp_summary.cgi?view+summary=view+sum mary&build_id=138) were used as a list of known sites in order to generate the base recalibration model.

d) HLA Determination:

Patient-specific HLA class-I type assessment was performed by aligning the QC-filtered DNA reads from the normal sample on the portion of hg38 genome that encodes the class-I human haplotypes with BWA-mem (Li & Durbin, 2009). Read pairs for which only one read was aligned and read pairs aligned to more than one locus with the same mapping score were filtered out using Samtools 1.4 (Li et al., 2009). Finally, determination of the most likely haplotypes of the patient was performed with the optotype software (Szolek et al., 2014). HLA class-II type assessment was performed by aligning the QC-filtered DNA reads from the normal sample on the portion of hg38 genome that encodes the class-II human haplotypes with BWA-mem (li & Durbin, 2009). Determination of the most likely class-II haplotypes of the patient was performed with the HLAminer software (Warren et al., 2012).

e) Variant Calling:

Somatic variant calling of single nucleotide variants (SNVs) and small indels is performed on the recalibrated DNA read data by mutect2 (Cibulskis et al., 2012) included in GATK version 3.7 [25] and by Varscan2 2.3.9 (Koboldt et al., 2012) by explicitly comparing the tumor sample vs. the normal control sample. All parameters were kept to default. SCALPEL (Fang et al., 2014) with default parameters was used as additional tool for variant calling of indels. Significant somatic variants, detected by at least one of the algorithms, were then mapped onto the human Refseq transcriptome using the Annovar software (Wang et al., 2010) and further filtered. Only SNVs that generate non-synonymous (missense) change in a codon or indels that generate a change of the reading frame within the coding sequence of protein-coding genes (frameshift indels) were retained. SNVs that generate premature stop-codons were excluded. For each detected variant, the number of mutated and wt reads observed in the aligned NGS data from DNA and RNA samples was then determined with a custom tool that utilizes mpileup of Samtools 1.4 (Li et al., 2009).

f) Neoantigen Generation:

Each somatic variant was translated into a peptide containing the mutated amino acid. For SNVs the neoantigen peptides were generated by adding 12 wild type amino acids upstream and downstream of the mutated amino acid. Exceptions in length occurred for 5 mutations for which the mutated amino acid was mapped at less of 12 amino acids of distance from the N-terminal or from the C-terminal. Multiple 25-mer peptides were generated in 3 cases in which a SNV induced an amino acid change in multiple alternative splicing iso forms with distinct protein sequences. For the indels generating FSP were added 12 wild type amino acids upstream to the first new amino acid. Modified FSPs that have a final length of at least nine amino acids were retained.

g) Neoantigens' HLA-I Binding Predictions:

The likelihood of MHC-I binding was determined as the best predicted (lowest) IC50 value among all predicted 9-mer epitopes that include the mutated amino acid(s). Predictions were performed by using the IEDB_recommended method of the IEDB software (Moutaftsi et al., 2006). The netMHCpan (Hoof et al., 2009) method was used in case a MHC-I haplotype was not covered by the IEDB_recommended method (Moutaftsi et al., 2006).

h) Final Selection of Confident Variants:

The initial list of SNVs and indels causing a frameshift was then further reduced by selecting only mutations that fulfil the following criteria:

mutation allele frequency (MF) in the tumor DNA sample>=10% ratio of the MF in the tumor DNA sample and in the control DNA sample>=5 mutated reads at chromosomal position of somatic variant in the tumor DNA>2 mutated reads at chromosomal position of somatic variant in the normal DNA<2

The final list of 129 neoantigen encoding mutations confidently detected in patient Pat_3942 included 4 frameshift generating indels and 125 SNVs. The 125 SNVs generate 128 neoantigens, 3 out of which derived from mutations mapped on multiple alternative splicing isoforms. The 4 frameshift indels generate 4 FSPs with a total length of 307 amino acids and a total of 260 neoantigen sequences. The total length of all 388 neoantigens derived either from SNVs or frameshift indels was 3942 amino acids.

The maximal insert size (including expression control elements) that can be accommodated by genetic vaccines, for example adenoviral vectors, is limited thus imposing a maximal size of L amino acids to the encoded polyneoantigen. Typical values for L for adenoviral vectors are in the order of 1500 amino acids, smaller than the cumulative length of 3942 amino acids for all neoantigens. The prioritization strategy described in Example 1 was therefore applied in order to select an optimal subset of ranked neoantigens compatible with the 3942 amino acid limit Table 4 reports all 60 selected neoantigens selected to reach a cumulative length of 1485 aa. The selection process included 6 neoantigen sequences derived from the FSP chr11:1758971_AC_-(2 nucleotide deletion), 2 neoantigen sequences from the FSP chr6:168310205_-_T (1 nucleotide insertion) and 1 neoantigen sequences from FSP chr163757295_GATAGCTGTAGTAGGCAGCATC_-(22 nucleotide deletion; SEQ ID NO:185). During selection several overlapping FSP-derived neoantigen sequences were merged in order to remove redundant sequence segments (Table 5). Details of the merged neoantigen sequences are shown in FIG. 6.

All neoantigen sequences generated by the 129 confidently detected mutations in Pat_3942 are listed in Table 6 including the associated values of the three parameters (mutant allele frequency MFREQ, corrected expression value corrTPM, best predicted IC50 value for MHC class I 9mer epitopes MIC50), the resulting three independent rank scores (RFREQ, REXPR, RIC50), the weighting factor WF, the weighted RSUM value and the resulting RSUM rank.

Importantly, all three neoantigen sequences reported to induce T-cell reactivity in the patient (Tran et al., 2015) were selected within the top 60 neoantigens by the prioritization strategy.

TABLE 4

List of 60 neoantigens selected for the Pat_3942. Mutated aa in SNV-derived neoantigens are indicated in bold. For FSP-derived neoantigens amino acids that are part of the frameshift peptide are also in bold. Neoantigen sequences with experimentally verified to induce T-cell reactivity are labelled TP in the column "Final Rank" .Genomic coordinates given are with respect to human genome assembly GRch38/hg38.

| ID (COORD; WT; MUT) | SEQ ID NO: | NEO-ANTIGEN | LENGTH | AFREQ | TPM | Corr TPM | BEST PRED. IC50 | RFREQ | REXPR | RIC50 | RSUM | WF | NEOAG RANK | FINAL RANK |
|---|---|---|---|---|---|---|---|---|---|---|---|---|---|---|
| chr17: 74748996_G_C | 12 | YIRLVEPGSPAE**N**AGLLAGDRLVEV | 25 | 0.71 | 53.33 | 46.90 | 269.58 | 6 | 6 | 32 | 44 | 1 | 1 | 1 |
| chr11: 117189364_C_T | 13 | YFWNIATIAVFY**V**LPVVQLVITYQT | 25 | 0.42 | 9.30 | 4.01 | 84.40 | 31 | 35 | 12 | 78 | 1 | 2 | 2 |
| chr14: 22875565_C_T | 14 | VTLEDFYGVFSS**L**GYTHLASVSHPQ | 25 | 0.33 | 88.08 | 37.64 | 12.02 | 71 | 8 | 2 | 81 | 1 | 3 | 3 |
| chr2: 43225254_G_A | 15 | EKCQFAHGFHEL**C**SLTRHPKYKTEL | 25 | 0.38 | 113.35 | 47.53 | 250.90 | 50 | 5 | 31 | 86 | 1 | 4 | 4 |
| chr11: 66492872_C_T | 16 | TPDFTSLDVLTF**V**GSGIPAGINIPN | 25 | 0.40 | 57.51 | 29.72 | 289.70 | 40 | 10 | 36 | 86 | 1 | 5 | 5 |
| chr11: 73975612_C_T | 17 | SAFGAGFCTTVI**T**SPVDWKTRYMN | 25 | 0.42 | 56.16 | 21.37 | 416.00 | 34 | 14 | 40 | 88 | 1 | 6 | 6 |
| chr22: 19355853_G_A | 18 | ESLHSILAGSDM**M**VSQILLTQHGIP | 25 | 0.63 | 12.42 | 11.52 | 795.10 | 12 | 19 | 57 | 88 | 1 | 7 | 7 |
| chr1: 1602925892_T_A | 19 | AMRLLHDQVGVI**L**FGPYKQLFLQTY | 25 | 0.39 | 33.40 | 17.74 | 204.82 | 45 | 15 | 29 | 89 | 1 | 8 | 8 |
| chr8: 226189194_G_C | 20 | APTEHKALVSHN**A**SLINVGSLLQRA | 25 | 0.42 | 56.91 | 26.12 | 487.10 | 33 | 11 | 45 | 89 | 1 | 9 | 9 |
| chr3: 184338462_C_T | 21 | LPRGLSLSSLGS**V**RTLRGWSRSSRP | 25 | 0.38 | 5.70 | 5.70 | 108.60 | 46 | 29 | 18 | 93 | 1 | 10 | 10 |
| chr1: 206732591_C_A | 22 | ERWEDVKEEMTS**D**LATMRVDYEQIK | 25 | 0.37 | 43.68 | 21.66 | 207.98 | 52 | 13 | 30 | 95 | 1 | 11 | 11 |
| chr1: 92843466_G_T | 23 | LYSCIALKVTAN**K**MEMEHSLILNNL | 25 | 0.72 | 3.15 | 3.15 | 761.20 | 4 | 37 | 56 | 97 | 1 | 12 | 12 |

TABLE 4-continued

List of 60 neoantigens selected for the Pat_3942. Mutated aa in SNV-derived neoantigens are indicated in bold. For FSP-derived neoantigens amino acids that are part of the frameshift peptide are also in bold. Neoantigen sequences with experimentally verified to induce T-cell reactivity are labelled TP in the column "Final Rank" .Genomic coordinates given are with respect to human genome assembly GRch38/hg38.

| ID (COORD; WT; MUT) | SEQ ID NO: | NEO-ANTIGEN | LENGTH | AFREQ | TPM | Corr TPM | BEST PRED. IC50 | RFREQ | REXPR | RIC50 | RSUM | WF | NEOAG RANK | FINAL RANK |
|---|---|---|---|---|---|---|---|---|---|---|---|---|---|---|
| chr6: 137200930_T_C | 24 | LVLSLVFICFYI**R**KINPLKEKSIIL | 25 | 0.37 | 24.54 | 10.41 | 183.20 | 54 | 21 | 25 | 100 | 1 | 13 | 13 |
| chrX: 53192998_C_T | 25 | PFSTLTPRLHLP**Y**PQQPPQQQL | 22 | 0.33 | 26.41 | 9.15 | 48.58 | 70 | 25 | 7 | 102 | 1 | 14 | 14 |
| chr14: 71685616_G_A | 26 | AANIPRSISSDG**H**PLERRLSPGSDI | 25 | 0.40 | 7.69 | 5.78 | 683.30 | 37 | 28 | 52 | 117 | 1 | 15 | 15 |
| chr8: 70734206_T_A | 27 | YYIVRVLGTLGI**M**TVFWVCPLTIFN | 25 | 0.35 | 1.02 | 0.82 | 31.80 | 65 | 53 | 6 | 124 | 1 | 16 | 16 |
| chr13: 23760177_G_C | 28 | WQLRFSHLVGYG**G**RYYSYLMSRAVA | 25 | 0.24 | 28.04 | 9.87 | 17.86 | 98 | 23 | 4 | 125 | 1 | 17 | 17 |
| chr1: 237783918_G_C | 29 | HYTQSETEFLLS**S**AETDENETLDYE | 25 | 0.44 | 0.88 | 0.46 | 483.56 | 24 | 61 | 44 | 129 | 1 | 18 | 18 |
| chr2: 156568935_G_A | 30 | QSISRNHVVDIS**K**SGLITIAGGKWT | 25 | 0.37 | 10.33 | 10.33 | 930.40 | 54 | 22 | 65 | 141 | 1 | 19 | 19 TP |
| chr2: 203049917_G_C | 31 | LLQCVQKMADGL**Q**EQQQALSILLVK | 25 | 0.31 | 5.52 | 2.27 | 181.12 | 77 | 43 | 24 | 144 | 1 | 20 | 20 |
| chr11: 3762912_G_T | 32 | TGLFGQTNTGFG**D**VGSTLFGNNKLT | 25 | 0.28 | 12.56 | 5.48 | 184.10 | 88 | 30 | 27 | 145 | 1 | 21 | 21 TP |
| chr7: 6041002_A_T | 33 | LQENGLAGLSAS**T**IVEQQLPLRRNS | 25 | 0.28 | 43.46 | 24.50 | 559.50 | 88 | 12 | 49 | 149 | 1 | 22 | 22 |
| chr11: 1758971_AC_— | 34 | GSLSGYLSQDTV**GALPVSVVSLCPGRCQSG** | 30 | 0.31 | 460.80 | 2.03 | 279; 1126.6; 1161.9; 1694.6 | 79 | 44 | 34 | 157 | 1 | 23; 52; 53; 59 | 23 |
| chr18: 8244173_T_G | 35 | SYAEQGTNCDEAVSFMDTHNLNGRS | 25 | 0.64 | 0.89 | 0.89 | 131.70 | 9 | 52 | 20 | 162 | 2 | 24 | 24 |
| chr7: 120953341_C_G | 36 | NAMDQLEQRVSE**L**FMNAKKNKPEWR | 25 | 0.33 | 4.53 | 2.80 | 795.92 | 72 | 39 | 58 | 169 | 1 | 25 | 25 |

TABLE 4-continued

List of 60 neoantigens selected for the Pat_3942. Mutated aa in SNV-derived neoantigens are indicated in bold. For FSP-derived neoantigens amino acids that are part of the frameshift peptide are also in bold. Neoantigen sequences with experimentally verified to induce T-cell reactivity are labelled TP in the column "Final Rank" .Genomic coordinates given are with respect to human genome assembly GRch38/hg38.

| ID (COORD; WT; MUT) | SEQ ID NO: | NEO-ANTIGEN | LENGTH | AFREQ | TPM | Corr TPM | BEST PRED. IC50 | RFREQ | REXPR | RIC50 | RSUM | WF | NEOAG RANK | FINAL RANK |
|---|---|---|---|---|---|---|---|---|---|---|---|---|---|---|
| chr7:100866373_A_G | 37 | GDAEAEALARSA**S**ALVRAQQGRGTG | 25 | 0.29 | 28.56 | 12.60 | 944.20 | 87 | 17 | 67 | 171 | 1 | 26 | 26 |
| chr9:108931129_T_A | 38 | MRNLK**F**FRTLEFRDIQGP | 18 | 0.45 | 6.22 | 6.22 | 419.90 | 21 | 27 | 41 | 178 | 2 | 27 | 27 |
| chr6:168310205_—_T | 39 | ARPPGSVEDAGQ**AVGHILAQACVYRAVQCSR** | 31 | 0.27 | 2.65 | 1.34 | 391.51; 841.6 | 92 | 48 | 38 | 178 | 1 | 28; 31 | 28 |
| chr11:1758971_AC_— | 40 | **PEHLLLLPEQGPRCAAWG** | 18 | 0.31 | 460.80 | 2.03 | 833.33 | 79 | 44 | 60 | 183 | 1 | 29 | 29 |
| chr3:78661237_G_T | 41 | VHWTVDQQSQYI**K**GYKILYRPSGAN | 25 | 0.41 | 0.77 | 0.77 | 15.81 | 36 | 54 | 3 | 186 | 2 | 30 | 30 |
| chr7:100958504_C_T | 42 | ETTSHSTPGFTS**L**ITTTETTSHSTP | 25 | 0.23 | 9.63 | 9.63 | 104.10 | 101 | 24 | 16 | 280 | 2 | 32 | 31 |
| chr4:185593889_T_A | 43 | PVFTHENIQGGG**V**PFQALYNYTPRN | 25 | 0.67 | 0.77 | 0.07 | 50.32 | 7 | 83 | 8 | 294 | 3 | 33 | 32 |
| chrX:3321328_T_G | 44 | TTLSSIKVEVAS**R**QAETTTLDQDHL | 25 | 0.43 | 0.75 | 0.75 | 937.87 | 27 | 56 | 66 | 298 | 2 | 34 | 33 |
| chr16:3757295_GATAGCTGTAGTAGGCAGCATC_— | 45 | CCYGKQLCTIPR**RIGIISVRSVSQ** | 24 | 0.13 | 4.88 | 4.88 | 689.40 | 102 | 33 | 53 | 376 | 2 | 35 | 34 |
| chr1:237591836_T_A | 46 | DVLADDRDDYDF**M**MQTSTYYYSVRI | 25 | 0.37 | 0.88 | 0.08 | 2.77 | 57 | 80 | 1 | 414 | 3 | 36 | 35 |
| chr16:3597422_G_A | 47 | ALTGAWAMEDFY**M**ARLVPPLVPQRP | 25 | 0.33 | 1.15 | 0.10 | 22.00 | 73 | 77 | 5 | 465 | 3 | 37 | 36 |
| chr6:49733209_G_C | 48 | CPNQKVLKYYYV**W**QYCPAGNWANRL | 25 | 0.50 | 0.03 | 0.03 | 100.85 | 17 | 92 | 15 | 496 | 4 | 38 | 37 |
| chr13:24222901_G_T | 49 | QDGIPGDEGLEL**L**SADSAVPVAMTQ | 25 | 0.25 | 5.20 | 0.25 | 53.80 | 97 | 66 | 9 | 516 | 3 | 39 | 38 |

TABLE 4-continued

List of 60 neoantigens selected for the Pat_3942. Mutated aa in SNV-derived neoantigens are indicated in bold. For FSP-derived neoantigens amino acids that are part of the frameshift peptide are also in bold. Neoantigen sequences with experimentally verified to induce T-cell reactivity are labelled TP in the column "Final Rank" .Genomic coordinates given are with respect to human genome assembly GRch38/hg38.

| ID (COORD; WT; MUT) | SEQ ID NO: | NEO-ANTIGEN | LENGTH | AFREQ | TPM | Corr TPM | BEST PRED. IC50 | RFREQ | REXPR | RIC50 | RSUM | WF | NEOAG RANK | FINAL RANK |
|---|---|---|---|---|---|---|---|---|---|---|---|---|---|---|
| chr2: 700880 42_T_A | 50 | TNSTAAS RPPVT**Q** RLVVPAT QCGSL | 25 | 0.43 | 472.90 | 166.15 | 2115.34 | 28 | 2 | 500 | 530 | 1 | 40 | 39 |
| chr13: 106559 614_C_A | 51 | QEIEEKL IEEET**L** RRVEELV AKRVE | 25 | 0.375 | 68.76 | 31.79 | 1381.75 | 51 | 9 | 476 | 536 | 1 | 41 | 40 |
| chr15: 101686 041_A_T | 52 | TDFIREE YHKRD**I** TEVLSPN MYNSK | 25 | 0.61 | 1.82 | 1.82 | 1618.50 | 13 | 46 | 480 | 539 | 1 | 42 | 41 |
| chr16: 65003_ G_A | 53 | MSEA**C** RDSTSSL QRKKP | 17 | 0.35 | 27.87 | 16.09 | 1144.35 | 62 | 16 | 466 | 544 | 1 | 43 | 42 |
| chr17: 635835 26_G_A | 54 | HDKEVYD IAFSR**T** GGGRDMF ASVGA | 25 | 0.71 | 11.87 | 11.87 | 3393.50 | 5 | 18 | 526 | 549 | 1 | 44 | 43 |
| chr6: 876059 25_G_A | 55 | EIPTAAL VLG**V**NI TDHDLTF GSLTE | 25 | 0.35 | 13.08 | 8.86 | 1039.10 | 65 | 26 | 461 | 552 | 1 | 45 | 44 |
| chr16: 252401 54_C_T chr17: | 56 | SSLIIHQ RTHTG**K** KPYQCGE CGKSF | 25 | 0.47 | 0.43 | 0.43 | 1629.60 | 19 | 62 | 482 | 563 | 1 | 46 | 45 |
| 767380 3_G_A | 57 | SGNLLGR NSFEV**C** VCACPGR DRRTE | 25 | 0.73 | 43.46 | 43.46 | 4847.50 | 3 | 7 | 553 | 563 | 1 | 47 | 46 |
| chr6: 730419 54_G_A | 58 | SCLLILE FVMIV**I** FGLEFII RIWSA | 25 | 0.43 | 0.01 | 0.01 | 75.89 | 28 | 103 | 10 | 564 | 4 | 48 | 47 |
| chr19: 127533 03_G_C | 59 | LTEGQKR YFEKL**L** IYCDQYA SLIPV | 25 | 0.38 | 0.07 | 0.07 | 83.74 | 48 | 82 | 11 | 564 | 4 | 49 | 48 |
| chr6: 307444 39_G_A | 60 | QAPTPAP STIPG**L** RRGSGPE IFTFD | 25 | 0.45 | 1190.79 | 550.66 | 4742.67 | 22 | 1 | 549 | 572 | 1 | 50 | 49 |
| chr1: 110603 966_C_G | 61 | VAIIPYF ITLGT**Q** LAEKPED AQQGQ | 25 | 0.63 | 0.02 | 0.02 | 357.40 | 11 | 96 | 37 | 576 | 4 | 51 | 50 |
| chr11: 175897 1_AC_— | 62 | **PGHGLPP HLRQQR AARLRQP DAAEA** | 25 | 0.31 | 460.80 | 2.03 | 1202.07 | 79 | 44 | 468 | 591 | 1 | 54 | 51 |
| chr7: 991737 80_G_C | 63 | IIEKHFG EEEDE**R** QTLLSQV IDQDY | 25 | 0.38 | 2.82 | 1.00 | 2045.92 | 48 | 51 | 498 | 597 | 1 | 55 | 52 TP |

TABLE 4-continued

List of 60 neoantigens selected for the Pat_3942. Mutated aa in SNV-derived neoantigens are indicated in bold. For FSP-derived neoantigens amino acids that are part of the frameshift peptide are also in bold. Neoantigen sequences with experimentally verified to induce T-cell reactivity are labelled TP in the column "Final Rank" .Genomic coordinates given are with respect to human genome assembly GRch38/hg38.

| ID (COORD; WT; MUT) | SEQ ID NO: | NEO-ANTIGEN | LENGTH | AFREQ | TPM | Corr TPM | BEST PRED. IC50 | RFREQ | REXPR | RIC50 | RSUM | WF | NEOAG RANK | FINAL RANK |
|---|---|---|---|---|---|---|---|---|---|---|---|---|---|---|
| chr16:75631789_C_G | 64 | YEIGRQFRNEGI**H**LTHNPEFTTCEF | 25 | 0.37 | 150.39 | 71.89 | 4282.32 | 56 | 3 | 542 | 601 | 1 | 56 | 53 |
| chr2:202961406_G_A | 65 | RLMWKSQYVPYD**E**IPFVNAGSRAVV | 25 | 0.31 | 0.73 | 0.03 | 281.00 | 76 | 91 | 35 | 606 | 3 | 57 | 54 |
| chr9:113176616_C_T | 66 | QAQSKFKSEKQN**Q**KQLELKVTSLEE | 25 | 0.35 | 13.35 | 5.38 | 2391.60 | 67 | 31 | 508 | 606 | 1 | 58 | 55 |
| chr12:122986679_G_C | 67 | SFCDGLVHDPLR**Q**KANFLKLLISEL | 25 | 0.42 | 2.27 | 1.19 | 3437.40 | 33 | 49 | 527 | 609 | 1 | 60 | 56 |
| chr9:127953924_C_T | 68 | LDGGDFVSLSSR**K**EVQENCVRWRKR | 25 | 0.38 | 18.72 | 4.24 | 3526.80 | 50 | 34 | 532 | 616 | 1 | 61 | 57 |
| chr3:154427638_G_A | 69 | QSLPLETFSFLL**I**LLATTVTPVFVL | 25 | 0.75 | 0.00 | 0.00 | 502.77 | 1 | 107 | 47 | 620 | 4 | 62 | 58 |
| chr7:45648683_G_A | 70 | GKFDELATENHC**H**RIKILGDCYYCV | 25 | 0.35 | 0.13 | 0.13 | 2006.53 | 63 | 72 | 493 | 628 | 1 | 63 | 59 |
| chr20:35954142_G_A | 71 | VGSSLPEASPPA**L**EPSSPNAAVPEA | 25 | 0.26 | 169.84 | 50.85 | 3489.10 | 96 | 4 | 531 | 631 | 1 | 64 | 60 |

TABLE 5

Merged FSP-derived neoantigens for Pat_3492. Amino acids that are part of the frameshift peptide (mutated amino acids) are indicated in bold. Genomic coordinates given are with respect to human genome assembly GRch38/hg38.

| ID | Merged FSP (SEQ ID NO) | Final rank | NEOAG PEPTIDE | AFREQ | TPM | Corr TPM | BEST PRED. IC50 | RFREQ | REXPR | RIC50 | RSUM | WF | NEOAG RANK |
|---|---|---|---|---|---|---|---|---|---|---|---|---|---|
| chr11:1758971_AC_— | GSLSGYLSQDTV**GALPVSVVSLCPGRCQSG** (SEQ ID NO: 72) | 23 | GSLSGYLSQDTV**GALPVSVVSLC** (SEQ ID NO: 73) | 0.31 | 460.8 | 2.03 | 279 | 79 | 44 | 34 | 157 | 1 | 23 |
| chr11:1758971_AC_— | | | **YLSQDTVGALPVSVVSLCPGRCQSG** (SEQ ID NO: 74) | 0.31 | 460.8 | 2.03 | 1126.6 | 79 | 44 | 465 | 588 | 1 | 52 |

TABLE 5-continued

Merged FSP-derived neoantigens for Pat_3492. Amino acids that are part of the frameshift peptide (mutated amino acids) are indicated in bold. Genomic coordinates given are with respect to human genome assembly GRch38/hg38.

| ID | Merged FSP (SEQ ID NO) | Final rank | NEOAG PEPTIDE | AFREQ | TPM | Corr TPM | BEST PRED. IC50 | RFREQ | REXPR | RIC50 | RSUM | WF | NEOAG RANK |
|---|---|---|---|---|---|---|---|---|---|---|---|---|---|
| chr11:1758971_AC_— | | | **LSGYLSQDTVGALPVSVVSLCPGRC** (SEQ ID NO: 75) | 0.31 | 460.8 | 2.03 | 1161.9 | 79 | 44 | 467 | 590 | 1 | 53 |
| chr11:1758971_AC_— | | | **SGYLSQDTVGALPVSVVSLCPGRCQ** (SEQ ID NO: 76) | 0.31 | 460.8 | 2.03 | 1694.6 | 79 | 44 | 483 | 606 | 1 | 59 |
| chr6:16831020 5_—_T | ARPPGSVEDAGQ**AVGHILAQACVYRAVQCSR** (SEQ ID NO: 77) | 28 | ARPPGSVEDAG**QAVGHILAQAC** (SEQ ID NO: 78) | 0.27 | 2.65 | 1.34 | 841.6 | 92 | 48 | 61 | 201 | 1 | 31 |
| chr6:16831020 5_—_T | | | EDAGQA**VGHILAQACVYRAVQCSR** (SEQ ID NO: 79) | 0.27 | 2.65 | 1.34 | 381.51 | 92 | 48 | 38 | 178 | 1 | 28 |

TABLE 6

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr17:74748996_G_C | SNV | 0.71 | 53.33 | 46.90 | 269.58 | 6 | 6 | 32 | 44 | 1 | 1 |
| chr11:117189364_C_T | SNV | 0.42 | 9.30 | 4.01 | 84.40 | 31 | 35 | 12 | 78 | 1 | 2 |
| chr14:22875565_C_T | SNV | 0.33 | 88.08 | 37.64 | 12.02 | 71 | 8 | 2 | 81 | 1 | 3 |
| chr2:43225254_G_A | SNV | 0.38 | 113.35 | 47.53 | 250.90 | 50 | 5 | 31 | 86 | 1 | 4 |
| chr11:66492872_C_T | SNV | 0.40 | 57.51 | 29.72 | 289.70 | 40 | 10 | 36 | 86 | 1 | 5 |
| chr11:73975612_C_T | SNV | 0.42 | 56.16 | 21.37 | 416.00 | 34 | 14 | 40 | 88 | 1 | 6 |
| chr22:19355853_G_A | SNV | 0.63 | 12.42 | 11.52 | 795.10 | 12 | 19 | 57 | 88 | 1 | 7 |
| chr1:160292592_T_A | SNV | 0.39 | 33.40 | 17.74 | 204.82 | 45 | 15 | 29 | 89 | 1 | 8 |
| chr8:22618914_G_C | SNV | 0.42 | 56.91 | 26.12 | 487.10 | 33 | 11 | 45 | 89 | 1 | 9 |
| chr3:184338462_C_T | SNV | 0.38 | 5.70 | 5.70 | 108.60 | 46 | 29 | 18 | 93 | 1 | 10 |
| chr1:206732591_C_A | SNV | 0.37 | 43.68 | 21.66 | 207.98 | 52 | 13 | 30 | 95 | 1 | 11 |
| chr1:92843466_G_T | SNV | 0.72 | 3.15 | 3.15 | 761.20 | 4 | 37 | 56 | 97 | 1 | 12 |
| chr6:137200930_T_C | SNV | 0.37 | 24.54 | 10.41 | 183.20 | 54 | 21 | 25 | 100 | 1 | 13 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chrX:53192998_C_T | SNV | 0.33 | 26.41 | 9.15 | 48.58 | 70 | 25 | 7 | 102 | 1 | 14 |
| chr14:71685616_G_A | SNV | 0.40 | 7.69 | 5.78 | 683.30 | 37 | 28 | 52 | 117 | 1 | 15 |
| chr8:70734206_T_A | SNV | 0.35 | 1.02 | 0.82 | 31.80 | 65 | 53 | 6 | 124 | 1 | 16 |
| chr13:23760177_G_C | SNV | 0.24 | 28.04 | 9.87 | 17.86 | 98 | 23 | 4 | 125 | 1 | 17 |
| chr1:237783918_G_C | SNV | 0.44 | 0.88 | 0.46 | 483.56 | 24 | 61 | 44 | 129 | 1 | 18 |
| chr2:156568935_G_A | SNV | 0.37 | 10.33 | 10.33 | 930.40 | 54 | 22 | 65 | 141 | 1 | 19 |
| chr2:203049917_G_C | SNV | 0.31 | 5.52 | 2.27 | 181.12 | 77 | 43 | 24 | 144 | 1 | 20 |
| chr11:3762912_G_T | SNV | 0.28 | 12.56 | 5.48 | 184.10 | 88 | 30 | 27 | 145 | 1 | 21 |
| chr7:6041002_A_T | SNV | 0.28 | 43.46 | 24.50 | 559.50 | 88 | 12 | 49 | 149 | 1 | 22 |
| chr11:1758971_AC_— | FSP | 0.31 | 460.80 | 2.03 | 279.00 | 79 | 44 | 34 | 157 | 1 | 23 |
| chr18:8244173_T_G | SNV | 0.64 | 0.89 | 0.89 | 131.70 | 9 | 52 | 20 | 162 | 2 | 24 |
| chr7:120953341_C_G | SNV | 0.33 | 4.53 | 2.80 | 795.92 | 72 | 39 | 58 | 169 | 1 | 25 |
| chr7:100866373_A_G | SNV | 0.29 | 28.56 | 12.60 | 944.20 | 87 | 17 | 67 | 171 | 1 | 26 |
| chr9:108931129_T_A | SNV | 0.45 | 6.22 | 6.22 | 419.90 | 21 | 27 | 41 | 178 | 2 | 27 |
| chr6:168310205_—_T | FSP | 0.27 | 2.65 | 1.34 | 391.51 | 92 | 48 | 38 | 178 | 1 | 28 |
| chr11:1758971_AC_— | FSP | 0.31 | 460.80 | 2.03 | 833.33 | 79 | 44 | 60 | 183 | 1 | 29 |
| chr3:78661237_G_T | SNV | 0.41 | 0.77 | 0.77 | 15.81 | 36 | 54 | 3 | 186 | 2 | 30 |
| chr6:168310205_—_T | FSP | 0.27 | 2.65 | 1.34 | 841.60 | 92 | 48 | 61 | 201 | 1 | 31 |
| chr7:100958504_C_T | SNV | 0.23 | 9.63 | 9.63 | 104.10 | 100 | 24 | 16 | 280 | 2 | 32 |
| chr4:185593889_T_A | SNV | 0.67 | 0.77 | 0.07 | 50.32 | 7 | 83 | 8 | 294 | 3 | 33 |
| chrX:3321328_T_G | SNV | 0.43 | 0.75 | 0.75 | 937.87 | 27 | 56 | 66 | 298 | 2 | 34 |
| chr16:3757295_GATATGTAGTAGGCAGCATGCC_— | FSP | 0.13 | 4.88 | 4.88 | 689.40 | 102 | 33 | 53 | 376 | 2 | 35 |
| chr1:237591836_T_A | SNV | 0.37 | 0.88 | 0.08 | 2.77 | 57 | 80 | 1 | 414 | 3 | 36 |
| chr16:3597422_G_A | SNV | 0.33 | 1.15 | 0.10 | 22.00 | 73 | 77 | 5 | 465 | 3 | 37 |
| chr6:49733209_G_C | SNV | 0.50 | 0.03 | 0.03 | 100.85 | 17 | 92 | 15 | 496 | 4 | 38 |
| chr13:24222901_G_T | SNV | 0.25 | 5.20 | 0.25 | 53.80 | 97 | 66 | 9 | 516 | 3 | 39 |
| chr2:70088042_T_A | SNV | 0.43 | 372.90 | 166.15 | 2115.34 | 28 | 2 | 500 | 530 | 1 | 40 |
| chr13:106559613_G_A | SNV | 375.00 | 68.76 | 31.79 | 1381.75 | 51 | 9 | 476 | 536 | 1 | 41 |
| chr15:101686041_A_T | SNV | 0.61 | 1.82 | 1.82 | 1618.50 | 13 | 46 | 480 | 539 | 1 | 42 |
| chr16:65003_G_A | SNV | 0.35 | 27.87 | 16.09 | 1144.35 | 62 | 16 | 466 | 544 | 1 | 43 |
| chr17:63583526_G_A | SNV | 0.71 | 11.87 | 11.87 | 3393.50 | 5 | 18 | 526 | 549 | 1 | 44 |
| chr6:87605925_G_A | SNV | 0.35 | 13.08 | 8.86 | 1039.10 | 65 | 26 | 461 | 552 | 1 | 45 |
| chr16:25240154_C_T | SNV | 0.47 | 0.43 | 0.43 | 1629.60 | 19 | 62 | 482 | 563 | 1 | 46 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr17:7673803_G_A | SNV | 0.73 | 43.46 | 43.46 | 4847.50 | 3 | 7 | 553 | 563 | 1 | 47 |
| chr6:73041954_G_A | SNV | 0.43 | 0.01 | 0.01 | 75.89 | 28 | 103 | 10 | 564 | 4 | 48 |
| chr19:12753303_G_C | SNV | 0.38 | 0.07 | 0.07 | 83.74 | 48 | 82 | 11 | 564 | 4 | 49 |
| chr6:30744439_G_A | SNV | 0.45 | 1190.79 | 550.66 | 4742.67 | 22 | 1 | 549 | 572 | 1 | 50 |
| chr1:110603966_C_G | SNV | 0.63 | 0.02 | 0.02 | 357.40 | 11 | 96 | 37 | 576 | 4 | 51 |
| chr11:1758971_AC_— | FSP | 0.31 | 460.80 | 2.03 | 1126.60 | 79 | 44 | 465 | 588 | 1 | 52 |
| chr11:1758971_AC_— | FSP | 0.31 | 460.80 | 2.03 | 1161.90 | 79 | 44 | 467 | 590 | 1 | 53 |
| chr11:1758971_AC_— | FSP | 0.31 | 460.80 | 2.03 | 1202.07 | 79 | 44 | 468 | 591 | 1 | 54 |
| chr7:99173780_G_C | SNV | 0.38 | 2.82 | 1.00 | 2045.92 | 48 | 51 | 498 | 597 | 1 | 55 |
| chr16:75631789_C_G | SNV | 0.37 | 150.39 | 71.89 | 4282.32 | 56 | 3 | 542 | 601 | 1 | 56 |
| chr2:202961406_G_A | SNV | 0.31 | 0.73 | 0.03 | 281.00 | 76 | 91 | 35 | 606 | 3 | 57 |
| chr9:113176616_C_T | SNV | 0.35 | 13.35 | 5.38 | 2391.60 | 67 | 31 | 508 | 606 | 1 | 58 |
| chr11:1758971_AC_— | FSP | 0.31 | 460.80 | 2.03 | 1694.60 | 79 | 44 | 483 | 606 | 1 | 59 |
| chr12:12298667 9_G_C | SNV | 0.42 | 2.27 | 1.19 | 3437.40 | 33 | 49 | 527 | 609 | 1 | 60 |
| chr9:127953924_C_T | SNV | 0.38 | 18.72 | 4.24 | 3526.80 | 50 | 34 | 532 | 616 | 1 | 61 |
| chr3:154427638_G_A | SNV | 0.75 | 0.00 | 0.00 | 502.77 | 1 | 107 | 47 | 620 | 4 | 62 |
| chr7:45648683_G_A | SNV | 0.35 | 0.13 | 0.13 | 2006.53 | 63 | 72 | 493 | 628 | 1 | 63 |
| chr20:35954142_G_A | SNV | 0.26 | 169.84 | 50.85 | 3489.10 | 96 | 4 | 531 | 631 | 1 | 64 |
| chr11:1758971_AC_— | FSP | 0.31 | 460.80 | 2.03 | 2532.96 | 79 | 44 | 510 | 633 | 1 | 65 |
| chr11:1758971_AC_— | FSP | 0.31 | 460.80 | 2.03 | 2839.18 | 79 | 44 | 513 | 636 | 1 | 66 |
| chr14:10514734 6_G_A | SNV | 0.27 | 25.00 | 10.81 | 3223.39 | 95 | 20 | 523 | 638 | 1 | 67 |
| chr1:50195710_G_T | SNV | 0.37 | 0.06 | 0.06 | 141.47 | 53 | 85 | 22 | 640 | 4 | 68 |
| chr10:7172643_C_G | SNV | 375.00 | 0.22 | 0.22 | 466.80 | 51 | 67 | 42 | 640 | 4 | 69 |
| chr11:1758971_AC_— | FSP | 0.31 | 460.80 | 2.03 | 3107.70 | 79 | 44 | 517 | 640 | 1 | 70 |
| chr11:1758971_AC_— | FSP | 0.31 | 460.80 | 2.03 | 3108.98 | 79 | 44 | 518 | 641 | 1 | 71 |
| chr11:1758971_AC_— | FSP | 0.31 | 460.80 | 2.03 | 3214.82 | 79 | 44 | 522 | 645 | 1 | 72 |
| chr6:168310205_—_T | FSP | 0.27 | 2.65 | 1.34 | 2289.13 | 92 | 48 | 505 | 645 | 1 | 73 |
| chr11:1758971_AC_— | FSP | 0.31 | 460.80 | 2.03 | 3653.37 | 79 | 44 | 533 | 656 | 1 | 74 |
| chr11:1758971_AC_— | FSP | 0.31 | 460.80 | 2.03 | 3971.20 | 79 | 44 | 538 | 661 | 1 | 75 |
| chr11:1758971_AC_— | FSP | 0.31 | 460.80 | 2.03 | 4165.90 | 79 | 44 | 540 | 663 | 1 | 76 |
| chr6:168310205_—_T | FSP | 0.27 | 2.65 | 1.34 | 3305.80 | 92 | 48 | 524 | 664 | 1 | 77 |
| chr11:1758971_AC_— | FSP | 0.31 | 460.80 | 2.03 | 4356.25 | 79 | 44 | 545 | 668 | 1 | 78 |
| chr6:168310205_—_T | FSP | 0.27 | 2.65 | 1.34 | 3463.60 | 92 | 48 | 529 | 669 | 1 | 79 |
| chr19:15238949_C_T | SNV | 0.37 | 11.00 | 5.09 | 6845.76 | 58 | 32 | 580 | 670 | 1 | 80 |
| chr11:1758971_AC_— | FSP | 0.31 | 460.80 | 2.03 | 4759.12 | 79 | 44 | 550 | 673 | 1 | 81 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr11:1758971_AC_— | FSP | 0.31 | 460.80 | 2.03 | 4946.07 | 79 | 44 | 554 | 677 | 1 | 82 |
| chr6:125081449_C_A | SNV | 0.47 | 0.13 | 0.01 | 89.20 | 19 | 104 | 13 | 680 | 5 | 83 |
| chr11:56642316_T_C | SNV | 0.31 | 0.16 | 0.16 | 138.80 | 78 | 71 | 21 | 680 | 4 | 84 |
| chr11:1758971_AC_— | FSP | 0.31 | 460.80 | 2.03 | 5336.03 | 79 | 44 | 558 | 681 | 1 | 85 |
| chr11:1758971_AC_— | FSP | 0.31 | 460.80 | 2.03 | 6066.90 | 79 | 44 | 567 | 690 | 1 | 86 |
| chr11:1758971_AC_— | FSP | 0.31 | 460.80 | 2.03 | 6138.94 | 79 | 44 | 569 | 692 | 1 | 87 |
| chr6:168310205_—_T | FSP | 0.27 | 2.65 | 1.34 | 4806.94 | 92 | 48 | 552 | 692 | 1 | 88 |
| chr11:1758971_AC_— | FSP | 0.31 | 460.80 | 2.03 | 6399.44 | 79 | 44 | 576 | 699 | 1 | 89 |
| chr9:35396877_G_C | SNV | 0.32 | 8.21 | 1.43 | 7055.49 | 75 | 47 | 584 | 706 | 1 | 90 |
| chr11:1758971_AC_— | FSP | 0.31 | 460.80 | 2.03 | 7057.30 | 79 | 44 | 585 | 708 | 1 | 91 |
| chr11:1758971_AC_— | FSP | 0.31 | 460.80 | 2.03 | 7128.50 | 79 | 44 | 587 | 710 | 1 | 92 |
| chr12:100142632_C_T | SNV | 0.37 | 2.69 | 2.69 | 10099.80 | 56 | 41 | 617 | 714 | 1 | 93 |
| chr9:72245167_G_T | SNV | 0.27 | 3.02 | 1.03 | 6183.34 | 93 | 50 | 572 | 715 | 1 | 94 |
| chr9:72245168_A_T | SNV | 0.27 | 3.02 | 1.03 | 6183.34 | 93 | 50 | 572 | 715 | 1 | 95 |
| chr11:1758971_AC_— | FSP | 0.31 | 460.80 | 2.03 | 8182.38 | 79 | 44 | 595 | 718 | 1 | 96 |
| chr11:1758971_AC_— | FSP | 0.31 | 460.80 | 2.03 | 8737.40 | 79 | 44 | 600 | 723 | 1 | 97 |
| chr11:1758971_AC_— | FSP | 0.31 | 460.80 | 2.03 | 9175.65 | 79 | 44 | 608 | 731 | 1 | 98 |
| chr6:168310205_—_T | FSP | 0.27 | 2.65 | 1.34 | 8785.58 | 92 | 48 | 601 | 741 | 1 | 99 |
| chr11:1758971_AC_— | FSP | 0.31 | 460.80 | 2.03 | 10356.18 | 79 | 44 | 619 | 742 | 1 | 100 |
| chr11:1758971_AC_— | FSP | 0.31 | 460.80 | 2.03 | 10624.37 | 79 | 44 | 622 | 745 | 1 | 101 |
| chr9:104504822_T_C | SNV | 0.38 | 0.08 | 0.08 | 822.70 | 47 | 81 | 59 | 748 | 4 | 102 |
| chr11:1758971_AC_— | FSP | 0.31 | 460.80 | 2.03 | 10920.75 | 79 | 44 | 627 | 750 | 1 | 103 |
| chr6:168310205_—_T | FSP | 0.27 | 2.65 | 1.34 | 9878.80 | 92 | 48 | 613 | 753 | 1 | 104 |
| chr2:23758023_T_A | SNV | 0.30 | 0.64 | 0.64 | 9976.94 | 82 | 57 | 616 | 755 | 1 | 105 |
| chr11:1758971_AC_— | FSP | 0.31 | 460.80 | 2.03 | 11571.94 | 79 | 44 | 632 | 755 | 1 | 106 |
| chr11:1758971_AC_— | FSP | 0.31 | 460.80 | 2.03 | 11865.32 | 79 | 44 | 639 | 762 | 1 | 107 |
| chr11:1758971_AC_— | FSP | 0.31 | 460.80 | 2.03 | 11993.50 | 79 | 44 | 640 | 763 | 1 | 108 |
| chr11:1758971_AC_— | FSP | 0.31 | 460.80 | 2.03 | 12302.10 | 79 | 44 | 644 | 767 | 1 | 109 |
| chr14:20014472_C_A | SNV | 0.35 | 0.00 | 0.00 | 125.40 | 66 | 107 | 19 | 768 | 4 | 110 |
| chr16:48139305_G_C | SNV | 0.34 | 0.00 | 0.00 | 106.10 | 68 | 107 | 17 | 768 | 4 | 111 |
| chr6:168310205_—_T | FSP | 0.27 | 2.65 | 1.34 | 10951.63 | 92 | 48 | 628 | 768 | 1 | 112 |
| chr11:1758971_AC_— | FSP | 0.31 | 460.80 | 2.03 | 12791.00 | 79 | 44 | 650 | 773 | 1 | 113 |
| chr6:168310205_—_T | FSP | 0.27 | 2.65 | 1.34 | 11784.46 | 92 | 48 | 635 | 775 | 1 | 114 |
| chr5:13735855_G_A | SNV | 0.30 | 0.11 | 0.11 | 411.75 | 81 | 74 | 39 | 776 | 4 | 115 |
| chr11:1758971_AC_— | FSP | 0.31 | 460.80 | 2.03 | 12923.30 | 79 | 44 | 653 | 776 | 1 | 116 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr6:168310205_—_T | FSP | 0.27 | 2.65 | 1.34 | 11857.00 | 92 | 48 | 638 | 778 | 1 | 117 |
| chr11:1758971_AC_— | FSP | 0.31 | 460.80 | 2.03 | 13652.17 | 79 | 44 | 660 | 783 | 1 | 118 |
| chr11:1758971_AC_— | FSP | 0.31 | 460.80 | 2.03 | 14287.03 | 79 | 44 | 663 | 786 | 1 | 119 |
| chr6:168310205_—_T | FSP | 0.27 | 2.65 | 1.34 | 12583.44 | 92 | 48 | 646 | 786 | 1 | 120 |
| chr11:1758971_AC_— | FSP | 0.31 | 460.80 | 2.03 | 14296.31 | 79 | 44 | 664 | 787 | 1 | 121 |
| chr11:1758971_AC_— | FSP | 0.31 | 460.80 | 2.03 | 14693.10 | 79 | 44 | 665 | 788 | 1 | 122 |
| chr13:35159543_G_C | SNV | 0.29 | 0.05 | 0.05 | 183.73 | 85 | 87 | 26 | 792 | 4 | 123 |
| chr11:1758971_AC_— | FSP | 0.31 | 460.80 | 2.03 | 15452.22 | 79 | 44 | 671 | 794 | 1 | 124 |
| chr11:1758971_AC_— | FSP | 0.31 | 460.80 | 2.03 | 15454.40 | 79 | 44 | 672 | 795 | 1 | 125 |
| chr11:1758971_AC_— | FSP | 0.31 | 460.80 | 2.03 | 15751.50 | 79 | 44 | 674 | 797 | 1 | 126 |
| chr11:1758971_AC_— | FSP | 0.31 | 460.80 | 2.03 | 15852.90 | 79 | 44 | 676 | 799 | 1 | 127 |
| chr6:168310205_—_T | FSP | 0.27 | 2.65 | 1.34 | 13712.13 | 92 | 48 | 661 | 801 | 1 | 128 |
| chr11:1758971_AC_— | FSP | 0.31 | 460.80 | 2.03 | 16323.72 | 79 | 44 | 681 | 804 | 1 | 129 |
| chr11:1758971_AC_— | FSP | 0.31 | 460.80 | 2.03 | 16590.60 | 79 | 44 | 684 | 807 | 1 | 130 |
| chr11:1758971_AC_— | FSP | 0.31 | 460.80 | 2.03 | 17904.32 | 79 | 44 | 688 | 811 | 1 | 131 |
| chr11:1758971_AC_— | FSP | 0.31 | 460.80 | 2.03 | 18021.12 | 79 | 44 | 690 | 813 | 1 | 132 |
| chr11:1758971_AC_— | FSP | 0.31 | 460.80 | 2.03 | 18197.08 | 79 | 44 | 691 | 814 | 1 | 133 |
| chr20:41421411_C_G | SNV | 0.21 | 3.16 | 3.16 | 16039.05 | 101 | 36 | 678 | 815 | 1 | 134 |
| chr11:1758971_AC_— | FSP | 0.31 | 460.80 | 2.03 | 18340.60 | 79 | 44 | 692 | 815 | 1 | 135 |
| chrX:22273538_G_C | SNV | 0.30 | 0.00 | 0.00 | 92.50 | 83 | 107 | 14 | 816 | 4 | 136 |
| chr11:1758971_AC_— | FSP | 0.31 | 460.80 | 2.03 | 19542.38 | 79 | 44 | 697 | 820 | 1 | 137 |
| chr11:1758971_AC_— | FSP | 0.31 | 460.80 | 2.03 | 19699.47 | 79 | 44 | 699 | 822 | 1 | 138 |
| chr11:1758971_AC_— | FSP | 0.31 | 460.80 | 2.03 | 20295.52 | 79 | 44 | 702 | 825 | 1 | 139 |
| chr6:168310205_—_T | FSP | 0.27 | 2.65 | 1.34 | 16675.60 | 92 | 48 | 685 | 825 | 1 | 140 |
| chr11:1758971_AC_— | FSP | 0.31 | 460.80 | 2.03 | 20605.06 | 79 | 44 | 703 | 826 | 1 | 141 |
| chr11:1758971_AC_— | FSP | 0.31 | 460.80 | 2.03 | 20630.27 | 79 | 44 | 705 | 828 | 1 | 142 |
| chr11:1758971_AC_— | FSP | 0.31 | 460.80 | 2.03 | 20638.98 | 79 | 44 | 706 | 829 | 1 | 143 |
| chr6:168310205_—_T | FSP | 0.27 | 2.65 | 1.34 | 17925.30 | 92 | 48 | 689 | 829 | 1 | 144 |
| chr11:1758971_AC_— | FSP | 0.31 | 460.80 | 2.03 | 20708.55 | 79 | 44 | 708 | 831 | 1 | 145 |
| chr2:167245082_T_G | SNV | 0.37 | 0.03 | 0.03 | 902.70 | 53 | 91 | 64 | 832 | 4 | 146 |
| chr11:1758971_AC_— | FSP | 0.31 | 460.80 | 2.03 | 20766.88 | 79 | 44 | 709 | 832 | 1 | 147 |
| chr11:1758971_AC_— | FSP | 0.31 | 460.80 | 2.03 | 21556.30 | 79 | 44 | 712 | 835 | 1 | 148 |
| chr11:1758971_AC_— | FSP | 0.31 | 460.80 | 2.03 | 21623.54 | 79 | 44 | 713 | 836 | 1 | 149 |
| chr11:1758971_AC_— | FSP | 0.31 | 460.80 | 2.03 | 22010.18 | 79 | 44 | 718 | 841 | 1 | 150 |
| chr11:1758971_AC_— | FSP | 0.31 | 460.80 | 2.03 | 22110.20 | 79 | 44 | 719 | 842 | 1 | 151 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr11:1758971_AC_— | FSP | 0.31 | 460.80 | 2.03 | 22153.29 | 79 | 44 | 720 | 843 | 1 | 152 |
| chr11:1758971_AC_— | FSP | 0.31 | 460.80 | 2.03 | 22354.83 | 79 | 44 | 721 | 844 | 1 | 153 |
| chr11:1758971_AC_— | FSP | 0.31 | 460.80 | 2.03 | 22550.39 | 79 | 44 | 723 | 846 | 1 | 154 |
| chr11:1758971_AC_— | FSP | 0.31 | 460.80 | 2.03 | 23193.80 | 79 | 44 | 725 | 848 | 1 | 155 |
| chr11:1758971_AC_— | FSP | 0.31 | 460.80 | 2.03 | 23265.15 | 79 | 44 | 726 | 849 | 1 | 156 |
| chr11:1758971_AC_— | FSP | 0.31 | 460.80 | 2.03 | 23324.88 | 79 | 44 | 727 | 850 | 1 | 157 |
| chr6:168310205_—_T | FSP | 0.27 | 2.65 | 1.34 | 21707.50 | 92 | 48 | 716 | 856 | 1 | 158 |
| chr11:1758971_AC_— | FSP | 0.31 | 460.80 | 2.03 | 24982.10 | 79 | 44 | 736 | 859 | 1 | 159 |
| chr11:1758971_AC_— | FSP | 0.31 | 460.80 | 2.03 | 25114.40 | 79 | 44 | 738 | 861 | 1 | 160 |
| chr6:168310205_—_T | FSP | 0.27 | 2.65 | 1.34 | 22541.60 | 92 | 48 | 722 | 862 | 1 | 161 |
| chr20:54157259_C_T | SNV | 0.30 | 0.09 | 0.09 | 710.20 | 83 | 79 | 54 | 864 | 4 | 162 |
| chr20:54157259_C_T | SNV | 0.30 | 0.09 | 0.09 | 710.20 | 83 | 79 | 54 | 864 | 4 | 163 |
| chr11:1758971_AC_— | FSP | 0.31 | 460.80 | 2.03 | 25633.30 | 79 | 44 | 741 | 864 | 1 | 164 |
| chr11:1758971_AC_— | FSP | 0.31 | 460.80 | 2.03 | 25736.92 | 79 | 44 | 742 | 865 | 1 | 165 |
| chr11:1758971_AC_— | FSP | 0.31 | 460.80 | 2.03 | 25960.10 | 79 | 44 | 744 | 867 | 1 | 166 |
| chr6:168310205_—_T | FSP | 0.27 | 2.65 | 1.34 | 23828.67 | 92 | 48 | 729 | 869 | 1 | 167 |
| chr11:1758971_AC_— | FSP | 0.31 | 460.80 | 2.03 | 27215.57 | 79 | 44 | 748 | 871 | 1 | 168 |
| chr11:26721564_C_G | SNV | 0.33 | 0.01 | 0.01 | 493.20 | 69 | 103 | 46 | 872 | 4 | 169 |
| chr11:1758971_AC_— | FSP | 0.31 | 460.80 | 2.03 | 27397.60 | 79 | 44 | 750 | 873 | 1 | 170 |
| chr11:1758971_AC_— | FSP | 0.31 | 460.80 | 2.03 | 28238.14 | 79 | 44 | 752 | 875 | 1 | 171 |
| chr3:32818692_G_— | FSP | 0.23 | 0.02 | 0.02 | 150.50 | 100 | 96 | 23 | 876 | 4 | 172 |
| chr11:1758971_AC_— | FSP | 0.31 | 460.80 | 2.03 | 28447.59 | 79 | 44 | 754 | 877 | 1 | 173 |
| chr11:1758971_AC_— | FSP | 0.31 | 460.80 | 2.03 | 29421.77 | 79 | 44 | 756 | 879 | 1 | 174 |
| chr11:1758971_AC_— | FSP | 0.31 | 460.80 | 2.03 | 29826.27 | 79 | 44 | 757 | 880 | 1 | 175 |
| chr11:1758971_AC_— | FSP | 0.31 | 460.80 | 2.03 | 31274.12 | 79 | 44 | 761 | 884 | 1 | 176 |
| chr11:1758971_AC_— | FSP | 0.31 | 460.80 | 2.03 | 31497.22 | 79 | 44 | 765 | 888 | 1 | 177 |
| chr11:1758971_AC_— | FSP | 0.31 | 460.80 | 2.03 | 32523.71 | 79 | 44 | 766 | 889 | 1 | 178 |
| chr11:1758971_AC_— | FSP | 0.31 | 460.80 | 2.03 | 33278.00 | 79 | 44 | 770 | 893 | 1 | 179 |
| chr11:1758971_AC_— | FSP | 0.31 | 460.80 | 2.03 | 33437.17 | 79 | 44 | 771 | 894 | 1 | 180 |
| chr11:1758971_AC_— | FSP | 0.31 | 460.80 | 2.03 | 34250.42 | 79 | 44 | 772 | 895 | 1 | 181 |
| chr11:1758971_AC_— | FSP | 0.31 | 460.80 | 2.03 | 34429.49 | 79 | 44 | 773 | 896 | 1 | 182 |
| chr11:1758971_AC_— | FSP | 0.31 | 460.80 | 2.03 | 38230.68 | 79 | 44 | 776 | 899 | 1 | 183 |
| chr6:168310205_—_T | FSP | 0.27 | 2.65 | 1.34 | 31468.96 | 92 | 48 | 764 | 904 | 1 | 184 |
| chr3:77596673_A_T | SNV | 0.23 | 0.01 | 0.01 | 203.50 | 99 | 100 | 28 | 908 | 4 | 185 |
| chr3:32818692_G_— | FSP | 0.23 | 0.02 | 0.02 | 270.50 | 100 | 96 | 33 | 916 | 4 | 186 |
| chr3:32818692_G_— | FSP | 0.23 | 0.02 | 0.02 | 479.90 | 100 | 96 | 43 | 956 | 4 | 187 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr3:32818692_G_— | FSP | 0.23 | 0.02 | 0.02 | 505.00 | 100 | 96 | 48 | 976 | 4 | 188 |
| chr3:32818692_G_— | FSP | 0.23 | 0.02 | 0.02 | 661.08 | 100 | 96 | 50 | 984 | 4 | 189 |
| chr3:32818692_G_— | FSP | 0.23 | 0.02 | 0.02 | 714.80 | 100 | 96 | 55 | 1004 | 4 | 190 |
| chr5:140842565_G_A | SNV | 0.27 | 0.01 | 0.01 | 884.93 | 94 | 101 | 63 | 1032 | 4 | 191 |
| chr3:32818692_G_— | FSP | 0.23 | 0.02 | 0.02 | 877.84 | 100 | 96 | 62 | 1032 | 4 | 192 |
| chr3:32818692_G_— | FSP | 0.23 | 0.02 | 0.02 | 949.20 | 100 | 96 | 68 | 1056 | 4 | 193 |
| chr1:228340587_G_T | SNV | 0.46 | 0.56 | 0.56 | 1734.70 | 20 | 59 | 486 | 1130 | 2 | 194 |
| chr18:56691285_G_T | SNV | 0.54 | 0.61 | 0.61 | 2190.30 | 15 | 58 | 502 | 1150 | 2 | 195 |
| chrX:50598303_G_T | SNV | 0.36 | 1.99 | 1.99 | 1552.80 | 59 | 45 | 478 | 1164 | 2 | 196 |
| chr7:6551366_G_C | SNV | 0.35 | 0.50 | 0.50 | 1340.50 | 64 | 60 | 475 | 1198 | 2 | 197 |
| chr12:89610020_C_T | SNV | 0.35 | 2.77 | 2.77 | 2031.40 | 67 | 40 | 496 | 1206 | 2 | 198 |
| chr6:107707925_A_G | SNV | 0.28 | 0.04 | 0.00 | 662.40 | 89 | 106 | 51 | 1230 | 5 | 199 |
| chr16:3757295_GATAGCTGTAGTAGGCAGCATC_— | FSP | 0.13 | 4.88 | 4.88 | 1628.90 | 102 | 33 | 481 | 1232 | 2 | 200 |
| chrX:18258064_C_T | SNV | 0.35 | 0.76 | 0.76 | 3122.43 | 66 | 55 | 519 | 1280 | 2 | 201 |
| chr16:3757295_GATAGCTGTAGTAGGCAGCATC_— | FSP | 0.13 | 4.88 | 4.88 | 2896.90 | 102 | 33 | 514 | 1298 | 2 | 202 |
| chr19:48735476_G_T | SNV | 0.74 | 2.60 | 2.60 | 9946.44 | 2 | 42 | 614 | 1316 | 2 | 203 |
| chrX:152936478_C_G | SNV | 0.27 | 2.82 | 2.82 | 4704.39 | 92 | 38 | 548 | 1356 | 2 | 204 |
| chr16:3757295 GATAGCTGTAGTAGGCAGCATC_— | FSP | 0.13 | 4.88 | 4.88 | 4689.60 | 102 | 33 | 547 | 1364 | 2 | 205 |
| chr16:3757295_GATAGCTGTAGTAGGCAGCATC_— | FSP | 0.13 | 4.88 | 4.88 | 5611.12 | 102 | 33 | 559 | 1388 | 2 | 206 |
| chr16:3757295_GATAGCTGTAGTAGGCAGCATC_— | FSP | 0.13 | 4.88 | 4.88 | 8166.46 | 102 | 33 | 594 | 1458 | 2 | 207 |
| chr16:3757295_GATAGCTGTAGTAGGCAGCATC_— | FSP | 0.13 | 4.88 | 4.88 | 8978.45 | 102 | 33 | 606 | 1482 | 2 | 208 |
| chr16:3757295_GATAGCTGTAGTAGGCAGCATC_— | FSP | 0.13 | 4.88 | 4.88 | 11787.80 | 102 | 33 | 636 | 1542 | 2 | 209 |
| chr16:3757295_GATAGCTGTAGTAGGCAGCATC_— | FSP | 0.13 | 4.88 | 4.88 | 12052.00 | 102 | 33 | 642 | 1554 | 2 | 210 |
| chr16:3757295_GATAGCTGTAGTAGGCAGCATC_— | FSP | 0.13 | 4.88 | 4.88 | 12434.20 | 102 | 33 | 645 | 1560 | 2 | 211 |
| chr16:3757295_GATAGCTGTAGTAGGCAGCATC_— | FSP | 0.13 | 4.88 | 4.88 | 20628.70 | 102 | 33 | 704 | 1678 | 2 | 212 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr16:3757295_GATAGCTGTAGTAGGCAGCATC_— | FSP | 0.13 | 4.88 | 4.88 | 20993.02 | 102 | 33 | 710 | 1690 | 2 | 213 |
| chr16:3757295_GATAGCTGTAGTAGGCAGCATC_— | FSP | 0.13 | 4.88 | 4.88 | 21762.73 | 102 | 33 | 717 | 1704 | 2 | 214 |
| chr16:3757295_GATAGCTGTAGTAGGCAGCATC_— | FSP | 0.13 | 4.88 | 4.88 | 24607.60 | 102 | 33 | 731 | 1732 | 2 | 215 |
| chr16:3757295_GATAGCTGTAGTAGGCAGCATC_— | FSP | 0.13 | 4.88 | 4.88 | 24793.40 | 102 | 33 | 734 | 1738 | 2 | 216 |
| chr16:3757295_GATAGCTGTAGTAGGCAGCATC_— | FSP | 0.13 | 4.88 | 4.88 | 26390.85 | 102 | 33 | 745 | 1760 | 2 | 217 |
| chr16:3757295_GATAGCTGTAGTAGGCAGCATC_— | FSP | 0.13 | 4.88 | 4.88 | 27260.40 | 102 | 33 | 749 | 1768 | 2 | 218 |
| chr16:3757295_GATAGCTGTAGTAGGCAGCATC_— | FSP | 0.13 | 4.88 | 4.88 | 27813.60 | 102 | 33 | 751 | 1772 | 2 | 219 |
| chr12:6817323_C_A | SNV | 0.29 | 6.71 | 0.13 | 1732.98 | 84 | 73 | 485 | 1926 | 3 | 220 |
| chr8:8377042_G_A | SNV | 0.37 | 4.62 | 0.11 | 3074.00 | 52 | 75 | 516 | 1929 | 3 | 221 |
| chr3:13614024_C_T | SNV | 0.43 | 6.35 | 0.20 | 5164.00 | 26 | 69 | 556 | 1953 | 3 | 222 |
| chrX:136044485_C_T | SNV | 0.40 | 3.38 | 0.31 | 6187.55 | 41 | 65 | 573 | 2037 | 3 | 223 |
| chr19:37565848_G_C | SNV | 0.67 | 0.20 | 0.20 | 2317.89 | 8 | 70 | 506 | 2336 | 4 | 224 |
| chr14:79861690_G_A | SNV | 0.42 | 0.04 | 0.04 | 1287.30 | 32 | 90 | 472 | 2376 | 4 | 225 |
| chr14:79861690_G_A | SNV | 0.42 | 0.04 | 0.04 | 1287.30 | 32 | 90 | 472 | 2376 | 4 | 226 |
| chr14:79861690_G_A | SNV | 0.42 | 0.04 | 0.04 | 1287.30 | 32 | 90 | 472 | 2376 | 4 | 227 |
| chr17:44778052_C_T | SNV | 0.64 | 0.09 | 0.09 | 2413.58 | 10 | 78 | 509 | 2388 | 4 | 228 |
| chrX:152766846_A_G | SNV | 0.44 | 0.00 | 0.00 | 1259.60 | 23 | 107 | 471 | 2404 | 4 | 229 |
| chr2:1267461_G_A | SNV | 0.40 | 0.07 | 0.07 | 2378.10 | 38 | 84 | 507 | 2516 | 4 | 230 |
| chr16:76467454_T_G | SNV | 0.42 | 0.00 | 0.00 | 2009.50 | 30 | 107 | 494 | 2524 | 4 | 231 |
| chr20:35434630_T_C | SNV | 0.32 | 0.03 | 0.03 | 1111.53 | 74 | 94 | 464 | 2528 | 4 | 232 |
| chr1:152314593_C_G | SNV | 0.37 | 0.00 | 0.00 | 1325.91 | 55 | 107 | 474 | 2544 | 4 | 233 |
| chr5:157343307_C_G | SNV | 0.36 | 0.00 | 0.00 | 1227.98 | 60 | 107 | 470 | 2548 | 4 | 234 |
| chr5:153811068_G_A | SNV | 0.40 | 0.00 | 0.00 | 1857.36 | 42 | 107 | 490 | 2556 | 4 | 235 |
| chr10:105255724_C_G | SNV | 0.38 | 0.02 | 0.02 | 2013.58 | 49 | 95 | 495 | 2556 | 4 | 236 |
| chr7:134568320_A_T | SNV | 0.36 | 0.00 | 0.00 | 1793.80 | 60 | 107 | 487 | 2616 | 4 | 237 |
| chr6:159804633_C_T | SNV | 0.39 | 0.21 | 0.21 | 4334.62 | 43 | 68 | 544 | 2620 | 4 | 238 |
| chrX:34131242_C_T | SNV | 0.39 | 0.00 | 0.00 | 2276.45 | 44 | 107 | 504 | 2620 | 4 | 239 |
| chr3:32818692_G_— | FSP | 0.23 | 0.02 | 0.02 | 1058.50 | 100 | 96 | 462 | 2632 | 4 | 240 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr3:32818692_G_— | FSP | 0.23 | 0.02 | 0.02 | 1087.90 | 100 | 96 | 463 | 2636 | 4 | 241 |
| chr4:176168671_G_A | SNV | 0.57 | 0.02 | 0.02 | 4779.70 | 14 | 98 | 551 | 2652 | 4 | 242 |
| chr2:184936876_A_G | SNV | 0.30 | 0.03 | 0.03 | 1898.15 | 80 | 93 | 492 | 2660 | 4 | 243 |
| chrX:105220039_G_A | SNV | 0.41 | 0.00 | 0.00 | 3345.76 | 35 | 107 | 525 | 2668 | 4 | 244 |
| chr3:32818692_G_— | FSP | 0.23 | 0.02 | 0.02 | 1290.90 | 100 | 96 | 473 | 2676 | 4 | 245 |
| chr17:80090197_A_G | SNV | 0.40 | 0.40 | 0.40 | 6137.68 | 39 | 63 | 568 | 2680 | 4 | 246 |
| chr3:32818692_G_— | FSP | 0.23 | 0.02 | 0.02 | 1405.50 | 100 | 96 | 477 | 2692 | 4 | 247 |
| chr3:32818692_G_— | FSP | 0.23 | 0.02 | 0.02 | 1717.75 | 100 | 96 | 484 | 2720 | 4 | 248 |
| chr3:32818692_G_— | FSP | 0.23 | 0.02 | 0.02 | 1815.40 | 100 | 96 | 488 | 2736 | 4 | 249 |
| chr3:32818692_G_— | FSP | 0.23 | 0.02 | 0.02 | 1849.50 | 100 | 96 | 489 | 2740 | 4 | 250 |
| chr3:32818692_G_— | FSP | 0.23 | 0.02 | 0.02 | 1870.22 | 100 | 96 | 491 | 2748 | 4 | 251 |
| chrX:151180935_T_A | SNV | 0.43 | 0.04 | 0.04 | 6377.67 | 29 | 88 | 575 | 2768 | 4 | 252 |
| chr3:32818692_G_— | FSP | 0.23 | 0.02 | 0.02 | 2034.30 | 100 | 96 | 497 | 2772 | 4 | 253 |
| chr3:32818692_G_— | FSP | 0.23 | 0.02 | 0.02 | 2096.09 | 100 | 96 | 499 | 2780 | 4 | 254 |
| chr3:32818692_G_— | FSP | 0.23 | 0.02 | 0.02 | 2202.40 | 100 | 96 | 503 | 2796 | 4 | 255 |
| chr3:32818692_G_— | FSP | 0.23 | 0.02 | 0.02 | 2769.94 | 100 | 96 | 511 | 2828 | 4 | 256 |
| chr3:32818692_G_— | FSP | 0.23 | 0.02 | 0.02 | 2800.71 | 100 | 96 | 512 | 2832 | 4 | 257 |
| chr3:32818692_G_— | FSP | 0.23 | 0.02 | 0.02 | 2973.24 | 100 | 96 | 515 | 2844 | 4 | 258 |
| chr3:32818692_G_— | FSP | 0.23 | 0.02 | 0.02 | 3183.11 | 100 | 96 | 520 | 2864 | 4 | 259 |
| chr2:206177163_C_G | SNV | 0.36 | 0.06 | 0.06 | 6187.82 | 60 | 86 | 574 | 2880 | 4 | 260 |
| chr19:31279054_C_T | SNV | 0.64 | 0.32 | 0.32 | 12623.68 | 10 | 64 | 647 | 2884 | 4 | 261 |
| chr3:32818692_G_— | FSP | 0.23 | 0.02 | 0.02 | 3454.02 | 100 | 96 | 528 | 2896 | 4 | 262 |
| chr3:87264320_G_C | SNV | 0.37 | 0.00 | 0.00 | 5983.30 | 53 | 107 | 566 | 2904 | 4 | 263 |
| chr3:32818692_G_— | FSP | 0.23 | 0.02 | 0.02 | 3477.00 | 100 | 96 | 530 | 2904 | 4 | 264 |
| chr18:32677240_C_G | SNV | 0.49 | 0.00 | 0.00 | 8898.95 | 18 | 107 | 603 | 2912 | 4 | 265 |
| chr3:32818692_G_— | FSP | 0.23 | 0.02 | 0.02 | 3686.04 | 100 | 96 | 534 | 2920 | 4 | 266 |
| chr3:32818692_G_— | FSP | 0.23 | 0.02 | 0.02 | 3708.97 | 100 | 96 | 535 | 2924 | 4 | 267 |
| chr3:32818692_G_— | FSP | 0.23 | 0.02 | 0.02 | 3775.45 | 100 | 96 | 536 | 2928 | 4 | 268 |
| chr3:32818692_G_— | FSP | 0.23 | 0.02 | 0.02 | 3822.90 | 100 | 96 | 537 | 2932 | 4 | 269 |
| chr3:32818692_G_— | FSP | 0.23 | 0.02 | 0.02 | 4006.60 | 100 | 96 | 539 | 2940 | 4 | 270 |
| chr3:32818692_G_— | FSP | 0.23 | 0.02 | 0.02 | 4278.47 | 100 | 96 | 541 | 2948 | 4 | 271 |
| chr3:32818692_G_— | FSP | 0.23 | 0.02 | 0.02 | 4312.30 | 100 | 96 | 543 | 2956 | 4 | 272 |
| chr17:35746314_G_A | SNV | 0.63 | 0.04 | 0.04 | 12000.37 | 11 | 89 | 641 | 2964 | 4 | 273 |
| chr10:25221118_G_C | SNV | 0.28 | 0.02 | 0.02 | 5031.73 | 90 | 97 | 555 | 2968 | 4 | 274 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr3:32818692_G_— | FSP | 0.23 | 0.02 | 0.02 | 4492.50 | 100 | 96 | 546 | 2968 | 4 | 275 |
| chr9:17342330_A_C | SNV | 0.52 | 0.06 | 0.01 | 1613.40 | 16 | 104 | 479 | 2995 | 5 | 276 |
| chr3:32818692_G_— | FSP | 0.23 | 0.02 | 0.02 | 5285.90 | 100 | 96 | 557 | 3012 | 4 | 277 |
| chr3:32818692_G_— | FSP | 0.23 | 0.02 | 0.02 | 5612.09 | 100 | 96 | 560 | 3024 | 4 | 278 |
| chr3:32818692_G_— | FSP | 0.23 | 0.02 | 0.02 | 5630.28 | 100 | 96 | 561 | 3028 | 4 | 279 |
| chr3:32818692_G_— | FSP | 0.23 | 0.02 | 0.02 | 5659.80 | 100 | 96 | 562 | 3032 | 4 | 280 |
| chr3:32818692_G_— | FSP | 0.23 | 0.02 | 0.02 | 5689.90 | 100 | 96 | 563 | 3036 | 4 | 281 |
| chr3:32818692_G_— | FSP | 0.23 | 0.02 | 0.02 | 5930.90 | 100 | 96 | 565 | 3044 | 4 | 282 |
| chr20:49373631_G_C | SNV | 0.28 | 0.00 | 0.00 | 5746.60 | 91 | 107 | 564 | 3048 | 4 | 283 |
| chr3:32818692_G_— | FSP | 0.23 | 0.02 | 0.02 | 6139.41 | 100 | 96 | 570 | 3064 | 4 | 284 |
| chr3:32818692_G_— | FSP | 0.23 | 0.02 | 0.02 | 6160.50 | 100 | 96 | 571 | 3068 | 4 | 285 |
| chr3:32818692_G_— | FSP | 0.23 | 0.02 | 0.02 | 6454.30 | 100 | 96 | 577 | 3092 | 4 | 286 |
| chr3:32818692_G_— | FSP | 0.23 | 0.02 | 0.02 | 6638.53 | 100 | 96 | 578 | 3096 | 4 | 287 |
| chr3:32818692_G_— | FSP | 0.23 | 0.02 | 0.02 | 6804.11 | 100 | 96 | 579 | 3100 | 4 | 288 |
| chr3:32818692_G_— | FSP | 0.23 | 0.02 | 0.02 | 6848.80 | 100 | 96 | 581 | 3108 | 4 | 289 |
| chr3:32818692_G_— | FSP | 0.23 | 0.02 | 0.02 | 7034.10 | 100 | 96 | 582 | 3112 | 4 | 290 |
| chr3:32818692_G_— | FSP | 0.23 | 0.02 | 0.02 | 7048.24 | 100 | 96 | 583 | 3116 | 4 | 291 |
| chr3:32818692_G_— | FSP | 0.23 | 0.02 | 0.02 | 7114.70 | 100 | 96 | 586 | 3128 | 4 | 292 |
| chr6:26506794_A_G | SNV | 0.29 | 0.00 | 0.00 | 7601.31 | 87 | 107 | 589 | 3132 | 4 | 293 |
| chr3:32818692_G_— | FSP | 0.23 | 0.02 | 0.02 | 7381.50 | 100 | 96 | 588 | 3136 | 4 | 294 |
| chr3:32818692_G_— | FSP | 0.23 | 0.02 | 0.02 | 7750.64 | 100 | 96 | 590 | 3144 | 4 | 295 |
| chr3:32818692_G_— | FSP | 0.23 | 0.02 | 0.02 | 7925.40 | 100 | 96 | 591 | 3148 | 4 | 296 |
| chr3:32818692_G_— | FSP | 0.23 | 0.02 | 0.02 | 7949.12 | 100 | 96 | 592 | 3152 | 4 | 297 |
| chr3:32818692_G_— | FSP | 0.23 | 0.02 | 0.02 | 8085.74 | 100 | 96 | 593 | 3156 | 4 | 298 |
| chr1:237004287_C_G | SNV | 0.36 | 0.00 | 0.00 | 10648.42 | 61 | 107 | 623 | 3164 | 4 | 299 |
| chr3:32818692_G_— | FSP | 0.23 | 0.02 | 0.02 | 8191.58 | 100 | 96 | 596 | 3168 | 4 | 300 |
| chr2:109449244_T_C | SNV | 0.33 | 0.25 | 0.01 | 1019.10 | 72 | 102 | 460 | 3170 | 5 | 301 |
| chr3:32818692_G_— | FSP | 0.23 | 0.02 | 0.02 | 8271.93 | 100 | 96 | 597 | 3172 | 4 | 302 |
| chr3:32818692_G_— | FSP | 0.23 | 0.02 | 0.02 | 8567.05 | 100 | 96 | 598 | 3176 | 4 | 303 |
| chr3:32818692_G_— | FSP | 0.23 | 0.02 | 0.02 | 8612.10 | 100 | 96 | 599 | 3180 | 4 | 304 |
| chr3:32818692_G_— | FSP | 0.23 | 0.02 | 0.02 | 8877.89 | 100 | 96 | 602 | 3192 | 4 | 305 |
| chr3:32818692_G_— | FSP | 0.23 | 0.02 | 0.02 | 8963.69 | 100 | 96 | 604 | 3200 | 4 | 306 |
| chr3:32818692_G_— | FSP | 0.23 | 0.02 | 0.02 | 8974.37 | 100 | 96 | 605 | 3204 | 4 | 307 |
| chr3:32818692_G_— | FSP | 0.23 | 0.02 | 0.02 | 9105.70 | 100 | 96 | 607 | 3212 | 4 | 308 |
| chr3:32818692_G_— | FSP | 0.23 | 0.02 | 0.02 | 9348.30 | 100 | 96 | 609 | 3220 | 4 | 309 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr3:32818692_G_— | FSP | 0.23 | 0.02 | 0.02 | 9448.60 | 100 | 96 | 610 | 3224 | 4 | 310 |
| chr3:32818692_G_— | FSP | 0.23 | 0.02 | 0.02 | 9647.54 | 100 | 96 | 611 | 3228 | 4 | 311 |
| chr3:32818692_G_— | FSP | 0.23 | 0.02 | 0.02 | 9671.30 | 100 | 96 | 612 | 3232 | 4 | 312 |
| chr3:32818692_G_— | FSP | 0.23 | 0.02 | 0.02 | 9950.63 | 100 | 96 | 615 | 3244 | 4 | 313 |
| chr3:32818692_G_— | FSP | 0.23 | 0.02 | 0.02 | 10203.10 | 100 | 96 | 618 | 3256 | 4 | 314 |
| chr3:32818692_G_— | FSP | 0.23 | 0.02 | 0.02 | 10520.50 | 100 | 96 | 620 | 3264 | 4 | 315 |
| chr3:32818692_G_— | FSP | 0.23 | 0.02 | 0.02 | 10583.18 | 100 | 96 | 621 | 3268 | 4 | 316 |
| chr2:178590588_T_G | SNV | 0.38 | 0.11 | 0.11 | 19366.19 | 46 | 76 | 696 | 3272 | 4 | 317 |
| chr3:32818692_G_— | FSP | 0.23 | 0.02 | 0.02 | 10665.70 | 100 | 96 | 624 | 3280 | 4 | 318 |
| chr3:32818692_G_— | FSP | 0.23 | 0.02 | 0.02 | 10733.44 | 100 | 96 | 625 | 3284 | 4 | 319 |
| chr3:32818692_G_— | FSP | 0.23 | 0.02 | 0.02 | 10905.52 | 100 | 96 | 626 | 3288 | 4 | 320 |
| chr3:32818692_G_— | FSP | 0.23 | 0.02 | 0.02 | 11377.89 | 100 | 96 | 629 | 3300 | 4 | 321 |
| chr3:32818692_G_— | FSP | 0.23 | 0.02 | 0.02 | 11520.50 | 100 | 96 | 630 | 3304 | 4 | 322 |
| chr3:32818692_G_— | FSP | 0.23 | 0.02 | 0.02 | 11539.68 | 100 | 96 | 631 | 3308 | 4 | 323 |
| chr19:53141032_C_A | SNV | 0.23 | 0.33 | 0.03 | 1205.50 | 100 | 94 | 469 | 3315 | 5 | 324 |
| chr3:32818692_G_— | FSP | 0.23 | 0.02 | 0.02 | 11753.52 | 100 | 96 | 633 | 3316 | 4 | 325 |
| chr3:32818692_G_— | FSP | 0.23 | 0.02 | 0.02 | 11765.10 | 100 | 96 | 634 | 3320 | 4 | 326 |
| chr3:32818692_G_— | FSP | 0.23 | 0.02 | 0.02 | 11842.62 | 100 | 96 | 637 | 3332 | 4 | 327 |
| chr3:32818692_G_— | FSP | 0.23 | 0.02 | 0.02 | 12102.86 | 100 | 96 | 643 | 3356 | 4 | 328 |
| chr12:40364940_T_A | SNV | 0.38 | 0.06 | 0.01 | 3199.80 | 47 | 105 | 521 | 3365 | 5 | 329 |
| chr3:32818692_G_— | FSP | 0.23 | 0.02 | 0.02 | 12656.64 | 100 | 96 | 648 | 3376 | 4 | 330 |
| chr3:32818692_G_— | FSP | 0.23 | 0.02 | 0.02 | 12691.33 | 100 | 96 | 649 | 3380 | 4 | 331 |
| chr3:32818692_G_— | FSP | 0.23 | 0.02 | 0.02 | 12828.00 | 100 | 96 | 651 | 3388 | 4 | 332 |
| chr3:32818692_G_— | FSP | 0.23 | 0.02 | 0.02 | 12851.35 | 100 | 96 | 652 | 3392 | 4 | 333 |
| chr3:32818692_G_— | FSP | 0.23 | 0.02 | 0.02 | 12946.10 | 100 | 96 | 654 | 3400 | 4 | 334 |
| chr3:32818692_G_— | FSP | 0.23 | 0.02 | 0.02 | 12961.52 | 100 | 96 | 655 | 3404 | 4 | 335 |
| chr3:32818692_G_— | FSP | 0.23 | 0.02 | 0.02 | 13342.29 | 100 | 96 | 656 | 3408 | 4 | 336 |
| chr3:32818692_G_— | FSP | 0.23 | 0.02 | 0.02 | 13355.58 | 100 | 96 | 657 | 3412 | 4 | 337 |
| chr3:32818692_G_— | FSP | 0.23 | 0.02 | 0.02 | 13399.40 | 100 | 96 | 658 | 3416 | 4 | 338 |
| chr3:32818692_G_— | FSP | 0.23 | 0.02 | 0.02 | 13632.20 | 100 | 96 | 659 | 3420 | 4 | 339 |
| chr2:40429308_C_G | SNV | 0.29 | 0.18 | 0.02 | 2142.39 | 86 | 99 | 501 | 3430 | 5 | 340 |
| chr3:32818692_G_— | FSP | 0.23 | 0.02 | 0.02 | 14044.57 | 100 | 96 | 662 | 3432 | 4 | 341 |
| chr3:32818692_G_— | FSP | 0.23 | 0.02 | 0.02 | 14772.61 | 100 | 96 | 666 | 3448 | 4 | 342 |
| chr3:32818692_G_— | FSP | 0.23 | 0.02 | 0.02 | 15038.22 | 100 | 96 | 667 | 3452 | 4 | 343 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr3:32818692_G_— | FSP | 0.23 | 0.02 | 0.02 | 15092.20 | 100 | 96 | 668 | 3456 | 4 | 344 |
| chr3:32818692_G_— | FSP | 0.23 | 0.02 | 0.02 | 15276.50 | 100 | 96 | 669 | 3460 | 4 | 345 |
| chr3:32818692_G_— | FSP | 0.23 | 0.02 | 0.02 | 15414.60 | 100 | 96 | 670 | 3464 | 4 | 346 |
| chr3:32818692_G_— | FSP | 0.23 | 0.02 | 0.02 | 15700.12 | 100 | 96 | 673 | 3476 | 4 | 347 |
| chr3:32818692_G_— | FSP | 0.23 | 0.02 | 0.02 | 15851.40 | 100 | 96 | 675 | 3484 | 4 | 348 |
| chr3:32818692_G_— | FSP | 0.23 | 0.02 | 0.02 | 15910.46 | 100 | 96 | 677 | 3492 | 4 | 349 |
| chr3:32818692_G_— | FSP | 0.23 | 0.02 | 0.02 | 16085.80 | 100 | 96 | 679 | 3500 | 4 | 350 |
| chr3:32818692_G_— | FSP | 0.23 | 0.02 | 0.02 | 16257.45 | 100 | 96 | 680 | 3504 | 4 | 351 |
| chr3:32818692_G_— | FSP | 0.23 | 0.02 | 0.02 | 16325.14 | 100 | 96 | 682 | 3512 | 4 | 352 |
| chr3:32818692_G_— | FSP | 0.23 | 0.02 | 0.02 | 16570.20 | 100 | 96 | 683 | 3516 | 4 | 353 |
| chr3:32818692_G_— | FSP | 0.23 | 0.02 | 0.02 | 17462.94 | 100 | 96 | 686 | 3528 | 4 | 354 |
| chr3:32818692_G_— | FSP | 0.23 | 0.02 | 0.02 | 17746.36 | 100 | 96 | 687 | 3532 | 4 | 355 |
| chr4:41626984_A_— | FSP | 0.43 | 0.00 | 0.00 | 28309.42 | 25 | 107 | 753 | 3540 | 4 | 356 |
| chr3:32818692_G_— | FSP | 0.23 | 0.02 | 0.02 | 18668.33 | 100 | 96 | 693 | 3556 | 4 | 357 |
| chr3:32818692_G_— | FSP | 0.23 | 0.02 | 0.02 | 18966.40 | 100 | 96 | 694 | 3560 | 4 | 358 |
| chr3:32818692_G_— | FSP | 0.23 | 0.02 | 0.02 | 18997.40 | 100 | 96 | 695 | 3564 | 4 | 359 |
| chr3:32818692_G_— | FSP | 0.23 | 0.02 | 0.02 | 19654.12 | 100 | 96 | 698 | 3576 | 4 | 360 |
| chr3:32818692_G_— | FSP | 0.23 | 0.02 | 0.02 | 19765.22 | 100 | 96 | 700 | 3584 | 4 | 361 |
| chr3:32818692_G_— | FSP | 0.23 | 0.02 | 0.02 | 20186.50 | 100 | 96 | 701 | 3588 | 4 | 362 |
| chr3:32818692_G_— | FSP | 0.23 | 0.02 | 0.02 | 20672.50 | 100 | 96 | 707 | 3612 | 4 | 363 |
| chr3:32818692_G_— | FSP | 0.23 | 0.02 | 0.02 | 21269.90 | 100 | 96 | 711 | 3628 | 4 | 364 |
| chr3:32818692_G_— | FSP | 0.23 | 0.02 | 0.02 | 21631.73 | 100 | 96 | 714 | 3640 | 4 | 365 |
| chr3:32818692_G_— | FSP | 0.23 | 0.02 | 0.02 | 21665.22 | 100 | 96 | 715 | 3644 | 4 | 366 |
| chr3:32818692_G_— | FSP | 0.23 | 0.02 | 0.02 | 22959.31 | 100 | 96 | 724 | 3680 | 4 | 367 |
| chr3:32818692_G_— | FSP | 0.23 | 0.02 | 0.02 | 23755.06 | 100 | 96 | 728 | 3696 | 4 | 368 |
| chr3:32818692_G_— | FSP | 0.23 | 0.02 | 0.02 | 23864.03 | 100 | 96 | 730 | 3704 | 4 | 369 |
| chr3:32818692_G_— | FSP | 0.23 | 0.02 | 0.02 | 24620.96 | 100 | 96 | 732 | 3712 | 4 | 370 |
| chr3:32818692_G_— | FSP | 0.23 | 0.02 | 0.02 | 24726.14 | 100 | 96 | 733 | 3716 | 4 | 371 |
| chr3:32818692_G_— | FSP | 0.23 | 0.02 | 0.02 | 24803.80 | 100 | 96 | 735 | 3724 | 4 | 372 |
| chr3:32818692_G_— | FSP | 0.23 | 0.02 | 0.02 | 25104.30 | 100 | 96 | 737 | 3732 | 4 | 373 |
| chr3:32818692_G_— | FSP | 0.23 | 0.02 | 0.02 | 25420.90 | 100 | 96 | 739 | 3740 | 4 | 374 |
| chr3:32818692_G_— | FSP | 0.23 | 0.02 | 0.02 | 25464.08 | 100 | 96 | 740 | 3744 | 4 | 375 |
| chr3:32818692_G_— | FSP | 0.23 | 0.02 | 0.02 | 25831.50 | 100 | 96 | 743 | 3756 | 4 | 376 |

TABLE 6-continued

All 388 neoantigens for Pat_3492 ordered by their RSUM rank. For FSP-derived neoantigens amino acids that are part of the frameshift peptide are also in bold. Neoantigen sequences with experimentally verified to induce T-cell reactivity are labelled TP in the column "Final Rank". Genomic coordinates given are with respect to human genome assembly GRch38/hg38.

| ID | TYPE | AFREQ | TPM | corr TPM | BEST IC50 | RFREQ | REXPR | RIC50 | RSUM | WF | NEOAG RANK |
|---|---|---|---|---|---|---|---|---|---|---|---|
| chr3:32818692_G_— | FSP | 0.23 | 0.02 | 0.02 | 26890.66 | 100 | 96 | 746 | 3768 | 4 | 377 |
| chr3:32818692_G_— | FSP | 0.23 | 0.02 | 0.02 | 26967.88 | 100 | 96 | 747 | 3772 | 4 | 378 |
| chr3:32818692_G_— | FSP | 0.23 | 0.02 | 0.02 | 28923.39 | 100 | 96 | 755 | 3804 | 4 | 379 |
| chr3:32818692_G_— | FSP | 0.23 | 0.02 | 0.02 | 29869.22 | 100 | 96 | 758 | 3816 | 4 | 380 |
| chr3:32818692_G_— | FSP | 0.23 | 0.02 | 0.02 | 30437.50 | 100 | 96 | 759 | 3820 | 4 | 381 |
| chr3:32818692_G_— | FSP | 0.23 | 0.02 | 0.02 | 30767.65 | 100 | 96 | 760 | 3824 | 4 | 382 |
| chr3:32818692_G_— | FSP | 0.23 | 0.02 | 0.02 | 31304.90 | 100 | 96 | 762 | 3832 | 4 | 383 |
| chr3:32818692_G_— | FSP | 0.23 | 0.02 | 0.02 | 31310.69 | 100 | 96 | 763 | 3836 | 4 | 384 |
| chr3:32818692_G_— | FSP | 0.23 | 0.02 | 0.02 | 32580.77 | 100 | 96 | 767 | 3852 | 4 | 385 |
| chr3:32818692_G_— | FSP | 0.23 | 0.02 | 0.02 | 32618.86 | 100 | 96 | 768 | 3856 | 4 | 386 |
| chr3:32818692_G_— | FSP | 0.23 | 0.02 | 0.02 | 33215.41 | 100 | 96 | 769 | 3860 | 4 | 387 |
| chr3:32818692_G_— | FSP | 0.23 | 0.02 | 0.02 | 35308.13 | 100 | 96 | 775 | 3884 | 4 | 388 |

Example 3: Validation of the prioritization method In order to validate the prioritization method datasets with a total of 30 experimentally validated immunogenic neoantigens with $CD8^+$ T-cell reactivity were analysed (Table 7). The datasets comprise biopsies from 13 cancer patients across 5 different tumor types for which NGS raw data (normal/tumor exome NGS-DNA and tumor NGS-RNA transcriptome) is available.

NGS data were downloaded from the NCBI SRA website and processed with the same NGS processing pipeline applied in Example 1. Mutations for 28 out of the 30 reported experimentally validated neoantigens were identified by applying the NGS processing pipeline disclosed in Example 2 (two mutations were not detected due to the very low number of mutated reads). For each patient sample the total list of all neoantigens identified was then ranked according to the method described in Step 3 in Example 1 assuming a target maximal polypeptide (polyneoantigen) size of 1500 amino acids.

Table 8 shows the predicted MHC class I IC50 values for the 28 neoantigens, for only 9mer epitope prediction or for predictions including epitopes from 8 up to 11 amino acids. In both cases several neoantigens are present where the best (lowest) IC50 values are well above (higher) than the 500 nM threshold value frequently applied in the art for the selection of neoantigen vaccine candidates and, consequently, would have been excluded from the personalized vaccine.

Figure 7A:
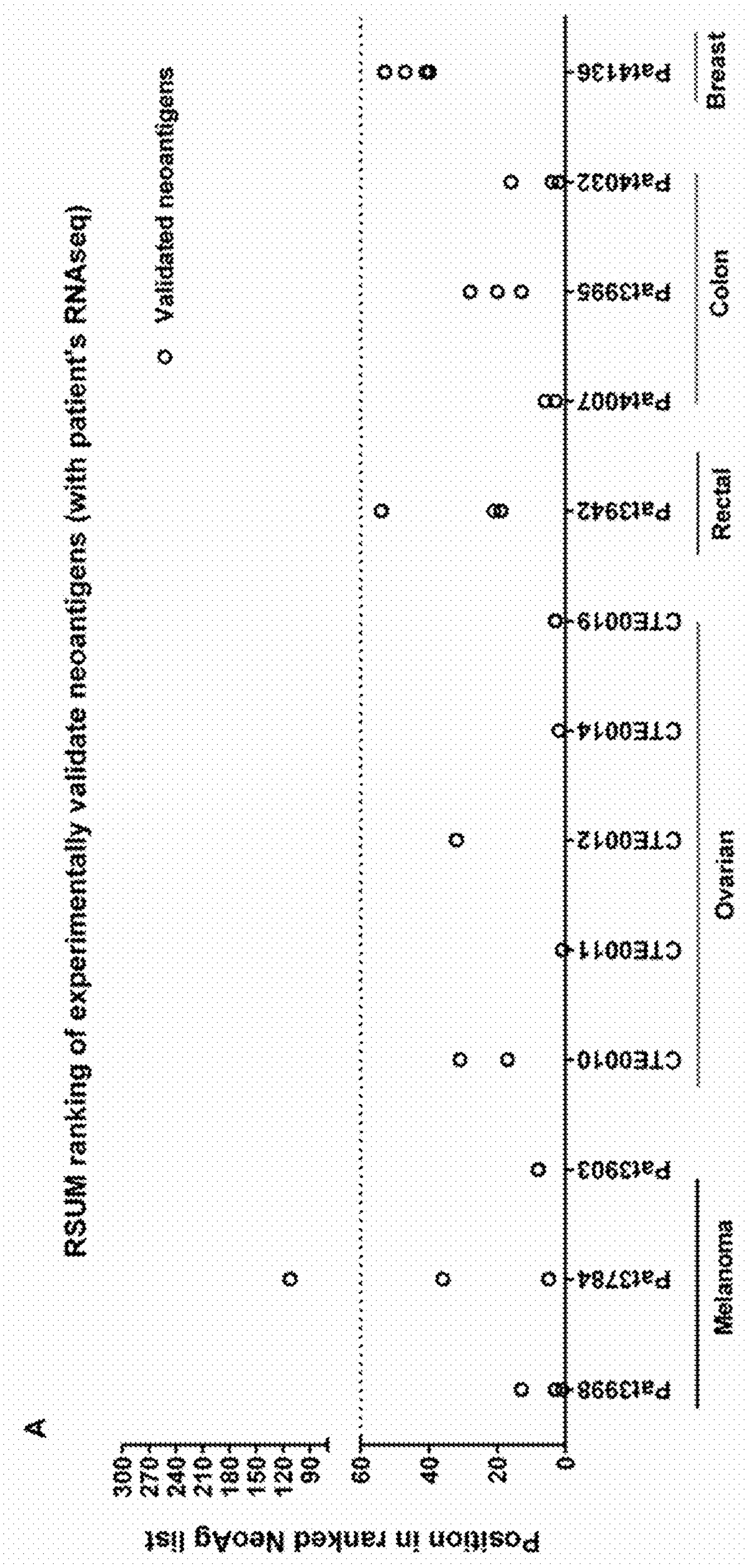

FIG. 7A shows the RSUM rank obtained by the prioritization method for the 28 detected experimentally validated neoantigens. A dotted line (FIG. 5A) indicates the maximal number of neoantigen 25mers (60) that can be accommodated in an adenoviral personalized vaccine vector with an insert capacity (excluding expression control elements) of about 1500 amino acids.

Figure 7B:
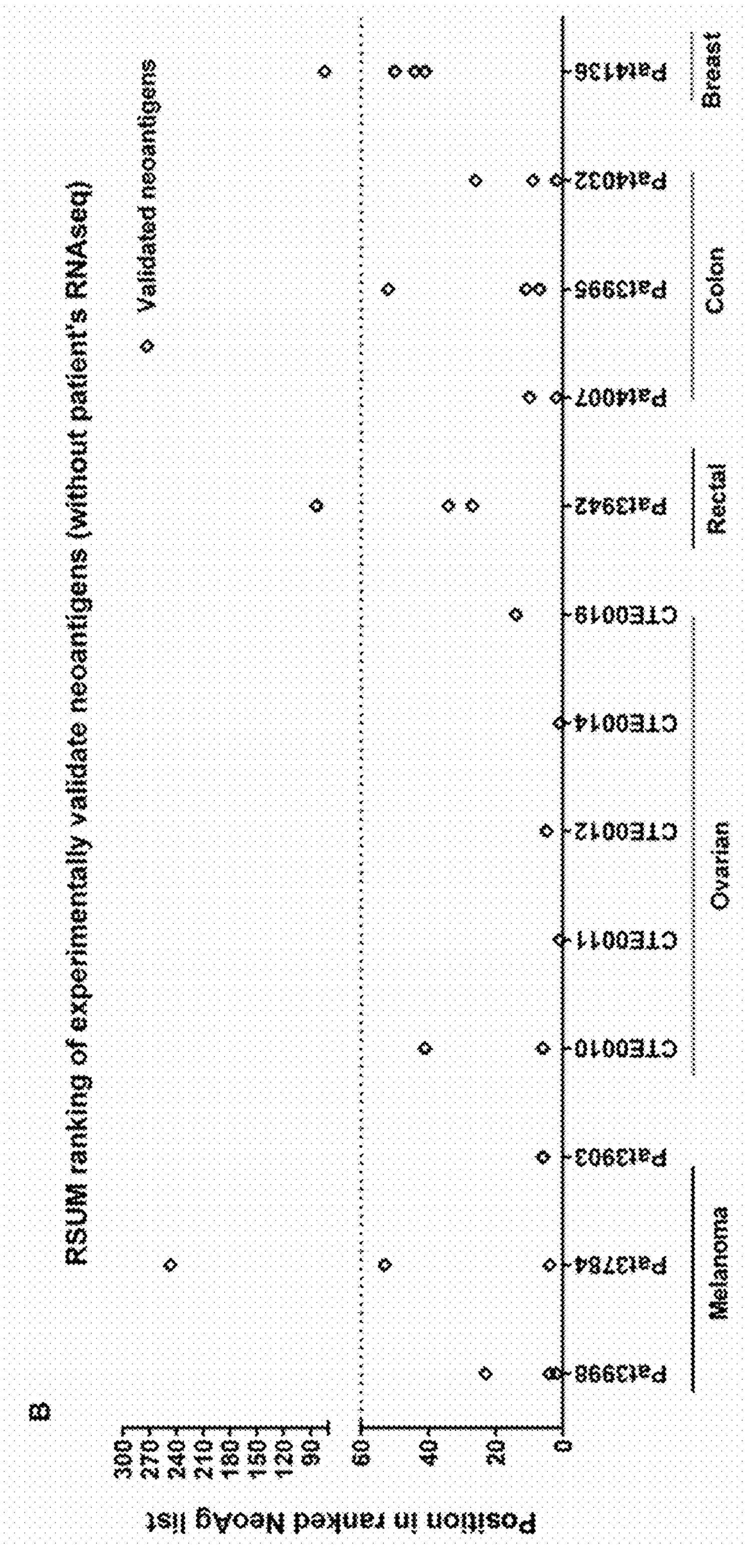

27 out of the 30 experimentally validated neoantigens (90%) are present in the top 60 neoantigens and therefore would have been included in the personalized vaccine vector. The priorization was then repeated assuming that no NGS-RNA expression data from the patient's tumor was available. The corrTPM expression value for each neoantigen was estimated as the median TPM value of the corresponding gene in the TCGA expression data for that particular tumor type [NCBI GEO accession:GSE62944]. FIG. 7B shows that also in this case a large portion (25 out of 30=83%) experimentally validated neoantigens would have been included in the vaccine vector. Importantly, for each of the examined datasets there was at least one validated neoantigen that would have been included in the personalized vaccine vector. Further details including the RSUM ranking results with and without NGS-RNA data for the 28 validated neoantigens are listed in Table 7.

Both results therefore confirmed that the prioritization method is able to select, in the presence but also in the absence of transcriptome data from the patient's tumor, a list of neoantigens that includes the most relevant neoantigens, i.e. those neoantigens with experimentally verified immunogenicity that should be included in a personalized vaccine vector.

TABLE 7

List of literature datasets and neoantigens used as benchmark. For each dataset neoantigens with experimentally validated T-cell reactivity are listed. The mutated amino acid is indicated in bold and underlined. For mutations generating two distinct neoantigens due to the presence of two alternative splicing isoforms only the neoantigen with the lower RSUM rank is reported (indicated by a *). Genomic coordinates given are with respect to human genome assembly GRch38/hg38.

| Tumor type | Study PUB MED ID | Patient ID | Mutation ID | RSUM rank (with RNASeq) | RSUM rank (no RNASeq) | SEQ ID NO | NeoAg sequence |
|---|---|---|---|---|---|---|---|
| Melanoma | 26901407 | Pat3998 | chrX:152767149_C_T | 1 | 2 | 80 | DSLQLVFGIELM**K**VDPIGHVYIFAT |
| Melanoma | 26901407 | Pat3998 | chr4:39862286_G_A | 3* | 4* | 81 | SLLPEFVVPYMI**Y**LLAHDPDFTRSQ |
| Melanoma | 26901407 | Pat3998 | chr17:61961773_G_A | 13 | 23 | 82 | PHIKSTVSVQII**S**CQYLLQPVKHED |
| Melanoma | 26901407 | Pat3784 | chrX:154353082_G_A | 5 | 4 | 83 | VVISQSEIGDAS**C**VRVSGQGLHEGH |
| Melanoma | 26901407 | Pat3784 | chr21:33555010_C_T | 36 | 53 | 84 | RKTVRARSRTPS**C**RSRSHTPSRRRR |
| Melanoma | 26901407 | Pat3784 | chr20:16378976_A_G | 112 | 247 | 85 | REKQQREALERA**P**ARLERRHSALQR |
| Melanoma | 26901407 | Pat3903 | chr10:69005862_C_T | 8 | 6 | 86 | TLKRQLEHNAYH**S**IEWAINAATLSQ |
| Ovarian | 2954554 | CTE0010 | chr11:6641192_G_A | 16 | 6 | 87 | VTVRVADINDHA**L**AFPQARAALQVP |
| Ovarian | 2954554 | CTE0010 | chr6:30186008_T_A | 31 | 41 | 88 | LRPRRVGIALDY**D**WGTVTFTNAESQ |
| Ovarian | 2954554 | CTE0011 | chr17:77482288_G_A | 18 | 1 | 89 | GYVGIDSILEQM**H**RKAMKQGFEFNI |
| Ovarian | 2954554 | CTE0012 | chr1:13614365_G_T | 40 | 5 | 90 | IIVGVLLAIGFI**C**AIIVVVMRKMSG |
| Ovarian | 2954554 | CTE0014 | chr11:11892058_G_C | 2 | 1 | 91 | PREGSGGSTSDY**L**SQSYSYSSILNK |
| Ovarian | 2954554 | CTE0019 | chr4:182799720_C_T | 3 | 14 | 92 | RRAGGAQSWLWF**V**TVKSLIGKGVML |
| Rectal | 26516200 | Pat3942 | chr2:156568935_G_A | 19 | 27 | 93 | QSISRNHVVDIS**K**SGLITIAGGKWT |
| Rectal | 26516200 | Pat3942— | chr11:3762912G_T | 21 | 34 | 94 | TGLFGQTNTGFG**D**VGSTLFGNNKLT |
| Rectal | 26516200 | Pat3942 | chr16:75631789_C_G | 54 | 83 | 95 | YEIGRQFRNEGI**H**LTHNPEFTTCEF |
| Colon | 26516200 | Pat4007 | chr6:31964329_G_A | 3 | 2 | 96 | PILKEIVEMLFS**H**GLVKVLFATETF |

TABLE 7-continued

List of literature datasets and neoantigens used as benchmark. For each dataset neoantigens with experimentally validated T-cell reactivity are listed. The mutated amino acid is indicated in bold and underlined. For mutations generating two distinct neoantigens due to the presence of two alternative splicing isoforms only the neoantigen with the lower RSUM rank is reported (indicated by a *). Genomic coordinates given are with respect to human genome assembly GRch38/hg38.

| Tumor type | Study PUB MED ID | Patient ID | Mutation ID | RSUM rank (with RNASeq) | RSUM rank (no RNASeq) | SEQ ID NO | NeoAg sequence |
|---|---|---|---|---|---|---|---|
| Colon | 26516200 | Pat4007 | chr17: 75778950_C_T | 6 | 10 | 97 | VKKPHRYRPGTV**T**LREIRRYQKSTE |
| Colon | 26516200 | Pat3995 | Chr17: 80339472_A_G | 13 | 7 | 98 | FVTQKRMEHFYL**S**FYTAEQLVYLST |
| Colon | 26516200 | Pat3995 | chr10: 133293592_G_A | 20 | 11 | 99 | DLSIRELVHRIL**L**VAASYSAVTRFI |
| Colon | 26516200 | Pat3995 | chr12: 25245350_C/T | 28 | 52 | 100 | MTEYKLVVVGA**D**GVGKSALTIQLT |
| Colon | 26516200 | Pat4032 | chr11: 43323614_G/A | 2 | 2 | 101 | DPDCVDRLLQCT**Q**QAVPLFSKNVHS |
| Colon | 26516200 | Pat4032 | chr18: 62830155_G/A | 4 | 9 | 102 | VNRWTRRQVILC**E**TCLIVSSVKDSL |
| Colon | 26516200 | Pat4032 | chr12: 120565120_G/A | 16 | 26 | 103 | RHRYLSHLPLTC**K**FSICELALQPPV |
| Breast | 29867227 | Pat4136 | chr11: 62871652_A/C | 40* | 41* | 104 | LLASSDPPALAS**T**NAEVTGTMSQDT |
| Breast | 29867227 | Pat4136 | chr7: 122320259_C/T | 41 | 44 | 105 | TLNSKTYDTVHR**H**LTVEEATASVSE |
| Breast | 29867227 | Pta4136 | chr8: 11847133_C_G | 47 | 50 | 106 | GYNSYSVSNSEK**H**IMAEIYKNGPVE |
| Breast | 29867227 | Pta4136 | chr9: 111437083_G_A | 53 | 74 | 107 | MPYGYVLNE**F**QS**C**QNSSSAQGSSSN |

TABLE 8

Predicted MHC class I IC50 values (nM) for the 28 neoantigens. Genomic coordinates given are with respect to human genome assembly GRch38/hg38.

| PATID | Mutation ID | Neoantigen | SEQ ID NO | MHC class I allele | best score 9mer | best IC50 9mer (nM) | best score 8-11mer | best IC50 8-11mer (nM) |
|---|---|---|---|---|---|---|---|---|
| Pat3998 | chrX: 152767149_C_T | DSLQLVFGIELMKVDPIGHVYIFAT | 80 | HLA-A*30:02 | 0.3 | 52.24 | 0.3 | 52.24 |
| Pat3998 | chr4: 39862286_G_A | SLLPEFVVPYMIYLLAHDPDFTRSQ | 81 | HLA-C*03:03 | 2.4 | 3.92 | 2.4 | 3.92 |
| Pat3998 | chr17: 61961773_G_A | PHIKSTVSVQIISCQYLLQPVKHED | 82 | HLA-A*30:02 | 0.35 | 39.15 | 0.35 | 39.15 |
| Pat3784 | chrX: 154353082_G_A | VVISQSEIGDASCVRVSGQGLHEGH | 83 | HLA-B*07:02 | 2 | 741.59 | 2 | 741.59 |

TABLE 8-continued

Predicted MHC class I IC50 values (nM) for the 28 neoantigens. Genomic coordinates given are with respect to human genome assembly GRch38/hg38.

| PATID | Mutation ID | Neoantigen | SEQ ID NO | MHC class I allele | best score 9mer | best IC50 9mer(nM) | best score 8-11mer | best IC50 8-11mer (nM) |
|---|---|---|---|---|---|---|---|---|
| Pat3784 | chr21: 33555010_C_T | RKTVRARSRTPSC RSRSHTPSRRRR | 84 | HLA-B*07:02 | 0.5 | 468.72 | 0.5 | 468.72 |
| Pat3784 | chr20: 16378976_A_G | REKQQREALERAP ARLERRHSALQR | 85 | HLA-B*07:02 | 2.3 | 4030.25 | 0.85 | 156.78 |
| Pat3903 | chr10: 69005862_C_T | TLKRQLEHNAYHS IEWAINAATLSQ | 86 | HLA-A*24:02 | 0.55 | 180.52 | 0.55 | 180.52 |
| CTE0010 | chr11: 6641192_G_A | VTVRVADINDHAL AFPQARAALQVP | 87 | HLA-C*03:03 | 33.1 | 16.81 | 33.1 | 16.81 |
| CTE0010 | chr6: 30186007_C_A | RPRRVGIALDYDW GTVTFTNAESQE | 88 | HLA-A*02:01 | 2.3 | 154.56 | 1.15 | 92.02 |
| CTE0011 | chr17: 77482288_G_A | GYVGIDSILEQMH RKAMKQGFEFNI | 89 | HLA-A*11:01 | 0.35 | 20.44 | 0.35 | 20.44 |
| CTE0012 | chr1: 13614365_G_T | IIVGVLLAIGFIC AIIVVVMRKMSG | 90 | HLA-A*02:01 | 0.6 | 32.33 | 0.6 | 32.33 |
| CTE0014 | chr11: 11892058_G_C | PREGSGGSTSDYL SQSYSYSSILNK | 91 | HLA-A*01:01 | 0.15 | 4.13 | 0.15 | 4.13 |
| CTE0019 | chr4: 182799720_C_T | RRAGGAQSWLWFV TVKSLIGKGVML | 92 | HLA-A*02:11 | 2.55 | 5.66 | 2.55 | 5.66 |
| Pat3942 | chr2: 156568935_G_A | QSISRNHVVDISK SGLITIAGGKWT | 93 | HLA-C*16:01 | 7.2 | 930.4 | 7.2 | 930.4 |
| Pat3942 | chr11: 3762912_G_T | TGLFGQTNTGFGD VGSTLFGNNKLT | 94 | HLA-C*16:01 | 2.2 | 184.1 | 2.2 | 184.1 |
| Pat3942 | chr16: 75631789_C_G | YEIGRQFRNEGIH LTHNPEFTTCEF | 95 | HLA-A*29:02 | 4.55 | 4282.32 | 10 | 2679.82 |
| Pat4007 | chr6: 31964329_G_A | PILKEIVEMLFSH GLVKVLFATETF | 96 | HLA-A*03:01 | 0.1 | 6.25 | 0.1 | 6.25 |
| Pat4007 | chr17: 75778950_C_T | VKKPHRYRPGTVT LREIRRYQKSTE | 97 | HLA-C*07:02 | 0.2 | 31 | 0.2 | 31 |
| Pat3995 | chr17: 80339472_A_G | FVTQKRMEHFYLS FYTAEQLVYLST | 98 | HLA-B*18:01 | 0.15 | 5.49 | 0.15 | 5.49 |
| Pat3995 | chr10:133293592_G_A | DLSIRELVHRILL VAASYSAVTRFI | 99 | HLA-A*32:01 | 1.3 | 106.56 | 1.3 | 106.56 |
| Pat3995 | chr12: 25245350_C_T | MTEYKLVVVGADG VGKSALTIQLI | 100 | HLA-C*05:01 | 1.25 | 4671.02 | 1.25 | 4671.02 |
| Pat4032 | chr11:43323614_G_A | DPDCVDRLLQCTQ QAVPLFSKNVHS | 101 | HLA-A*02:13 | 1.1 | 26.4 | 1.1 | 26.4 |
| Pat4032 | chr18: 62830155_G_A | VNRWTRRQVILCE TCLIVSSVKDSL | 102 | HLA-A*02:13 | 2.3 | 120.9 | 2.3 | 120.9 |
| Pat4032 | chr12: 120565120_G_A | RHRYLSHLPLTCK FSICELALQPPV | 103 | HLA-A*03:01 | 1.15 | 339.34 | 3.5 | 190.4 |
| Pat4136 | chr11: 62871652_A_C | LLASSDPPALAST NAEVTGTMSQDT | 104 | HLA-B*35:01 | 4.4 | 1066.8 | 4.4 | 1066.8 |
| Pat4136 | chr7: 122320259_C_T | TLNSKTYDTVHRH LTVEEATASVSE | 105 | HLA-B*57:01 | 1.75 | 1314.73 | 2.1 | 560.5 |
| Pat4136 | chr8: 11847133_C_G | GYNSYSVSNSEKH IMAEIYKNGPVE | 106 | HLA-B*57:01 | 2.5 | 2822.89 | 2.5 | 2822.89 |
| Pat4136 | chr9: 111437083_G_A | MPYGYVLNEFQSC QNSSSAQGSSSN | 107 | HLA-B*35:01 | 19 | 9289.43 | 19 | 9289.43 |

Example 4: Optimization of Neoantigen Layout for Synthetic Genes Encoding Neoantigens to be Delivered by a Genetic Vaccine Vector A polyneoantigen containing 60 neoantigens will result in an artificial protein with a total length of about 1500 amino acids that need to be encoded by an expression cassette inserted into a genetic vaccine vector. Expression of such a long artificial proteins can be suboptimal thus affecting the level of immunogenicity induced against the encoded neoantigens. Splitting the polyneoantigen into two pieces thus could help to obtain higher levels of induced immunogenicity.

A polyneoantigen composed of 62 neoantigens (Table 9) derived from the murine tumor cell line CT26 was therefore tested, using adenoviral vector GAd20, in different layouts (FIGS. 8A and 8B) for its capacity to induce immunogenicity in vivo: in a single vector layout with all 62 neoantigens encoded by a single polyneoantigen (GAd20-CT26-62, SEQ ID NO: 170), in a two vector layout each encoding half of the 62 neoantigens (GAd-CT26-1-31+GAd-CT26-32-62, SEQ ID NOs: 171, 172), and in a third layout with the same two separate expression cassettes present in a single vector (GAd-CT26 dual 1-31 & 32-62). One TPA T-cell enhancer element (SEQ ID NO: 173) was present at the N-terminus of the polyneoantigen containing the 62 neoantogens and one TPA T-cell enhancer element was present at the N-terminus of each of the two 31 neoantigens constructs. A HA peptide sequence (SEQ ID NO: 183) was added at the C-terminal end of the assembled neo-antigens for the purpose of monitoring expression.

Immunogenicity was determined in vivo by immunizing groups (n=6) of naïve BalbC mice intramuscularly once with a dose of 5×10^8 viral particles (vp). T cell responses were measured 2 weeks post immunization on splenocytes by INFγ ELISpot for recognition of peptide pools containing the 25mer neoantigens.

GAd20-CT26-62, expressing the long polyneoantigen, demonstrated a sub-optimal induction of neoantigen specific T cell responses when compared to the co-administered two vector layout GAd-CT26-1-31/GAd-CT26-32-62 (FIG. 8A). Therefore, dividing a long polyneoantigen into two shorter polyneoantigens of approximately equal length provided a significantly improved immunogenic response. Importantly, also the dual cassette vector GAd-CT26 dual 1-31 & 32-62 (FIG. 8B) induced a level of immunogenicity that was significantly higher than that of GAd-CT26-1-62, and comparable to that observed for the combination of two adenoviral vectors GAd-CT26-1-31+GAd-CT26-31-62 (FIGS. 8A & B).

Dividing the long polyantigen into two approximately equally sized smaller polyneoantigens thus provides a vaccine vector composition (one dual cassette vector or two distinct vectors) with superior immunogenic properties.

TABLE 9

List of 62 CT26 neoantigens. The order of the individual neoantigens in the polyneoantigen encoded by the various constructs is shown

| Order GAd-CT26-1-62 | Order GAd-CT26-1-31 | Order GAd-CT26-32-62 | Order dual GAd-CT26-1-31 + GAd-CT26-32-62 | SEQ ID NO | CT26 Neoantigens |
|---|---|---|---|---|---|
| 1 | 1 | | 1 (cassette 1) | 108 | PGPQNFPPQNMFEFPPHLSPPLLPP |
| 2 | 2 | | 2 (cassette 1) | 109 | GAQEEPQVEPLDFSLPKQQGELLER |
| 3 | 3 | | 3 (cassette 1) | 110 | AVFAGSDDPFATPLSMSEMDRRNDA |
| 4 | 4 | | 4 (cassette 1) | 111 | HSGQNHLKEMAISVLEARACAAAGQ |
| 5 | 5 | | 5 (cassette 1) | 112 | ILPQAPSGPSYATYLQPAQAQMLTP |
| 6 | 6 | | 6 (cassette 1) | 113 | MSYAEKSDEITKDEWMEKL |
| 7 | 7 | | 7 (cassette 1) | 114 | GAGKGKYYAVNFSMRDGIDDESYGQ |
| 8 | 8 | | 8 (cassette 1) | 115 | YRGADKLCRKASSVKLVKTSPELSE |
| 9 | 9 | | 9 (cassette 1) | 116 | DSNLQARLTSYETLKKSLSKIREES |
| 10 | 10 | | 10 (cassette 1) | 117 | HSFIHAAMGMAVTWCAAIMTKGQYS |
| 11 | 11 | | 11 (cassette 1) | 118 | LRTAAYVNAIEKIFKVYNEAGVTFT |
| 12 | 12 | | 12 (cassette 1) | 119 | FEGSLAKNLSLNFQAVKENLYYEVG |
| 13 | 13 | | 13 (cassette 1) | 120 | DPRAAYFRQAENDMYIRMALLATVL |
| 14 | 14 | | 14 (cassette 1) | 121 | LRSQMVMKMREYFCNLHGFVDIETP |
| 15 | 15 | | 15 (cassette 1) | 122 | DLLAFERKLDQTVMRKRLDIQEALK |
| 16 | 16 | | 16 (cassette 1) | 123 | IKREKCWKDATYPESFHTLESVPAT |
| 17 | 17 | | 17 (cassette 1) | 124 | GRSSQVYFTINVNLDLSEAAVVTFS |
| 18 | 18 | | 18 (cassette 1) | 125 | KPLRRNNSYTSYIMAICGMPLDSFR |
| 19 | 19 | | 19 (cassette 1) | 126 | TTCLAVGGLDVKFQEAALRAAPDIL |

TABLE 9-continued

List of 62 CT26 neoantigens. The order of the individual neoantigens in the polyneoantigen encoded by the various constructs is shown

| Order GAd-CT26-1-62 | Order GAd-CT26-1-31 | Order GAd-CT26-32-62 | Order dual GAd-CT26-1-31 + GAd-CT26-32-62 | SEQ ID NO | CT26 Neoantigens |
|---|---|---|---|---|---|
| 20 | 20 | | 20 (cassette 1) | 127 | IYEFDYHLYGQNITMIMTSVSGHLL |
| 21 | 21 | | 21 (cassette 1) | 128 | PDSFSIPYLTALDDLLGTALLALSF |
| 22 | 22 | | 22 (cassette 1) | 129 | YATILEMQAMMTLDPQDILLAGNMM |
| 23 | 23 | | 23 (cassette 1) | 130 | SWIHCWKYLSVQSQLFRGSSLLFRR |
| 24 | 24 | | 24 (cassette 1) | 131 | YDNKGITYLFDLYYESDEFTVDAAR |
| 25 | 25 | | 25 (cassette 1) | 132 | AQAAKNKGNKYFQAGKYEQAIQCYT |
| 26 | 26 | | 26 (cassette 1) | 133 | QPMLPIGLSDIPDEAMVKLYCPKCM |
| 27 | 27 | | 27 (cassette 1) | 134 | HRGAIYGSSWKYFTFSGYLLYQD |
| 28 | 28 | | 28 (cassette 1) | 135 | VIQTSKYYMRDVIAIESAWLLELAP |
| 29 | 29 | | 29 (cassette 1) | 136 | PRGVDLYLRILMPIDSELVDRDVVH |
| 30 | 30 | | 30 (cassette 1) | 137 | QIEQDALCPQDTYCDLKSRAEVNGA |
| 31 | 31 | | 31 (cassette 1) | 138 | ALASAILSDPESYIKKLKELRSMLM |
| 32 | | 1 | 1 (cassette 2) | 139 | VIVLDSSQGNSVCQIAMVHYIKQKY |
| 33 | | 2 | 2 (cassette 2) | 140 | MKSVSIQYLEAVKRLKSEGHRFPRT |
| 34 | | 3 | 3 (cassette 2) | 141 | KGGPVKIDPLALMQAIERYLVVRGY |
| 35 | | 4 | 4 (cassette 2) | 142 | LQDDPDLQALLKASQLLKVKSSSWR |
| 36 | | 5 | 5 (cassette 2) | 143 | LIAHMILGYRYWTGIGVLQSCESAL |
| 37 | | 6 | 6 (cassette 2) | 144 | TSVDQHLAPGAVAMPQAASLHAVIV |
| 38 | | 7 | 7 (cassette 2) | 145 | EISVRIATIPAFDTIMETVIQRELL |
| 39 | | 8 | 8 (cassette 2) | 146 | KTSREIKISGAIEPCVSLNSKGPCV |
| 40 | | 9 | 9 (cassette 2) | 147 | QGLANYVITTMGTICAPVRDEDIRE |
| 41 | | 10 | 10 (cassette 2) | 148 | ELSRRQYAEQELKQVRMALKKAEKE |
| 42 | | 11 | 11 (cassette 2) | 149 | IETQQRKFKASRASILSEMKMLKEK |
| 43 | | 12 | 12 (cassette 2) | 150 | SIFLDDDSNQPMAVSRFFGNVELMQ |
| 44 | | 13 | 13 (cassette 2) | 151 | RPDSYVRDMEIEAASHHVYADQPHI |
| 45 | | 14 | 14 (cassette 2) | 152 | TLSAMSNPRAMQVLLQIQQGLQTLA |
| 46 | | 15 | 15 (cassette 2) | 153 | VMKGTLEYLMSNTPTAQSLRESYIF |
| 47 | | 16 | 16 (cassette 2) | 154 | AAELFHQLSQALKVLTDAAARAAYD |
| 48 | | 17 | 17 (cassette 2) | 155 | TGLYFRKSYYMQKYFLDTVTEDAKV |
| 49 | | 18 | 18 (cassette 2) | 156 | CRNNVHYLNDGDAIIYHTASIGILH |
| 50 | | 19 | 19 (cassette 2) | 157 | DINDNNPSFPTGKMKLEISEALAPG |
| 51 | | 20 | 20 (cassette 2) | 158 | REGILQEESIYKPQKQEQELRALQA |
| 52 | | 21 | 21 (cassette 2) | 159 | INPTMIISNTLSKSAIATPKISYLL |
| 53 | | 22 | 22 (cassette 2) | 160 | QDLHNLNLLSLYANKLQTVAKGTFS |
| 54 | | 23 | 23 (cassette 2) | 161 | QEIQTYAIALINVLFLKAPEDKRQD |
| 55 | | 24 | 24 (cassette 2) | 162 | CYNYLYRMKALDGIRASEIPFHAEG |

TABLE 9-continued

List of 62 CT26 neoantigens. The order of the individual neoantigens in the polyneoantigen encoded by the various constructs is shown

| Order GAd-CT26-1-62 | Order GAd-CT26-1-31 | Order GAd-CT26-32-62 | Order dual GAd-CT26-1-31 + GAd-CT26-32-62 | SEQ ID NO | CT26 Neoantigens |
|---|---|---|---|---|---|
| 56 | | 25 | 25 (cassette 2) | 163 | QSIHSFQSLEESISVLPSFQEPHLQ |
| 57 | | 26 | 26 (cassette 2) | 164 | TDFCLRNLDGTLCYLLDKETLRLHP |
| 58 | | 27 | 27 (cassette 2) | 165 | CEVTRVKAVRILPCGVAKVLWMQGS |
| 59 | | 28 | 28 (cassette 2) | 166 | GYDSRSARAFPYANVAFPHLTSSAP |
| 60 | | 29 | 29 (cassette 2) | 167 | TDKELREAMALLAAQQTALEVIVNM |
| 61 | | 30 | 30 (cassette 2) | 168 | LSRPDLPFLIAAVFFLVVAVWGETL |
| 62 | | 31 | 31 (cassette 2) | 169 | LYYTTVRALTRHNTMLKAMFSGRME |

REFERENCES

Andersen R S, Kvistborg P, Frøsig T M, Pedersen N W, Lyngaa R, Bakker A H, Shu C J, Straten Pt, Schumacher T N, Hadrup S R. (2012). Parallel detection of antigen-specific T cell responses by combinatorial encoding of MHC multimers. Nat Protoc, 7(5), 891-902. doi:10.1038/nprot.2012.037

Andreatta M & Nielsen M. (2016). Gapped sequence alignment using artificial neural networks: application to the MHC class I system. Bioinformatics, 32(4), 511-517. doi:10.1093/bioinformatics/btv639

Andrews, S. FastQC A Quality Control tool for High Throughput Sequence Data. Available online at: bioinformatics.babraham.ac.uk/projects/fastqc.

Bolger A M, Lohse M, Usadel B. (2014). Trimmomatic: a flexible trimmer for Illumina sequence data. Bioinformatics, 30(15), 2114-2120. doi:10.1093/bioinformatics/btu170

Cibulskis Kl, Lawrence M S, Carter S L, Sivachenko A, Jaffe D, Sougnez C, Gabriel S, Meyerson M, Lander E S, Getz G. (2013). Sensitive detection of somatic point mutations in impure and heterogeneous cancer samples. Nat Biotechnol, 31(3), 213-219. doi:10.1038/nbt.2514

Donnelly M L, Hughes L E, Luke G, Mendoza H, ten Dam E, Gani D, Ryan M D. (2001) The 'cleavage' activities of foot-and-mouth disease virus 2A site-directed mutants and naturally occurring '2A-like' sequences. J Gen Virol. 200182(Pt 5):1027-41.

Fang H, Wu Y, Narzisi G, O'Rawe J A, Barrón L T, Rosenbaum J, Ronemus M, Iossifov I, Schatz M C, Lyon G J. (2014). Reducing INDEL calling errors in whole genome and exome sequencing data. Genome Med, 6(10), 89. doi:10.1186/s13073-014-0089-z Fritsch E F, Rajasagi M, Ott P A, Brusic V, Hacohen N, Wu C J. (2014). HLA-binding properties of tumor neoepitopes in humans. Cancer Immunol Res, 2(6), 522-529. doi:10.1158/2326-6066.CIR-13-0227

Gros A, Parkhurst M R, Tran E, Pasetto A, Robbins P F, Ilyas S, Prickett T D, Gartner J J, Crystal J S, Roberts I M, Trebska-McGowan K, Wunderlich J R, Yang J C1, Rosenberg S A. (2016). Prospective identification of neoantigen-specific lymphocytes in the peripheral blood of melanoma patients. Nat Med. 22(4):433-8. doi: 10.1038/nm.4051.

Hoof I, Peters B, Sidney J, Pedersen L E, Sette A, Lund O, Buus S, Nielsen M. (2009). NetMHCpan, a method for MHC class I binding prediction beyond humans. Immunogenetics, 61(1), 1-13. doi:10.1007/s00251-008-0341-z Jurtz V, Paul S, Andreatta M, Marcatili P, Peters B, Nielsen M. (2017). NetMHCpan-4.0: Improved Peptide-MHC Class I Interaction Predictions Integrating Eluted Ligand and Peptide Binding Affinity Data. J Immunol, 199(9), 3360-3368. doi:10.4049/jimmunol.1700893

Kandoth C, McLellan M D, Vandin F, Ye K, Niu B, Lu C, Xie M, Zhang Q, McMichael J F, Wyczalkowski M A, Leiserson M D M, Miller C A, Welch J S, Walter M J, Wendl M C, Ley T J, Wilson R K, Raphael B J, Ding L. (2013). Mutational landscape and significance across 12 major cancer types. Nature, 502(7471), 333-339. doi:10.1038/nature12634

Kim D, Langmead B, Salzberg S L. (2015). HISAT: a fast spliced aligner with low memory requirements. Nat Methods, 12(4), 357-360. doi:10.1038/nmeth.3317

Koboldt D C, Zhang Q, Larson D E, Shen D, McLellan M D, Lin L, Miller C A, Mardis E R, Ding L, Wilson R K. (2012). VarScan 2: somatic mutation and copy number alteration discovery in cancer by exome sequencing. Genome Res, 22(3), 568-576. doi:10.1101/gr.129684.111

Li B & Dewey C N. (2011). RSEM: accurate transcript quantification from RNA-Seq data with or without a reference genome. BMC Bioinformatics, 12, 323. doi:10.1186/1471-2105-12-323

Li H & Durbin R. (2009). Fast and accurate short read alignment with Burrows-Wheeler transform. Bioinformatics, 25(14), 1754-1760. doi:10.1093/bioinformatics/btp324

Li H, Handsaker B, Wysoker A, Fennell T, Ruan J, Homer N, Marth G, Abecasis G, Durbin R; 1000 Genome Project Data Processing Subgroup. Genome Project Data Processing, S. (2009). The Sequence Alignment/Map format and SAMtools. Bioinformatics, 25(16), 2078-2079. doi:10.1093/bioinformatics/btp352

Luke G A, de Felipe P, Lukashev A, Kallioinen S E, Bruno E A, Ryan M D. (2008) Occurrence, function and evolutionary origins of '2A-like' sequences in virus genomes. J Gen Virol. 2008 89(Pt 4):1036-42. doi: 10.1099/vir.0.83428-0.

Lundegaard C, Lamberth K, Harndahl M, Buus S, Lund O, Nielsen M. (2008). NetMHC-3.0: accurate web accessible predictions of human, mouse and monkey MHC class I affinities for peptides of length 8-11. Nucleic Acids Res, 36(Web Server issue), W509-512. doi:10.1093/nar/gkn202

McKenna A, Hanna M, Banks E, Sivachenko A, Cibulskis K, Kernytsky A, Garimella K, Altshuler D, Gabriel S, Daly M, DePristo M A. (2010). The Genome Analysis Toolkit: a MapReduce framework for analyzing next-generation DNA sequencing data. Genome Res, 20(9), 1297-1303. doi:10.1101/gr.107524.110

Moutaftsi M, Peters B, Pasquetto V, Tscharke D C, Sidney J, Bui H H, Grey H, Sette A. (2006). A consensus epitope prediction approach identifies the breadth of murine T(CD8+)-cell responses to vaccinia virus. Nat Biotechnol, 24(7), 817-819. doi:10.1038/nbt1215

Sahin U, Derhovanessian E, Miller M, Kloke B P, Simon P, Löwer M, Bukur V, Tadmor A D, Luxemburger U, Schrörs B, Omokoko T, Vormehr M, Albrecht C, Paruzynski A, Kuhn A N, Buck J, Heesch S, Schreeb K H, Müller F, Ortseifer I, Vogler I, Godehardt E, Attig S, Rae R, Breitkreuz A, Tolliver C, Suchan M, Martic G, Hohberger A, Sorn P, Diekmann J, Ciesla J, Waksmann O, Brück A K, Witt M, Zillgen M, Rothermel A, Kasemann B, Langer D, Bolte S, Diken M, Kreiter S, Nemecek R, Gebhardt C, Grabbe S, Höller C, Utikal J, Huber C, Loquai C, Türeci Ö. Personalized RNA mutanome vaccines mobilize poly-specific therapeutic immunity against cancer. Nature, 547 (7662), 222-226. doi:10.1038/nature23003

Shannon, C. E. (1997). The mathematical theory of communication. 1963. M D Comput, 14(4), 306-317.

Strait & Dewey. (1996). The Shannon information entropy of protein sequences. Biophys. J. 1996 Biophys J. 71(1), 148-55.

Szolek A, Schubert B, Mohr C, Sturm M, Feldhahn M, Kohlbacher O. (2014). OptiType: precision HLA typing from next-generation sequencing data. Bioinformatics, 30(23), 3310-3316. doi:10.1093/bioinformatics/btu548

Tran E, Ahmadzadeh M, Lu Y C, Gros A, Turcotte S, Robbins P F, Gartner J J, Zheng Z, Li Y F, Ray S, Wunderlich J R, Somerville R P, Rosenberg S A. (2015). Immunogenicity of somatic mutations in human gastrointestinal cancers. Science, 350(6266), 1387-1390. doi:10.1126/science.aad1253

Wang K, Li M, Hakonarson H. (2010). ANNOVAR: functional annotation of genetic variants from high-throughput sequencing data. Nucleic Acids Res, 38(16), e164. doi:10.1093/nar/gkq603

Warren R L, Choe G, Freeman D J, Castellarin M, Munro S, Moore R, Holt R A. (2012). Derivation of HLA types from shotgun sequence datasets. Genome Med, 4(12), 95. doi:10.1186/gm396

Yarchoan M, Johnson B A 3rd, Lutz E R, Laheru D A, Jaffee E M. (2017). Targeting neoantigens to augment antitumour immunity. Nat Rev Cancer, 17(9), 569. doi:10.1038/nrc.2017.74

The invention claimed is:

1. A method for treating or limiting development of cancer comprising preparing a personalized vector vaccine encoding cancer neoantigens comprising the steps of:

(a) determining neoantigens in a sample of cancerous cells, wherein each neoantigen is comprised within a coding sequence, comprises at least one mutations in the coding sequence resulting in a change of the encoded amino acid sequence that is not present in a sample of non-cancerous cells of said individual, and consists of 9 to 40 contiguous amino acids of the coding sequence in the sample of cancerous cells, (b) determining for each neoantigen the mutation allele frequency of each of said mutations of step (a) within the coding sequence, (c) determining the expression level of each coding sequence comprising at least one of said mutations, (i) in said sample of cancerous cells, or (ii) from an expression database of the same cancer type as the sample of cancerous cells, (d) predicting the MHC class I binding affinity of the neoantigens, wherein (I) the HLA class I alleles are determined from the sample of non-cancerous cells of said individual, (II) for each HLA class I allele determined in (I) the MHC class I binding affinity of each fragment consisting of 8 to 15 contiguous amino acids of the neoantigen is predicted, wherein each fragment is comprising at least one amino acid change caused by the mutation of step (a), and (III) the fragment with the highest MHC class I binding affinity determines the MHC class I binding affinity of the neoantigen, and in addition to or alternatively to step (d), (d'):

determining the HLA class II alleles in the sample of non-cancerous cells of said individual, predicting the MHC class II binding affinity of the neoantigen, wherein for each HLA class II allele determined the MHC class II binding affinity for each fragment of 11 to 30 contiguous amino acids of the neoantigen is predicted, wherein each fragment is comprising at least one mutated amino acid generated by the mutation of step (a), and the fragment with the highest MHC class II binding affinity determines the MHC class II binding affinity of the neoantigen;

(e) ranking the neoantigens according to the values of mutation allele frequency, expression level, and binding affinity of MHC class I and/or MHC class II determined in steps (b), (c), (d) and/or (d'), respectively, for each neoantigen from highest to lowest values, yielding, respectively, a first, a second, a third, and/or a fourth list of ranks, (f) calculating a rank sum from said first, second, third, and/or fourth list of ranks, wherein the rank sum is a weighted rank sum, wherein the number of neoantigens determined in step (a) is added to the rank value of each neoantigen:

in the third list of ranks for which the prediction of MHC class I binding affinity of step (d) resulted in an IC50 value higher than 1000 nM and/or in the fourth list of ranks for which the prediction of MHC class II binding affinity of step (d') resulted in an IC50 value higher than 1000 nM;

and/or in case of step (c) (i) being performed by massively parallel transcriptome sequencing, the rank sum of step (f) is multiplied by a weighing factor (WF), wherein WF is 1, if the number of mapped transcriptome reads for the mutation is >0, 2, if the number of mapped transcriptome reads for the mutation is 0 and the number of mapped reads for the non-mutated sequence is 0 and the transcripts-per-million (TPM) value is at least 0.5, 3, if the number of mapped transcriptome reads for the mutation is 0 and the number of mapped reads for the non-mutated sequence is >0 and the transcripts-per-million (TPM) value is at least 0.5, 4, if the number of mapped transcriptome reads for the mutation is 0 and the number of mapped reads for the non-mutated sequence is 0 and the transcripts-per-million (TPM) value is <0.5, or 5, if the number of mapped transcriptome reads for the mutation is 0 and the number of mapped reads for the non-mutated sequence is >0 and the transcripts-per-million (TPM) value is <0.5; and ordering the neoantigens by increasing weighted rank sum, yielding a ranked list of neoantigens;

(g) selecting 30-240 neoantigens from the ranked list of neoantigens obtained in (f) starting with the lowest rank; and (h) administering a vector encoding at least one of the 30-240 neoantigens selected in step (g) or a collection of vectors encoding each a portion of the 30-240 selected in step (g).

2. The method according to claim 1, wherein steps (a) and (d) (I) are performed using massively parallel DNA sequencing of the samples and wherein the number of reads comprising the mutation at the chromosomal position of the identified mutation is:

in the sample of cancerous cells at least 2, in the sample of non-cancerous cells is 2 or less.

3. The method of claim 1, wherein the at least one mutation of step (a) is a single nucleotide variant (SNV) or an insertion/deletion mutation resulting in a frame-shift peptide (FSP).

4. The method according to claim 3, wherein the mutation is a SNV and the neoantigen has the total size defined in step (a) and consists of the amino acid caused by the mutation, flanked on each side by a number of adjoining contiguous amino acids, wherein the number on each side does not differ by more than one unless the coding sequence does not comprise a sufficient number of amino acids on either side, wherein the neoantigen has the total size defined in step (a).

5. The method according to claim 3, wherein the mutation results in a FSP and each single amino acid change caused by the mutation results in a neoantigen that has the total size defined in step (a) and consists of:

(i) said single amino acid change caused by the mutation and 7 to 14 N-terminally adjoining contiguous amino acids, and (ii) a number of contiguous amino acids adjoining the fragment of step (i) on either side, wherein the number of amino acids on either side differ by not more than one, unless the coding sequence does not comprise a sufficient number of amino acids on either side, wherein the MHC class I binding affinity of step (d) and/or the MHC class II binding affinity of step (d') is predicted for the fragment of step (i).

6. The method according to claim 1, wherein the mutation allele frequency of the neoantigen determined in step (b) in the sample of cancerous cells is at least 2%.

7. The method according to claim 1, wherein step (g) further comprises removing neoantigens from genes linked to autoimmune disease, and/or neoantigens with a Shannon entropy value for their amino acid sequence lower than 0.1 from said ranked list of neoantigens.

8. The method according to claim 1, wherein the expression level of said coding genes in step (c) (i) is determined by massively parallel transcriptome sequencing and wherein the expression level determined in step (c) (i) uses a corrected Transcripts Per Kilobase Million (corrTPM) value calculated according to the following formula $$\text{corrTPM}=TPM*((M+c)/(M+W+c))$$

wherein M is the number of reads spanning the location of the mutation of step (a) that comprise the mutation and W is the number of reads spanning the location of the mutation of step (a) without the mutation and TPM is the Transcripts Per Kilobase Million value of the gene comprising the mutation and the c is a constant larger than 0.

9. The method according to claim 1, wherein step (g) comprises an alternative selection process, wherein the neoantigens are selected from the ranked list of neoantigens starting with the lowest rank until a set maximum size in total overall length in amino acids for all selected neoantigens is reached, wherein the maximum size is between 1200 and 1800 amino acids for each vector of a monovalent or multivalent vaccine; and optionally wherein two or more neoantigens are merged into one new neoantigen if they comprise overlapping amino acid sequence segments.

10. A method for treating or limiting development of cancer comprising constructing a personalized vector encoding a combination of neoantigens according to claim 1 for use as a vaccine, comprising the steps of:

(i) determining and selecting cancer neoantigens according to the steps (a)-(g) of the method of claim 1 to obtain a list of neoantigens, and ordering the list of neoantigens in at least 105-108 different combinations, (ii) generating all possible pairs of neoantigen junction segments for each combination, wherein each junction segment comprises 15 adjoining contiguous amino acids on either side of the junction, (iii) predicting the MHC class I and/or class II binding affinity for all epitopes in junction segments wherein only HLA alleles are tested that are present in the individual the vector is designed for, and (iv) selecting the combination of neoantigens with the lowest number of junctional epitopes with an IC50 of ≤1500 nM and wherein if multiple combinations have the same lowest number of junctional epitopes the combination first encountered is selected;

(v) constructing a personalized vector comprising the selected combination of neoantigens of step (iv) or a collection of personalized vectors encoding each a portion of the combination of neoantigens of step (iv); and (vi) administering the personalized vector or collection of personalized vectors of step (v).

* * * * *

SEQUENCE LISTING

```
<160> NUMBER OF SEQ ID NOS: 184

<210> SEQ ID NO 1
<211> LENGTH: 98
<212> TYPE: PRT
<213> ORGANISM: Artificial Sequence
<220> FEATURE:
<223> OTHER INFORMATION: complete FSP

<400> SEQUENCE: 1

Gly Ser Leu Ser Gly Tyr Leu Ser Gln Asp Thr Val Gly Ala Leu Pro
1               5                   10                  15

Val Ser Val Val Ser Leu Cys Pro Gly Arg Cys Gln Ser Gly Glu Ala
            20                  25                  30

Gly Leu Trp Gly Gly His Gln Ala Ala Arg His His Leu His Arg Ser
        35                  40                  45

Gln Val Arg Trp His Pro Gly His Gly Leu Pro Pro His Leu Arg Gln
    50                  55                  60

Gln Arg Ala Ala Arg Leu Arg Gln Pro Asp Ala Ala Glu Ala Gly Gly
65                  70                  75                  80

Pro Glu His Leu Leu Leu Leu Pro Glu Gln Gly Pro Arg Cys Ala Ala
                85                  90                  95

Trp Gly


<210> SEQ ID NO 2
<211> LENGTH: 30
<212> TYPE: PRT
<213> ORGANISM: Artificial Sequence
<220> FEATURE:
<223> OTHER INFORMATION: Assembled FSP

<400> SEQUENCE: 2

Gly Ser Leu Ser Gly Tyr Leu Ser Gln Asp Thr Val Gly Ala Leu Pro
```

```
1               5                   10                  15

Val Ser Val Val Ser Leu Cys Pro Gly Arg Cys Gln Ser Gly
            20                  25                  30


<210> SEQ ID NO 3
<211> LENGTH: 23
<212> TYPE: PRT
<213> ORGANISM: Artificial Sequence
<220> FEATURE:
<223> OTHER INFORMATION: FSP fragment

<400> SEQUENCE: 3

Gly Ser Leu Ser Gly Tyr Leu Ser Gln Asp Thr Val Gly Ala Leu Pro
1               5                   10                  15

Val Ser Val Val Ser Leu Cys
            20


<210> SEQ ID NO 4
<211> LENGTH: 25
<212> TYPE: PRT
<213> ORGANISM: Artificial Sequence
<220> FEATURE:
<223> OTHER INFORMATION: FSP fragment

<400> SEQUENCE: 4

Leu Ser Gly Tyr Leu Ser Gln Asp Thr Val Gly Ala Leu Pro Val Ser
1               5                   10                  15

Val Val Ser Leu Cys Pro Gly Arg Cys
            20                  25


<210> SEQ ID NO 5
<211> LENGTH: 25
<212> TYPE: PRT
<213> ORGANISM: Artificial Sequence
<220> FEATURE:
<223> OTHER INFORMATION: FSP fragment

<400> SEQUENCE: 5

Ser Gly Tyr Leu Ser Gln Asp Thr Val Gly Ala Leu Pro Val Ser Val
1               5                   10                  15

Val Ser Leu Cys Pro Gly Arg Cys Gln
            20                  25


<210> SEQ ID NO 6
<211> LENGTH: 25
<212> TYPE: PRT
<213> ORGANISM: Artificial Sequence
<220> FEATURE:
<223> OTHER INFORMATION: FSP fragment

<400> SEQUENCE: 6

Tyr Leu Ser Gln Asp Thr Val Gly Ala Leu Pro Val Ser Val Val Ser
1               5                   10                  15

Leu Cys Pro Gly Arg Cys Gln Ser Gly
            20                  25


<210> SEQ ID NO 7
<211> LENGTH: 25
<212> TYPE: PRT
<213> ORGANISM: Artificial Sequence
<220> FEATURE:
<223> OTHER INFORMATION: FSP fragment

<400> SEQUENCE: 7
```

Pro Gly His Gly Leu Pro Pro His Leu Arg Gln Gln Arg Ala Ala Arg
1 5 10 15

Leu Arg Gln Pro Asp Ala Ala Glu Ala
20 25

<210> SEQ ID NO 8
<211> LENGTH: 18
<212> TYPE: PRT
<213> ORGANISM: Artificial Sequence
<220> FEATURE:
<223> OTHER INFORMATION: FSP fragment

<400> SEQUENCE: 8

Pro Glu His Leu Leu Leu Leu Pro Glu Gln Gly Pro Arg Cys Ala Ala
1 5 10 15

Trp Gly

<210> SEQ ID NO 9
<211> LENGTH: 31
<212> TYPE: PRT
<213> ORGANISM: Artificial Sequence
<220> FEATURE:
<223> OTHER INFORMATION: complete FSP

<400> SEQUENCE: 9

Ala Arg Pro Pro Gly Ser Val Glu Asp Ala Gly Gln Ala Val Gly His
1 5 10 15

Ile Leu Ala Gln Ala Cys Val Tyr Arg Ala Val Gln Cys Ser Arg
20 25 30

<210> SEQ ID NO 10
<211> LENGTH: 22
<212> TYPE: PRT
<213> ORGANISM: Artificial Sequence
<220> FEATURE:
<223> OTHER INFORMATION: FSP fragment

<400> SEQUENCE: 10

Ala Arg Pro Pro Gly Ser Val Glu Asp Ala Gly Gln Ala Val Gly His
1 5 10 15

Ile Leu Ala Gln Ala Cys
20

<210> SEQ ID NO 11
<211> LENGTH: 24
<212> TYPE: PRT
<213> ORGANISM: Artificial Sequence
<220> FEATURE:
<223> OTHER INFORMATION: FSP fragment

<400> SEQUENCE: 11

Glu Asp Ala Gly Gln Ala Val Gly His Ile Leu Ala Gln Ala Cys Val
1 5 10 15

Tyr Arg Ala Val Gln Cys Ser Arg
20

<210> SEQ ID NO 12
<211> LENGTH: 25
<212> TYPE: PRT
<213> ORGANISM: Artificial Sequence
<220> FEATURE:
<223> OTHER INFORMATION: neoantigen

<400> SEQUENCE: 12

Tyr Ile Arg Leu Val Glu Pro Gly Ser Pro Ala Glu Asn Ala Gly Leu
1 5 10 15

Leu Ala Gly Asp Arg Leu Val Glu Val
20 25

<210> SEQ ID NO 13
<211> LENGTH: 25
<212> TYPE: PRT
<213> ORGANISM: Artificial Sequence
<220> FEATURE:
<223> OTHER INFORMATION: neoantigen

<400> SEQUENCE: 13

Tyr Phe Trp Asn Ile Ala Thr Ile Ala Val Phe Tyr Val Leu Pro Val
1 5 10 15

Val Gln Leu Val Ile Thr Tyr Gln Thr
20 25

<210> SEQ ID NO 14
<211> LENGTH: 25
<212> TYPE: PRT
<213> ORGANISM: Artificial Sequence
<220> FEATURE:
<223> OTHER INFORMATION: neoantigen

<400> SEQUENCE: 14

Val Thr Leu Glu Asp Phe Tyr Gly Val Phe Ser Ser Leu Gly Tyr Thr
1 5 10 15

His Leu Ala Ser Val Ser His Pro Gln
20 25

<210> SEQ ID NO 15
<211> LENGTH: 25
<212> TYPE: PRT
<213> ORGANISM: Artificial Sequence
<220> FEATURE:
<223> OTHER INFORMATION: neoantigen

<400> SEQUENCE: 15

Glu Lys Cys Gln Phe Ala His Gly Phe His Glu Leu Cys Ser Leu Thr
1 5 10 15

Arg His Pro Lys Tyr Lys Thr Glu Leu
20 25

<210> SEQ ID NO 16
<211> LENGTH: 25
<212> TYPE: PRT
<213> ORGANISM: Artificial Sequence
<220> FEATURE:
<223> OTHER INFORMATION: neoantigen

<400> SEQUENCE: 16

Thr Pro Asp Phe Thr Ser Leu Asp Val Leu Thr Phe Val Gly Ser Gly
1 5 10 15

Ile Pro Ala Gly Ile Asn Ile Pro Asn
20 25

<210> SEQ ID NO 17
<211> LENGTH: 25
<212> TYPE: PRT
<213> ORGANISM: Artificial Sequence
<220> FEATURE:
<223> OTHER INFORMATION: neoantigen

<400> SEQUENCE: 17

```
Ser Ala Phe Gly Ala Gly Phe Cys Thr Thr Val Ile Thr Ser Pro Val
1               5                   10                  15

Asp Val Val Lys Thr Arg Tyr Met Asn
            20                  25


<210> SEQ ID NO 18
<211> LENGTH: 25
<212> TYPE: PRT
<213> ORGANISM: Artificial Sequence
<220> FEATURE:
<223> OTHER INFORMATION: neoantigen

<400> SEQUENCE: 18

Glu Ser Leu His Ser Ile Leu Ala Gly Ser Asp Met Met Val Ser Gln
1               5                   10                  15

Ile Leu Leu Thr Gln His Gly Ile Pro
            20                  25


<210> SEQ ID NO 19
<211> LENGTH: 25
<212> TYPE: PRT
<213> ORGANISM: Artificial Sequence
<220> FEATURE:
<223> OTHER INFORMATION: neoantigen

<400> SEQUENCE: 19

Ala Met Arg Leu Leu His Asp Gln Val Gly Val Ile Leu Phe Gly Pro
1               5                   10                  15

Tyr Lys Gln Leu Phe Leu Gln Thr Tyr
            20                  25


<210> SEQ ID NO 20
<211> LENGTH: 25
<212> TYPE: PRT
<213> ORGANISM: Artificial Sequence
<220> FEATURE:
<223> OTHER INFORMATION: neoantigen

<400> SEQUENCE: 20

Ala Pro Thr Glu His Lys Ala Leu Val Ser His Asn Ala Ser Leu Ile
1               5                   10                  15

Asn Val Gly Ser Leu Leu Gln Arg Ala
            20                  25


<210> SEQ ID NO 21
<211> LENGTH: 25
<212> TYPE: PRT
<213> ORGANISM: Artificial Sequence
<220> FEATURE:
<223> OTHER INFORMATION: neoantigen

<400> SEQUENCE: 21

Leu Pro Arg Gly Leu Ser Leu Ser Ser Leu Gly Ser Val Arg Thr Leu
1               5                   10                  15

Arg Gly Trp Ser Arg Ser Ser Arg Pro
            20                  25


<210> SEQ ID NO 22
<211> LENGTH: 25
<212> TYPE: PRT
<213> ORGANISM: Artificial Sequence
<220> FEATURE:
<223> OTHER INFORMATION: neoantigen
```

<400> SEQUENCE: 22

Glu Arg Trp Glu Asp Val Lys Glu Glu Met Thr Ser Asp Leu Ala Thr
1 5 10 15

Met Arg Val Asp Tyr Glu Gln Ile Lys
20 25

<210> SEQ ID NO 23
<211> LENGTH: 25
<212> TYPE: PRT
<213> ORGANISM: Artificial Sequence
<220> FEATURE:
<223> OTHER INFORMATION: neoantigen

<400> SEQUENCE: 23

Leu Tyr Ser Cys Ile Ala Leu Lys Val Thr Ala Asn Lys Met Glu Met
1 5 10 15

Glu His Ser Leu Ile Leu Asn Asn Leu
20 25

<210> SEQ ID NO 24
<211> LENGTH: 25
<212> TYPE: PRT
<213> ORGANISM: Artificial Sequence
<220> FEATURE:
<223> OTHER INFORMATION: neoantigen

<400> SEQUENCE: 24

Leu Val Leu Ser Leu Val Phe Ile Cys Phe Tyr Ile Arg Lys Ile Asn
1 5 10 15

Pro Leu Lys Glu Lys Ser Ile Ile Leu
20 25

<210> SEQ ID NO 25
<211> LENGTH: 22
<212> TYPE: PRT
<213> ORGANISM: Artificial Sequence
<220> FEATURE:
<223> OTHER INFORMATION: neoantigen

<400> SEQUENCE: 25

Pro Phe Ser Thr Leu Thr Pro Arg Leu His Leu Pro Tyr Pro Gln Gln
1 5 10 15

Pro Pro Gln Gln Gln Leu
20

<210> SEQ ID NO 26
<211> LENGTH: 25
<212> TYPE: PRT
<213> ORGANISM: Artificial Sequence
<220> FEATURE:
<223> OTHER INFORMATION: neoantigen

<400> SEQUENCE: 26

Ala Ala Asn Ile Pro Arg Ser Ile Ser Ser Asp Gly His Pro Leu Glu
1 5 10 15

Arg Arg Leu Ser Pro Gly Ser Asp Ile
20 25

<210> SEQ ID NO 27
<211> LENGTH: 25
<212> TYPE: PRT
<213> ORGANISM: Artificial Sequence
<220> FEATURE:
<223> OTHER INFORMATION: neoantigen

<400> SEQUENCE: 27

Tyr Tyr Ile Val Arg Val Leu Gly Thr Leu Gly Ile Met Thr Val Phe
1               5                   10                  15

Trp Val Cys Pro Leu Thr Ile Phe Asn
            20                  25

<210> SEQ ID NO 28
<211> LENGTH: 25
<212> TYPE: PRT
<213> ORGANISM: Artificial Sequence
<220> FEATURE:
<223> OTHER INFORMATION: neoantigen

<400> SEQUENCE: 28

Trp Gln Leu Arg Phe Ser His Leu Val Gly Tyr Gly Gly Arg Tyr Tyr
1               5                   10                  15

Ser Tyr Leu Met Ser Arg Ala Val Ala
            20                  25

<210> SEQ ID NO 29
<211> LENGTH: 25
<212> TYPE: PRT
<213> ORGANISM: Artificial Sequence
<220> FEATURE:
<223> OTHER INFORMATION: neoantigen

<400> SEQUENCE: 29

His Tyr Thr Gln Ser Glu Thr Glu Phe Leu Leu Ser Ser Ala Glu Thr
1               5                   10                  15

Asp Glu Asn Glu Thr Leu Asp Tyr Glu
            20                  25

<210> SEQ ID NO 30
<211> LENGTH: 25
<212> TYPE: PRT
<213> ORGANISM: Artificial Sequence
<220> FEATURE:
<223> OTHER INFORMATION: neoantigen

<400> SEQUENCE: 30

Gln Ser Ile Ser Arg Asn His Val Val Asp Ile Ser Lys Ser Gly Leu
1               5                   10                  15

Ile Thr Ile Ala Gly Gly Lys Trp Thr
            20                  25

<210> SEQ ID NO 31
<211> LENGTH: 25
<212> TYPE: PRT
<213> ORGANISM: Artificial Sequence
<220> FEATURE:
<223> OTHER INFORMATION: neoantigen

<400> SEQUENCE: 31

Leu Leu Gln Cys Val Gln Lys Met Ala Asp Gly Leu Gln Glu Gln Gln
1               5                   10                  15

Gln Ala Leu Ser Ile Leu Leu Val Lys
            20                  25

<210> SEQ ID NO 32
<211> LENGTH: 25
<212> TYPE: PRT
<213> ORGANISM: Artificial Sequence
<220> FEATURE:

<223> OTHER INFORMATION: neoantigen

<400> SEQUENCE: 32

Thr Gly Leu Phe Gly Gln Thr Asn Thr Gly Phe Gly Asp Val Gly Ser
1 5 10 15

Thr Leu Phe Gly Asn Asn Lys Leu Thr
20 25

<210> SEQ ID NO 33
<211> LENGTH: 25
<212> TYPE: PRT
<213> ORGANISM: Artificial Sequence
<220> FEATURE:
<223> OTHER INFORMATION: neoantigen

<400> SEQUENCE: 33

Leu Gln Glu Asn Gly Leu Ala Gly Leu Ser Ala Ser Thr Ile Val Glu
1 5 10 15

Gln Gln Leu Pro Leu Arg Arg Asn Ser
20 25

<210> SEQ ID NO 34
<211> LENGTH: 30
<212> TYPE: PRT
<213> ORGANISM: Artificial Sequence
<220> FEATURE:
<223> OTHER INFORMATION: neoantigen

<400> SEQUENCE: 34

Gly Ser Leu Ser Gly Tyr Leu Ser Gln Asp Thr Val Gly Ala Leu Pro
1 5 10 15

Val Ser Val Val Ser Leu Cys Pro Gly Arg Cys Gln Ser Gly
20 25 30

<210> SEQ ID NO 35
<211> LENGTH: 25
<212> TYPE: PRT
<213> ORGANISM: Artificial Sequence
<220> FEATURE:
<223> OTHER INFORMATION: neoantigen

<400> SEQUENCE: 35

Ser Tyr Ala Glu Gln Gly Thr Asn Cys Asp Glu Ala Val Ser Phe Met
1 5 10 15

Asp Thr His Asn Leu Asn Gly Arg Ser
20 25

<210> SEQ ID NO 36
<211> LENGTH: 25
<212> TYPE: PRT
<213> ORGANISM: Artificial Sequence
<220> FEATURE:
<223> OTHER INFORMATION: neoantigen

<400> SEQUENCE: 36

Asn Ala Met Asp Gln Leu Glu Gln Arg Val Ser Glu Leu Phe Met Asn
1 5 10 15

Ala Lys Lys Asn Lys Pro Glu Trp Arg
20 25

<210> SEQ ID NO 37
<211> LENGTH: 25
<212> TYPE: PRT
<213> ORGANISM: Artificial Sequence
<220> FEATURE:
<223> OTHER INFORMATION: neoantigen

<400> SEQUENCE: 37

Gly Asp Ala Glu Ala Glu Ala Leu Ala Arg Ser Ala Ser Ala Leu Val
1 5 10 15

Arg Ala Gln Gln Gly Arg Gly Thr Gly
20 25

<210> SEQ ID NO 38
<211> LENGTH: 18
<212> TYPE: PRT
<213> ORGANISM: Artificial Sequence
<220> FEATURE:
<223> OTHER INFORMATION: neoantigen

<400> SEQUENCE: 38

Met Arg Asn Leu Lys Phe Phe Arg Thr Leu Glu Phe Arg Asp Ile Gln
1 5 10 15

Gly Pro

<210> SEQ ID NO 39
<211> LENGTH: 31
<212> TYPE: PRT
<213> ORGANISM: Artificial Sequence
<220> FEATURE:
<223> OTHER INFORMATION: neoantigen

<400> SEQUENCE: 39

Ala Arg Pro Pro Gly Ser Val Glu Asp Ala Gly Gln Ala Val Gly His
1 5 10 15

Ile Leu Ala Gln Ala Cys Val Tyr Arg Ala Val Gln Cys Ser Arg
20 25 30

<210> SEQ ID NO 40
<211> LENGTH: 18
<212> TYPE: PRT
<213> ORGANISM: Artificial Sequence
<220> FEATURE:
<223> OTHER INFORMATION: neoantigen

<400> SEQUENCE: 40

Pro Glu His Leu Leu Leu Leu Pro Glu Gln Gly Pro Arg Cys Ala Ala
1 5 10 15

Trp Gly

<210> SEQ ID NO 41
<211> LENGTH: 25
<212> TYPE: PRT
<213> ORGANISM: Artificial Sequence
<220> FEATURE:
<223> OTHER INFORMATION: neoantigen

<400> SEQUENCE: 41

Val His Trp Thr Val Asp Gln Gln Ser Gln Tyr Ile Lys Gly Tyr Lys
1 5 10 15

Ile Leu Tyr Arg Pro Ser Gly Ala Asn
20 25

<210> SEQ ID NO 42
<211> LENGTH: 25
<212> TYPE: PRT
<213> ORGANISM: Artificial Sequence
<220> FEATURE:

<223> OTHER INFORMATION: neoantigen

<400> SEQUENCE: 42

Glu Thr Thr Ser His Ser Thr Pro Gly Phe Thr Ser Leu Ile Thr Thr
1 5 10 15

Thr Glu Thr Thr Ser His Ser Thr Pro
20 25

<210> SEQ ID NO 43
<211> LENGTH: 25
<212> TYPE: PRT
<213> ORGANISM: Artificial Sequence
<220> FEATURE:
<223> OTHER INFORMATION: neoantigen

<400> SEQUENCE: 43

Pro Val Phe Thr His Glu Asn Ile Gln Gly Gly Gly Val Pro Phe Gln
1 5 10 15

Ala Leu Tyr Asn Tyr Thr Pro Arg Asn
20 25

<210> SEQ ID NO 44
<211> LENGTH: 25
<212> TYPE: PRT
<213> ORGANISM: Artificial Sequence
<220> FEATURE:
<223> OTHER INFORMATION: neoantigen

<400> SEQUENCE: 44

Thr Thr Leu Ser Ser Ile Lys Val Glu Val Ala Ser Arg Gln Ala Glu
1 5 10 15

Thr Thr Thr Leu Asp Gln Asp His Leu
20 25

<210> SEQ ID NO 45
<211> LENGTH: 24
<212> TYPE: PRT
<213> ORGANISM: Artificial Sequence
<220> FEATURE:
<223> OTHER INFORMATION: neoantigen

<400> SEQUENCE: 45

Cys Cys Tyr Gly Lys Gln Leu Cys Thr Ile Pro Arg Arg Ile Gly Ile
1 5 10 15

Ile Ser Val Arg Ser Val Ser Gln
20

<210> SEQ ID NO 46
<211> LENGTH: 25
<212> TYPE: PRT
<213> ORGANISM: Artificial Sequence
<220> FEATURE:
<223> OTHER INFORMATION: neoantigen

<400> SEQUENCE: 46

Asp Val Leu Ala Asp Asp Arg Asp Asp Tyr Asp Phe Met Met Gln Thr
1 5 10 15

Ser Thr Tyr Tyr Tyr Ser Val Arg Ile
20 25

<210> SEQ ID NO 47
<211> LENGTH: 25
<212> TYPE: PRT
<213> ORGANISM: Artificial Sequence
<220> FEATURE:
<223> OTHER INFORMATION: neoantigen

<400> SEQUENCE: 47

Ala Leu Thr Gly Ala Trp Ala Met Glu Asp Phe Tyr Met Ala Arg Leu
1 5 10 15

Val Pro Pro Leu Val Pro Gln Arg Pro
20 25

<210> SEQ ID NO 48
<211> LENGTH: 25
<212> TYPE: PRT
<213> ORGANISM: Artificial Sequence
<220> FEATURE:
<223> OTHER INFORMATION: neoantigen

<400> SEQUENCE: 48

Cys Pro Asn Gln Lys Val Leu Lys Tyr Tyr Tyr Val Trp Gln Tyr Cys
1 5 10 15

Pro Ala Gly Asn Trp Ala Asn Arg Leu
20 25

<210> SEQ ID NO 49
<211> LENGTH: 25
<212> TYPE: PRT
<213> ORGANISM: Artificial Sequence
<220> FEATURE:
<223> OTHER INFORMATION: neoantigen

<400> SEQUENCE: 49

Gln Asp Gly Ile Pro Gly Asp Glu Gly Leu Glu Leu Leu Ser Ala Asp
1 5 10 15

Ser Ala Val Pro Val Ala Met Thr Gln
20 25

<210> SEQ ID NO 50
<211> LENGTH: 25
<212> TYPE: PRT
<213> ORGANISM: Artificial Sequence
<220> FEATURE:
<223> OTHER INFORMATION: neoantigen

<400> SEQUENCE: 50

Thr Asn Ser Thr Ala Ala Ser Arg Pro Pro Val Thr Gln Arg Leu Val
1 5 10 15

Val Pro Ala Thr Gln Cys Gly Ser Leu
20 25

<210> SEQ ID NO 51
<211> LENGTH: 25
<212> TYPE: PRT
<213> ORGANISM: Artificial Sequence
<220> FEATURE:
<223> OTHER INFORMATION: neoantigen

<400> SEQUENCE: 51

Gln Glu Ile Glu Glu Lys Leu Ile Glu Glu Glu Thr Leu Arg Arg Val
1 5 10 15

Glu Glu Leu Val Ala Lys Arg Val Glu
20 25

<210> SEQ ID NO 52
<211> LENGTH: 25
<212> TYPE: PRT

<213> ORGANISM: Artificial Sequence
<220> FEATURE:
<223> OTHER INFORMATION: neoantigen

<400> SEQUENCE: 52

Thr Asp Phe Ile Arg Glu Glu Tyr His Lys Arg Asp Ile Thr Glu Val
1               5                   10                  15

Leu Ser Pro Asn Met Tyr Asn Ser Lys
            20                  25

<210> SEQ ID NO 53
<211> LENGTH: 17
<212> TYPE: PRT
<213> ORGANISM: Artificial Sequence
<220> FEATURE:
<223> OTHER INFORMATION: neoantigen

<400> SEQUENCE: 53

Met Ser Glu Ala Cys Arg Asp Ser Thr Ser Ser Leu Gln Arg Lys Lys
1               5                   10                  15

Pro

<210> SEQ ID NO 54
<211> LENGTH: 25
<212> TYPE: PRT
<213> ORGANISM: Artificial Sequence
<220> FEATURE:
<223> OTHER INFORMATION: neoantigen

<400> SEQUENCE: 54

His Asp Lys Glu Val Tyr Asp Ile Ala Phe Ser Arg Thr Gly Gly Gly
1               5                   10                  15

Arg Asp Met Phe Ala Ser Val Gly Ala
            20                  25

<210> SEQ ID NO 55
<211> LENGTH: 25
<212> TYPE: PRT
<213> ORGANISM: Artificial Sequence
<220> FEATURE:
<223> OTHER INFORMATION: neoantigen

<400> SEQUENCE: 55

Glu Ile Pro Thr Ala Ala Leu Val Leu Gly Val Asn Ile Thr Asp His
1               5                   10                  15

Asp Leu Thr Phe Gly Ser Leu Thr Glu
            20                  25

<210> SEQ ID NO 56
<211> LENGTH: 25
<212> TYPE: PRT
<213> ORGANISM: Artificial Sequence
<220> FEATURE:
<223> OTHER INFORMATION: neoantigen

<400> SEQUENCE: 56

Ser Ser Leu Ile Ile His Gln Arg Thr His Thr Gly Lys Lys Pro Tyr
1               5                   10                  15

Gln Cys Gly Glu Cys Gly Lys Ser Phe
            20                  25

<210> SEQ ID NO 57
<211> LENGTH: 25
<212> TYPE: PRT

<213> ORGANISM: Artificial Sequence
<220> FEATURE:
<223> OTHER INFORMATION: neoantigen

<400> SEQUENCE: 57

```
Ser Gly Asn Leu Leu Gly Arg Asn Ser Phe Glu Val Cys Val Cys Ala
1               5                   10                  15

Cys Pro Gly Arg Asp Arg Arg Thr Glu
            20                  25
```

<210> SEQ ID NO 58
<211> LENGTH: 25
<212> TYPE: PRT
<213> ORGANISM: Artificial Sequence
<220> FEATURE:
<223> OTHER INFORMATION: neoantigen

<400> SEQUENCE: 58

```
Ser Cys Leu Leu Ile Leu Glu Phe Val Met Ile Val Ile Phe Gly Leu
1               5                   10                  15

Glu Phe Ile Ile Arg Ile Trp Ser Ala
            20                  25
```

<210> SEQ ID NO 59
<211> LENGTH: 25
<212> TYPE: PRT
<213> ORGANISM: Artificial Sequence
<220> FEATURE:
<223> OTHER INFORMATION: neoantigen

<400> SEQUENCE: 59

```
Leu Thr Glu Gly Gln Lys Arg Tyr Phe Glu Lys Leu Leu Ile Tyr Cys
1               5                   10                  15

Asp Gln Tyr Ala Ser Leu Ile Pro Val
            20                  25
```

<210> SEQ ID NO 60
<211> LENGTH: 25
<212> TYPE: PRT
<213> ORGANISM: Artificial Sequence
<220> FEATURE:
<223> OTHER INFORMATION: neoantigen

<400> SEQUENCE: 60

```
Gln Ala Pro Thr Pro Ala Pro Ser Thr Ile Pro Gly Leu Arg Arg Gly
1               5                   10                  15

Ser Gly Pro Glu Ile Phe Thr Phe Asp
            20                  25
```

<210> SEQ ID NO 61
<211> LENGTH: 25
<212> TYPE: PRT
<213> ORGANISM: Artificial Sequence
<220> FEATURE:
<223> OTHER INFORMATION: neoantigen

<400> SEQUENCE: 61

```
Val Ala Ile Ile Pro Tyr Phe Ile Thr Leu Gly Thr Gln Leu Ala Glu
1               5                   10                  15

Lys Pro Glu Asp Ala Gln Gln Gly Gln
            20                  25
```

<210> SEQ ID NO 62
<211> LENGTH: 25

<212> TYPE: PRT
<213> ORGANISM: Artificial Sequence
<220> FEATURE:
<223> OTHER INFORMATION: neoantigen

<400> SEQUENCE: 62

Pro Gly His Gly Leu Pro Pro His Leu Arg Gln Gln Arg Ala Ala Arg
1 5 10 15

Leu Arg Gln Pro Asp Ala Ala Glu Ala
20 25

<210> SEQ ID NO 63
<211> LENGTH: 25
<212> TYPE: PRT
<213> ORGANISM: Artificial Sequence
<220> FEATURE:
<223> OTHER INFORMATION: neoantigen

<400> SEQUENCE: 63

Ile Ile Glu Lys His Phe Gly Glu Glu Glu Asp Glu Arg Gln Thr Leu
1 5 10 15

Leu Ser Gln Val Ile Asp Gln Asp Tyr
20 25

<210> SEQ ID NO 64
<211> LENGTH: 25
<212> TYPE: PRT
<213> ORGANISM: Artificial Sequence
<220> FEATURE:
<223> OTHER INFORMATION: neoantigen

<400> SEQUENCE: 64

Tyr Glu Ile Gly Arg Gln Phe Arg Asn Glu Gly Ile His Leu Thr His
1 5 10 15

Asn Pro Glu Phe Thr Thr Cys Glu Phe
20 25

<210> SEQ ID NO 65
<211> LENGTH: 25
<212> TYPE: PRT
<213> ORGANISM: Artificial Sequence
<220> FEATURE:
<223> OTHER INFORMATION: neoantigen

<400> SEQUENCE: 65

Arg Leu Met Trp Lys Ser Gln Tyr Val Pro Tyr Asp Glu Ile Pro Phe
1 5 10 15

Val Asn Ala Gly Ser Arg Ala Val Val
20 25

<210> SEQ ID NO 66
<211> LENGTH: 25
<212> TYPE: PRT
<213> ORGANISM: Artificial Sequence
<220> FEATURE:
<223> OTHER INFORMATION: neoantigen

<400> SEQUENCE: 66

Gln Ala Gln Ser Lys Phe Lys Ser Glu Lys Gln Asn Gln Lys Gln Leu
1 5 10 15

Glu Leu Lys Val Thr Ser Leu Glu Glu
20 25

<210> SEQ ID NO 67

<211> LENGTH: 25
<212> TYPE: PRT
<213> ORGANISM: Artificial Sequence
<220> FEATURE:
<223> OTHER INFORMATION: neoantigen

<400> SEQUENCE: 67

Ser Phe Cys Asp Gly Leu Val His Asp Pro Leu Arg Gln Lys Ala Asn
1               5                   10                  15

Phe Leu Lys Leu Leu Ile Ser Glu Leu
            20                  25

<210> SEQ ID NO 68
<211> LENGTH: 25
<212> TYPE: PRT
<213> ORGANISM: Artificial Sequence
<220> FEATURE:
<223> OTHER INFORMATION: neoantigen

<400> SEQUENCE: 68

Leu Asp Gly Gly Asp Phe Val Ser Leu Ser Ser Arg Lys Glu Val Gln
1               5                   10                  15

Glu Asn Cys Val Arg Trp Arg Lys Arg
            20                  25

<210> SEQ ID NO 69
<211> LENGTH: 25
<212> TYPE: PRT
<213> ORGANISM: Artificial Sequence
<220> FEATURE:
<223> OTHER INFORMATION: neoantigen

<400> SEQUENCE: 69

Gln Ser Leu Pro Leu Glu Thr Phe Ser Phe Leu Leu Ile Leu Leu Ala
1               5                   10                  15

Thr Thr Val Thr Pro Val Phe Val Leu
            20                  25

<210> SEQ ID NO 70
<211> LENGTH: 25
<212> TYPE: PRT
<213> ORGANISM: Artificial Sequence
<220> FEATURE:
<223> OTHER INFORMATION: neoantigen

<400> SEQUENCE: 70

Gly Lys Phe Asp Glu Leu Ala Thr Glu Asn His Cys His Arg Ile Lys
1               5                   10                  15

Ile Leu Gly Asp Cys Tyr Tyr Cys Val
            20                  25

<210> SEQ ID NO 71
<211> LENGTH: 25
<212> TYPE: PRT
<213> ORGANISM: Artificial Sequence
<220> FEATURE:
<223> OTHER INFORMATION: neoantigen

<400> SEQUENCE: 71

Val Gly Ser Ser Leu Pro Glu Ala Ser Pro Pro Ala Leu Glu Pro Ser
1               5                   10                  15

Ser Pro Asn Ala Ala Val Pro Glu Ala
            20                  25

<210> SEQ ID NO 72
<211> LENGTH: 30
<212> TYPE: PRT
<213> ORGANISM: Artificial Sequence
<220> FEATURE:
<223> OTHER INFORMATION: Assembled FSP

<400> SEQUENCE: 72

```
Gly Ser Leu Ser Gly Tyr Leu Ser Gln Asp Thr Val Gly Ala Leu Pro
1               5                   10                  15

Val Ser Val Val Ser Leu Cys Pro Gly Arg Cys Gln Ser Gly
            20                  25                  30
```

<210> SEQ ID NO 73
<211> LENGTH: 23
<212> TYPE: PRT
<213> ORGANISM: Artificial Sequence
<220> FEATURE:
<223> OTHER INFORMATION: FSP fragment

<400> SEQUENCE: 73

```
Gly Ser Leu Ser Gly Tyr Leu Ser Gln Asp Thr Val Gly Ala Leu Pro
1               5                   10                  15

Val Ser Val Val Ser Leu Cys
            20
```

<210> SEQ ID NO 74
<211> LENGTH: 25
<212> TYPE: PRT
<213> ORGANISM: Artificial Sequence
<220> FEATURE:
<223> OTHER INFORMATION: FSP fragment

<400> SEQUENCE: 74

```
Tyr Leu Ser Gln Asp Thr Val Gly Ala Leu Pro Val Ser Val Val Ser
1               5                   10                  15

Leu Cys Pro Gly Arg Cys Gln Ser Gly
            20                  25
```

<210> SEQ ID NO 75
<211> LENGTH: 25
<212> TYPE: PRT
<213> ORGANISM: Artificial Sequence
<220> FEATURE:
<223> OTHER INFORMATION: FSP fragment

<400> SEQUENCE: 75

```
Leu Ser Gly Tyr Leu Ser Gln Asp Thr Val Gly Ala Leu Pro Val Ser
1               5                   10                  15

Val Val Ser Leu Cys Pro Gly Arg Cys
            20                  25
```

<210> SEQ ID NO 76
<211> LENGTH: 25
<212> TYPE: PRT
<213> ORGANISM: Artificial Sequence
<220> FEATURE:
<223> OTHER INFORMATION: FSP fragment

<400> SEQUENCE: 76

```
Ser Gly Tyr Leu Ser Gln Asp Thr Val Gly Ala Leu Pro Val Ser Val
1               5                   10                  15

Val Ser Leu Cys Pro Gly Arg Cys Gln
            20                  25
```

<210> SEQ ID NO 77
<211> LENGTH: 31
<212> TYPE: PRT
<213> ORGANISM: Artificial Sequence
<220> FEATURE:
<223> OTHER INFORMATION: Assembled FSP

<400> SEQUENCE: 77

Ala Arg Pro Pro Gly Ser Val Glu Asp Ala Gly Gln Ala Val Gly His
1               5                   10                  15

Ile Leu Ala Gln Ala Cys Val Tyr Arg Ala Val Gln Cys Ser Arg
            20                  25                  30

<210> SEQ ID NO 78
<211> LENGTH: 22
<212> TYPE: PRT
<213> ORGANISM: Artificial Sequence
<220> FEATURE:
<223> OTHER INFORMATION: FSP fragment

<400> SEQUENCE: 78

Ala Arg Pro Pro Gly Ser Val Glu Asp Ala Gly Gln Ala Val Gly His
1               5                   10                  15

Ile Leu Ala Gln Ala Cys
            20

<210> SEQ ID NO 79
<211> LENGTH: 24
<212> TYPE: PRT
<213> ORGANISM: Artificial Sequence
<220> FEATURE:
<223> OTHER INFORMATION: FSP fragment

<400> SEQUENCE: 79

Glu Asp Ala Gly Gln Ala Val Gly His Ile Leu Ala Gln Ala Cys Val
1               5                   10                  15

Tyr Arg Ala Val Gln Cys Ser Arg
            20

<210> SEQ ID NO 80
<211> LENGTH: 25
<212> TYPE: PRT
<213> ORGANISM: Artificial Sequence
<220> FEATURE:
<223> OTHER INFORMATION: neoantigen

<400> SEQUENCE: 80

Asp Ser Leu Gln Leu Val Phe Gly Ile Glu Leu Met Lys Val Asp Pro
1               5                   10                  15

Ile Gly His Val Tyr Ile Phe Ala Thr
            20                  25

<210> SEQ ID NO 81
<211> LENGTH: 25
<212> TYPE: PRT
<213> ORGANISM: Artificial Sequence
<220> FEATURE:
<223> OTHER INFORMATION: neoantigen

<400> SEQUENCE: 81

Ser Leu Leu Pro Glu Phe Val Val Pro Tyr Met Ile Tyr Leu Leu Ala
1               5                   10                  15

His Asp Pro Asp Phe Thr Arg Ser Gln
            20                  25

<210> SEQ ID NO 82
<211> LENGTH: 25
<212> TYPE: PRT
<213> ORGANISM: Artificial Sequence
<220> FEATURE:
<223> OTHER INFORMATION: neoantigen

<400> SEQUENCE: 82

```
Pro His Ile Lys Ser Thr Val Ser Val Gln Ile Ile Ser Cys Gln Tyr
1               5                   10                  15

Leu Leu Gln Pro Val Lys His Glu Asp
            20                  25
```

<210> SEQ ID NO 83
<211> LENGTH: 25
<212> TYPE: PRT
<213> ORGANISM: Artificial Sequence
<220> FEATURE:
<223> OTHER INFORMATION: neoantigen

<400> SEQUENCE: 83

```
Val Val Ile Ser Gln Ser Glu Ile Gly Asp Ala Ser Cys Val Arg Val
1               5                   10                  15

Ser Gly Gln Gly Leu His Glu Gly His
            20                  25
```

<210> SEQ ID NO 84
<211> LENGTH: 25
<212> TYPE: PRT
<213> ORGANISM: Artificial Sequence
<220> FEATURE:
<223> OTHER INFORMATION: neoantigen

<400> SEQUENCE: 84

```
Arg Lys Thr Val Arg Ala Arg Ser Arg Thr Pro Ser Cys Arg Ser Arg
1               5                   10                  15

Ser His Thr Pro Ser Arg Arg Arg Arg
            20                  25
```

<210> SEQ ID NO 85
<211> LENGTH: 25
<212> TYPE: PRT
<213> ORGANISM: Artificial Sequence
<220> FEATURE:
<223> OTHER INFORMATION: neoantigen

<400> SEQUENCE: 85

```
Arg Glu Lys Gln Gln Arg Glu Ala Leu Glu Arg Ala Pro Ala Arg Leu
1               5                   10                  15

Glu Arg Arg His Ser Ala Leu Gln Arg
            20                  25
```

<210> SEQ ID NO 86
<211> LENGTH: 25
<212> TYPE: PRT
<213> ORGANISM: Artificial Sequence
<220> FEATURE:
<223> OTHER INFORMATION: neoantigen

<400> SEQUENCE: 86

```
Thr Leu Lys Arg Gln Leu Glu His Asn Ala Tyr His Ser Ile Glu Trp
1               5                   10                  15

Ala Ile Asn Ala Ala Thr Leu Ser Gln
```

20 25

<210> SEQ ID NO 87
<211> LENGTH: 25
<212> TYPE: PRT
<213> ORGANISM: Artificial Sequence
<220> FEATURE:
<223> OTHER INFORMATION: neoantigen

<400> SEQUENCE: 87

Val Thr Val Arg Val Ala Asp Ile Asn Asp His Ala Leu Ala Phe Pro
1 5 10 15

Gln Ala Arg Ala Ala Leu Gln Val Pro
20 25

<210> SEQ ID NO 88
<211> LENGTH: 25
<212> TYPE: PRT
<213> ORGANISM: Artificial Sequence
<220> FEATURE:
<223> OTHER INFORMATION: neoantigen

<400> SEQUENCE: 88

Leu Arg Pro Arg Arg Val Gly Ile Ala Leu Asp Tyr Asp Trp Gly Thr
1 5 10 15

Val Thr Phe Thr Asn Ala Glu Ser Gln
20 25

<210> SEQ ID NO 89
<211> LENGTH: 25
<212> TYPE: PRT
<213> ORGANISM: Artificial Sequence
<220> FEATURE:
<223> OTHER INFORMATION: neoantigen

<400> SEQUENCE: 89

Gly Tyr Val Gly Ile Asp Ser Ile Leu Glu Gln Met His Arg Lys Ala
1 5 10 15

Met Lys Gln Gly Phe Glu Phe Asn Ile
20 25

<210> SEQ ID NO 90
<211> LENGTH: 25
<212> TYPE: PRT
<213> ORGANISM: Artificial Sequence
<220> FEATURE:
<223> OTHER INFORMATION: neoantigen

<400> SEQUENCE: 90

Ile Ile Val Gly Val Leu Leu Ala Ile Gly Phe Ile Cys Ala Ile Ile
1 5 10 15

Val Val Val Met Arg Lys Met Ser Gly
20 25

<210> SEQ ID NO 91
<211> LENGTH: 25
<212> TYPE: PRT
<213> ORGANISM: Artificial Sequence
<220> FEATURE:
<223> OTHER INFORMATION: neoantigen

<400> SEQUENCE: 91

Pro Arg Glu Gly Ser Gly Gly Ser Thr Ser Asp Tyr Leu Ser Gln Ser
1 5 10 15

Tyr Ser Tyr Ser Ser Ile Leu Asn Lys
20 25

<210> SEQ ID NO 92
<211> LENGTH: 25
<212> TYPE: PRT
<213> ORGANISM: Artificial Sequence
<220> FEATURE:
<223> OTHER INFORMATION: neoantigen

<400> SEQUENCE: 92

Arg Arg Ala Gly Gly Ala Gln Ser Trp Leu Trp Phe Val Thr Val Lys
1 5 10 15

Ser Leu Ile Gly Lys Gly Val Met Leu
20 25

<210> SEQ ID NO 93
<211> LENGTH: 25
<212> TYPE: PRT
<213> ORGANISM: Artificial Sequence
<220> FEATURE:
<223> OTHER INFORMATION: neoantigen

<400> SEQUENCE: 93

Gln Ser Ile Ser Arg Asn His Val Val Asp Ile Ser Lys Ser Gly Leu
1 5 10 15

Ile Thr Ile Ala Gly Gly Lys Trp Thr
20 25

<210> SEQ ID NO 94
<211> LENGTH: 25
<212> TYPE: PRT
<213> ORGANISM: Artificial Sequence
<220> FEATURE:
<223> OTHER INFORMATION: neoantigen

<400> SEQUENCE: 94

Thr Gly Leu Phe Gly Gln Thr Asn Thr Gly Phe Gly Asp Val Gly Ser
1 5 10 15

Thr Leu Phe Gly Asn Asn Lys Leu Thr
20 25

<210> SEQ ID NO 95
<211> LENGTH: 25
<212> TYPE: PRT
<213> ORGANISM: Artificial Sequence
<220> FEATURE:
<223> OTHER INFORMATION: neoantigen

<400> SEQUENCE: 95

Tyr Glu Ile Gly Arg Gln Phe Arg Asn Glu Gly Ile His Leu Thr His
1 5 10 15

Asn Pro Glu Phe Thr Thr Cys Glu Phe
20 25

<210> SEQ ID NO 96
<211> LENGTH: 25
<212> TYPE: PRT
<213> ORGANISM: Artificial Sequence
<220> FEATURE:
<223> OTHER INFORMATION: neoantigen

<400> SEQUENCE: 96

Pro Ile Leu Lys Glu Ile Val Glu Met Leu Phe Ser His Gly Leu Val
1 5 10 15

Lys Val Leu Phe Ala Thr Glu Thr Phe
20 25

<210> SEQ ID NO 97
<211> LENGTH: 25
<212> TYPE: PRT
<213> ORGANISM: Artificial Sequence
<220> FEATURE:
<223> OTHER INFORMATION: neoantigen

<400> SEQUENCE: 97

Val Lys Lys Pro His Arg Tyr Arg Pro Gly Thr Val Thr Leu Arg Glu
1 5 10 15

Ile Arg Arg Tyr Gln Lys Ser Thr Glu
20 25

<210> SEQ ID NO 98
<211> LENGTH: 25
<212> TYPE: PRT
<213> ORGANISM: Artificial Sequence
<220> FEATURE:
<223> OTHER INFORMATION: neoantigen

<400> SEQUENCE: 98

Phe Val Thr Gln Lys Arg Met Glu His Phe Tyr Leu Ser Phe Tyr Thr
1 5 10 15

Ala Glu Gln Leu Val Tyr Leu Ser Thr
20 25

<210> SEQ ID NO 99
<211> LENGTH: 25
<212> TYPE: PRT
<213> ORGANISM: Artificial Sequence
<220> FEATURE:
<223> OTHER INFORMATION: neoantigen

<400> SEQUENCE: 99

Asp Leu Ser Ile Arg Glu Leu Val His Arg Ile Leu Leu Val Ala Ala
1 5 10 15

Ser Tyr Ser Ala Val Thr Arg Phe Ile
20 25

<210> SEQ ID NO 100
<211> LENGTH: 24
<212> TYPE: PRT
<213> ORGANISM: Artificial Sequence
<220> FEATURE:
<223> OTHER INFORMATION: neoantigen

<400> SEQUENCE: 100

Met Thr Glu Tyr Lys Leu Val Val Val Gly Ala Asp Gly Val Gly Lys
1 5 10 15

Ser Ala Leu Thr Ile Gln Leu Ile
20

<210> SEQ ID NO 101
<211> LENGTH: 25
<212> TYPE: PRT
<213> ORGANISM: Artificial Sequence
<220> FEATURE:
<223> OTHER INFORMATION: neoantigen

<400> SEQUENCE: 101

Asp Pro Asp Cys Val Asp Arg Leu Leu Gln Cys Thr Gln Gln Ala Val

```
1               5                   10                  15

Pro Leu Phe Ser Lys Asn Val His Ser
            20                  25


<210> SEQ ID NO 102
<211> LENGTH: 25
<212> TYPE: PRT
<213> ORGANISM: Artificial Sequence
<220> FEATURE:
<223> OTHER INFORMATION: neoantigen

<400> SEQUENCE: 102

Val Asn Arg Trp Thr Arg Arg Gln Val Ile Leu Cys Glu Thr Cys Leu
1               5                   10                  15

Ile Val Ser Ser Val Lys Asp Ser Leu
            20                  25


<210> SEQ ID NO 103
<211> LENGTH: 25
<212> TYPE: PRT
<213> ORGANISM: Artificial Sequence
<220> FEATURE:
<223> OTHER INFORMATION: neoantigen

<400> SEQUENCE: 103

Arg His Arg Tyr Leu Ser His Leu Pro Leu Thr Cys Lys Phe Ser Ile
1               5                   10                  15

Cys Glu Leu Ala Leu Gln Pro Pro Val
            20                  25


<210> SEQ ID NO 104
<211> LENGTH: 25
<212> TYPE: PRT
<213> ORGANISM: Artificial Sequence
<220> FEATURE:
<223> OTHER INFORMATION: neoantigen

<400> SEQUENCE: 104

Leu Leu Ala Ser Ser Asp Pro Pro Ala Leu Ala Ser Thr Asn Ala Glu
1               5                   10                  15

Val Thr Gly Thr Met Ser Gln Asp Thr
            20                  25


<210> SEQ ID NO 105
<211> LENGTH: 25
<212> TYPE: PRT
<213> ORGANISM: Artificial Sequence
<220> FEATURE:
<223> OTHER INFORMATION: neoantigen

<400> SEQUENCE: 105

Thr Leu Asn Ser Lys Thr Tyr Asp Thr Val His Arg His Leu Thr Val
1               5                   10                  15

Glu Glu Ala Thr Ala Ser Val Ser Glu
            20                  25


<210> SEQ ID NO 106
<211> LENGTH: 25
<212> TYPE: PRT
<213> ORGANISM: Artificial Sequence
<220> FEATURE:
<223> OTHER INFORMATION: neoantigen

<400> SEQUENCE: 106
```

```
Gly Tyr Asn Ser Tyr Ser Val Ser Asn Ser Glu Lys His Ile Met Ala
1               5                   10                  15

Glu Ile Tyr Lys Asn Gly Pro Val Glu
            20                  25


<210> SEQ ID NO 107
<211> LENGTH: 25
<212> TYPE: PRT
<213> ORGANISM: Artificial Sequence
<220> FEATURE:
<223> OTHER INFORMATION: neoantigen

<400> SEQUENCE: 107

Met Pro Tyr Gly Tyr Val Leu Asn Glu Phe Gln Ser Cys Gln Asn Ser
1               5                   10                  15

Ser Ser Ala Gln Gly Ser Ser Ser Asn
            20                  25


<210> SEQ ID NO 108
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 108

Pro Gly Pro Gln Asn Phe Pro Pro Gln Asn Met Phe Glu Phe Pro Pro
1               5                   10                  15

His Leu Ser Pro Pro Leu Leu Pro Pro
            20                  25


<210> SEQ ID NO 109
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 109

Gly Ala Gln Glu Glu Pro Gln Val Glu Pro Leu Asp Phe Ser Leu Pro
1               5                   10                  15

Lys Gln Gln Gly Glu Leu Leu Glu Arg
            20                  25


<210> SEQ ID NO 110
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 110

Ala Val Phe Ala Gly Ser Asp Asp Pro Phe Ala Thr Pro Leu Ser Met
1               5                   10                  15

Ser Glu Met Asp Arg Arg Asn Asp Ala
            20                  25


<210> SEQ ID NO 111
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 111
```

```
His Ser Gly Gln Asn His Leu Lys Glu Met Ala Ile Ser Val Leu Glu
1               5                   10                  15

Ala Arg Ala Cys Ala Ala Ala Gly Gln
            20                  25


<210> SEQ ID NO 112
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 112

Ile Leu Pro Gln Ala Pro Ser Gly Pro Ser Tyr Ala Thr Tyr Leu Gln
1               5                   10                  15

Pro Ala Gln Ala Gln Met Leu Thr Pro
            20                  25


<210> SEQ ID NO 113
<211> LENGTH: 19
<212> TYPE: PRT
<213> ORGANISM: Artificial Sequence
<220> FEATURE:
<223> OTHER INFORMATION: CT26 neoantigen

<400> SEQUENCE: 113

Met Ser Tyr Ala Glu Lys Ser Asp Glu Ile Thr Lys Asp Glu Trp Met
1               5                   10                  15

Glu Lys Leu


<210> SEQ ID NO 114
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 114

Gly Ala Gly Lys Gly Lys Tyr Tyr Ala Val Asn Phe Ser Met Arg Asp
1               5                   10                  15

Gly Ile Asp Asp Glu Ser Tyr Gly Gln
            20                  25


<210> SEQ ID NO 115
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 115

Tyr Arg Gly Ala Asp Lys Leu Cys Arg Lys Ala Ser Ser Val Lys Leu
1               5                   10                  15

Val Lys Thr Ser Pro Glu Leu Ser Glu
            20                  25


<210> SEQ ID NO 116
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 116
```

Asp Ser Asn Leu Gln Ala Arg Leu Thr Ser Tyr Glu Thr Leu Lys Lys
1 5 10 15

Ser Leu Ser Lys Ile Arg Glu Glu Ser
20 25

<210> SEQ ID NO 117
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 117

His Ser Phe Ile His Ala Ala Met Gly Met Ala Val Thr Trp Cys Ala
1 5 10 15

Ala Ile Met Thr Lys Gly Gln Tyr Ser
20 25

<210> SEQ ID NO 118
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 118

Leu Arg Thr Ala Ala Tyr Val Asn Ala Ile Glu Lys Ile Phe Lys Val
1 5 10 15

Tyr Asn Glu Ala Gly Val Thr Phe Thr
20 25

<210> SEQ ID NO 119
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 119

Phe Glu Gly Ser Leu Ala Lys Asn Leu Ser Leu Asn Phe Gln Ala Val
1 5 10 15

Lys Glu Asn Leu Tyr Tyr Glu Val Gly
20 25

<210> SEQ ID NO 120
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 120

Asp Pro Arg Ala Ala Tyr Phe Arg Gln Ala Glu Asn Asp Met Tyr Ile
1 5 10 15

Arg Met Ala Leu Leu Ala Thr Val Leu
20 25

<210> SEQ ID NO 121
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 121

```
Leu Arg Ser Gln Met Val Met Lys Met Arg Glu Tyr Phe Cys Asn Leu
1               5                   10                  15

His Gly Phe Val Asp Ile Glu Thr Pro
            20                  25
```

<210> SEQ ID NO 122
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 122

```
Asp Leu Leu Ala Phe Glu Arg Lys Leu Asp Gln Thr Val Met Arg Lys
1               5                   10                  15

Arg Leu Asp Ile Gln Glu Ala Leu Lys
            20                  25
```

<210> SEQ ID NO 123
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 123

```
Ile Lys Arg Glu Lys Cys Trp Lys Asp Ala Thr Tyr Pro Glu Ser Phe
1               5                   10                  15

His Thr Leu Glu Ser Val Pro Ala Thr
            20                  25
```

<210> SEQ ID NO 124
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 124

```
Gly Arg Ser Ser Gln Val Tyr Phe Thr Ile Asn Val Asn Leu Asp Leu
1               5                   10                  15

Ser Glu Ala Ala Val Val Thr Phe Ser
            20                  25
```

<210> SEQ ID NO 125
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 125

```
Lys Pro Leu Arg Arg Asn Asn Ser Tyr Thr Ser Tyr Ile Met Ala Ile
1               5                   10                  15

Cys Gly Met Pro Leu Asp Ser Phe Arg
            20                  25
```

<210> SEQ ID NO 126
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 126

Thr Thr Cys Leu Ala Val Gly Gly Leu Asp Val Lys Phe Gln Glu Ala
1               5                   10                  15

Ala Leu Arg Ala Ala Pro Asp Ile Leu
            20                  25

<210> SEQ ID NO 127
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 127

Ile Tyr Glu Phe Asp Tyr His Leu Tyr Gly Gln Asn Ile Thr Met Ile
1               5                   10                  15

Met Thr Ser Val Ser Gly His Leu Leu
            20                  25

<210> SEQ ID NO 128
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 128

Pro Asp Ser Phe Ser Ile Pro Tyr Leu Thr Ala Leu Asp Asp Leu Leu
1               5                   10                  15

Gly Thr Ala Leu Leu Ala Leu Ser Phe
            20                  25

<210> SEQ ID NO 129
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 129

Tyr Ala Thr Ile Leu Glu Met Gln Ala Met Met Thr Leu Asp Pro Gln
1               5                   10                  15

Asp Ile Leu Leu Ala Gly Asn Met Met
            20                  25

<210> SEQ ID NO 130
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 130

Ser Trp Ile His Cys Trp Lys Tyr Leu Ser Val Gln Ser Gln Leu Phe
1               5                   10                  15

Arg Gly Ser Ser Leu Leu Phe Arg Arg
            20                  25

<210> SEQ ID NO 131
<211> LENGTH: 25
<212> TYPE: PRT
<213> ORGANISM: Artificial Sequence
<220> FEATURE:

<223> OTHER INFORMATION: CT26 neoantigen

<400> SEQUENCE: 131

Tyr Asp Asn Lys Gly Ile Thr Tyr Leu Phe Asp Leu Tyr Tyr Glu Ser
1               5                   10                  15

Asp Glu Phe Thr Val Asp Ala Ala Arg
            20                  25

<210> SEQ ID NO 132
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 132

Ala Gln Ala Ala Lys Asn Lys Gly Asn Lys Tyr Phe Gln Ala Gly Lys
1               5                   10                  15

Tyr Glu Gln Ala Ile Gln Cys Tyr Thr
            20                  25

<210> SEQ ID NO 133
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 133

Gln Pro Met Leu Pro Ile Gly Leu Ser Asp Ile Pro Asp Glu Ala Met
1               5                   10                  15

Val Lys Leu Tyr Cys Pro Lys Cys Met
            20                  25

<210> SEQ ID NO 134
<211> LENGTH: 23
<212> TYPE: PRT
<213> ORGANISM: Artificial Sequence
<220> FEATURE:
<223> OTHER INFORMATION: CT26 neoantigen

<400> SEQUENCE: 134

His Arg Gly Ala Ile Tyr Gly Ser Ser Trp Lys Tyr Phe Thr Phe Ser
1               5                   10                  15

Gly Tyr Leu Leu Tyr Gln Asp
            20

<210> SEQ ID NO 135
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 135

Val Ile Gln Thr Ser Lys Tyr Tyr Met Arg Asp Val Ile Ala Ile Glu
1               5                   10                  15

Ser Ala Trp Leu Leu Glu Leu Ala Pro
            20                  25

<210> SEQ ID NO 136
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 136

Pro Arg Gly Val Asp Leu Tyr Leu Arg Ile Leu Met Pro Ile Asp Ser
1 5 10 15

Glu Leu Val Asp Arg Asp Val Val His
20 25

<210> SEQ ID NO 137
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 137

Gln Ile Glu Gln Asp Ala Leu Cys Pro Gln Asp Thr Tyr Cys Asp Leu
1 5 10 15

Lys Ser Arg Ala Glu Val Asn Gly Ala
20 25

<210> SEQ ID NO 138
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 138

Ala Leu Ala Ser Ala Ile Leu Ser Asp Pro Glu Ser Tyr Ile Lys Lys
1 5 10 15

Leu Lys Glu Leu Arg Ser Met Leu Met
20 25

<210> SEQ ID NO 139
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 139

Val Ile Val Leu Asp Ser Ser Gln Gly Asn Ser Val Cys Gln Ile Ala
1 5 10 15

Met Val His Tyr Ile Lys Gln Lys Tyr
20 25

<210> SEQ ID NO 140
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 140

Met Lys Ser Val Ser Ile Gln Tyr Leu Glu Ala Val Lys Arg Leu Lys
1 5 10 15

Ser Glu Gly His Arg Phe Pro Arg Thr
20 25

<210> SEQ ID NO 141
<211> LENGTH: 25
<212> TYPE: PRT

<213> ORGANISM: Artificial Sequence
<220> FEATURE:
<223> OTHER INFORMATION: CT26 neoantigen

<400> SEQUENCE: 141

Lys Gly Gly Pro Val Lys Ile Asp Pro Leu Ala Leu Met Gln Ala Ile
1               5                   10                  15

Glu Arg Tyr Leu Val Val Arg Gly Tyr
            20                  25

<210> SEQ ID NO 142
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 142

Leu Gln Asp Asp Pro Asp Leu Gln Ala Leu Leu Lys Ala Ser Gln Leu
1               5                   10                  15

Leu Lys Val Lys Ser Ser Ser Trp Arg
            20                  25

<210> SEQ ID NO 143
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 143

Leu Ile Ala His Met Ile Leu Gly Tyr Arg Tyr Trp Thr Gly Ile Gly
1               5                   10                  15

Val Leu Gln Ser Cys Glu Ser Ala Leu
            20                  25

<210> SEQ ID NO 144
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 144

Thr Ser Val Asp Gln His Leu Ala Pro Gly Ala Val Ala Met Pro Gln
1               5                   10                  15

Ala Ala Ser Leu His Ala Val Ile Val
            20                  25

<210> SEQ ID NO 145
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 145

Glu Ile Ser Val Arg Ile Ala Thr Ile Pro Ala Phe Asp Thr Ile Met
1               5                   10                  15

Glu Thr Val Ile Gln Arg Glu Leu Leu
            20                  25

<210> SEQ ID NO 146
<211> LENGTH: 25

<212> TYPE: PRT
<213> ORGANISM: Artificial Sequence
<220> FEATURE:
<223> OTHER INFORMATION: CT26 neoantigen

<400> SEQUENCE: 146

Lys Thr Ser Arg Glu Ile Lys Ile Ser Gly Ala Ile Glu Pro Cys Val
1 5 10 15

Ser Leu Asn Ser Lys Gly Pro Cys Val
20 25

<210> SEQ ID NO 147
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 147

Gln Gly Leu Ala Asn Tyr Val Ile Thr Thr Met Gly Thr Ile Cys Ala
1 5 10 15

Pro Val Arg Asp Glu Asp Ile Arg Glu
20 25

<210> SEQ ID NO 148
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 148

Glu Leu Ser Arg Arg Gln Tyr Ala Glu Gln Glu Leu Lys Gln Val Arg
1 5 10 15

Met Ala Leu Lys Lys Ala Glu Lys Glu
20 25

<210> SEQ ID NO 149
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 149

Ile Glu Thr Gln Gln Arg Lys Phe Lys Ala Ser Arg Ala Ser Ile Leu
1 5 10 15

Ser Glu Met Lys Met Leu Lys Glu Lys
20 25

<210> SEQ ID NO 150
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 150

Ser Ile Phe Leu Asp Asp Asp Ser Asn Gln Pro Met Ala Val Ser Arg
1 5 10 15

Phe Phe Gly Asn Val Glu Leu Met Gln
20 25

<210> SEQ ID NO 151

<211> LENGTH: 25
<212> TYPE: PRT
<213> ORGANISM: Artificial Sequence
<220> FEATURE:
<223> OTHER INFORMATION: CT26 neoantigen

<400> SEQUENCE: 151

Arg Pro Asp Ser Tyr Val Arg Asp Met Glu Ile Glu Ala Ala Ser His
1 5 10 15

His Val Tyr Ala Asp Gln Pro His Ile
20 25

<210> SEQ ID NO 152
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 152

Thr Leu Ser Ala Met Ser Asn Pro Arg Ala Met Gln Val Leu Leu Gln
1 5 10 15

Ile Gln Gln Gly Leu Gln Thr Leu Ala
20 25

<210> SEQ ID NO 153
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 153

Val Met Lys Gly Thr Leu Glu Tyr Leu Met Ser Asn Thr Pro Thr Ala
1 5 10 15

Gln Ser Leu Arg Glu Ser Tyr Ile Phe
20 25

<210> SEQ ID NO 154
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 154

Ala Ala Glu Leu Phe His Gln Leu Ser Gln Ala Leu Lys Val Leu Thr
1 5 10 15

Asp Ala Ala Ala Arg Ala Ala Tyr Asp
20 25

<210> SEQ ID NO 155
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 155

Thr Gly Leu Tyr Phe Arg Lys Ser Tyr Tyr Met Gln Lys Tyr Phe Leu
1 5 10 15

Asp Thr Val Thr Glu Asp Ala Lys Val
20 25

<210> SEQ ID NO 156
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 156

```
Cys Arg Asn Asn Val His Tyr Leu Asn Asp Gly Asp Ala Ile Ile Tyr
1               5                   10                  15

His Thr Ala Ser Ile Gly Ile Leu His
            20                  25
```

<210> SEQ ID NO 157
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 157

```
Asp Ile Asn Asp Asn Asn Pro Ser Phe Pro Thr Gly Lys Met Lys Leu
1               5                   10                  15

Glu Ile Ser Glu Ala Leu Ala Pro Gly
            20                  25
```

<210> SEQ ID NO 158
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 158

```
Arg Glu Gly Ile Leu Gln Glu Glu Ser Ile Tyr Lys Pro Gln Lys Gln
1               5                   10                  15

Glu Gln Glu Leu Arg Ala Leu Gln Ala
            20                  25
```

<210> SEQ ID NO 159
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 159

```
Ile Asn Pro Thr Met Ile Ile Ser Asn Thr Leu Ser Lys Ser Ala Ile
1               5                   10                  15

Ala Thr Pro Lys Ile Ser Tyr Leu Leu
            20                  25
```

<210> SEQ ID NO 160
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 160

```
Gln Asp Leu His Asn Leu Asn Leu Leu Ser Leu Tyr Ala Asn Lys Leu
1               5                   10                  15

Gln Thr Val Ala Lys Gly Thr Phe Ser
            20                  25
```

<210> SEQ ID NO 161
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 161

Gln Glu Ile Gln Thr Tyr Ala Ile Ala Leu Ile Asn Val Leu Phe Leu
1               5                   10                  15

Lys Ala Pro Glu Asp Lys Arg Gln Asp
            20                  25

<210> SEQ ID NO 162
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 162

Cys Tyr Asn Tyr Leu Tyr Arg Met Lys Ala Leu Asp Gly Ile Arg Ala
1               5                   10                  15

Ser Glu Ile Pro Phe His Ala Glu Gly
            20                  25

<210> SEQ ID NO 163
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 163

Gln Ser Ile His Ser Phe Gln Ser Leu Glu Glu Ser Ile Ser Val Leu
1               5                   10                  15

Pro Ser Phe Gln Glu Pro His Leu Gln
            20                  25

<210> SEQ ID NO 164
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 164

Thr Asp Phe Cys Leu Arg Asn Leu Asp Gly Thr Leu Cys Tyr Leu Leu
1               5                   10                  15

Asp Lys Glu Thr Leu Arg Leu His Pro
            20                  25

<210> SEQ ID NO 165
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 165

Cys Glu Val Thr Arg Val Lys Ala Val Arg Ile Leu Pro Cys Gly Val
1               5                   10                  15

Ala Lys Val Leu Trp Met Gln Gly Ser
            20                  25

<210> SEQ ID NO 166
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 166

Gly Tyr Asp Ser Arg Ser Ala Arg Ala Phe Pro Tyr Ala Asn Val Ala
1 5 10 15

Phe Pro His Leu Thr Ser Ser Ala Pro
20 25

<210> SEQ ID NO 167
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 167

Thr Asp Lys Glu Leu Arg Glu Ala Met Ala Leu Leu Ala Ala Gln Gln
1 5 10 15

Thr Ala Leu Glu Val Ile Val Asn Met
20 25

<210> SEQ ID NO 168
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 168

Leu Ser Arg Pro Asp Leu Pro Phe Leu Ile Ala Ala Val Phe Phe Leu
1 5 10 15

Val Val Ala Val Trp Gly Glu Thr Leu
20 25

<210> SEQ ID NO 169
<211> LENGTH: 25
<212> TYPE: PRT
<213> ORGANISM: Artificial Sequence
<220> FEATURE:
<223> OTHER INFORMATION: CT26 neoantigen

<400> SEQUENCE: 169

Leu Tyr Tyr Thr Thr Val Arg Ala Leu Thr Arg His Asn Thr Met Leu
1 5 10 15

Lys Ala Met Phe Ser Gly Arg Met Glu
20 25

<210> SEQ ID NO 170
<211> LENGTH: 1582
<212> TYPE: PRT
<213> ORGANISM: Artibeus aztecus

<400> SEQUENCE: 170

Met Asp Ala Met Lys Arg Gly Leu Cys Cys Val Leu Leu Leu Cys Gly
1 5 10 15

Ala Val Phe Val Ser Pro Ser Gln Glu Ile His Ala Arg Pro Gly Pro
20 25 30

```
Gln Asn Phe Pro Pro Gln Asn Met Phe Glu Phe Pro Pro His Leu Ser
        35                  40                  45

Pro Pro Leu Leu Pro Pro Gly Ala Gln Glu Glu Pro Gln Val Glu Pro
    50                  55                  60

Leu Asp Phe Ser Leu Pro Lys Gln Gln Gly Glu Leu Leu Glu Arg Ala
65                  70                  75                  80

Val Phe Ala Gly Ser Asp Asp Pro Phe Ala Thr Pro Leu Ser Met Ser
                85                  90                  95

Glu Met Asp Arg Arg Asn Asp Ala His Ser Gly Gln Asn His Leu Lys
            100                 105                 110

Glu Met Ala Ile Ser Val Leu Glu Ala Arg Ala Cys Ala Ala Ala Gly
        115                 120                 125

Gln Ile Leu Pro Gln Ala Pro Ser Gly Pro Ser Tyr Ala Thr Tyr Leu
    130                 135                 140

Gln Pro Ala Gln Ala Gln Met Leu Thr Pro Met Ser Tyr Ala Glu Lys
145                 150                 155                 160

Ser Asp Glu Ile Thr Lys Asp Glu Trp Met Glu Lys Leu Gly Ala Gly
                165                 170                 175

Lys Gly Lys Tyr Tyr Ala Val Asn Phe Ser Met Arg Asp Gly Ile Asp
            180                 185                 190

Asp Glu Ser Tyr Gly Gln Tyr Arg Gly Ala Asp Lys Leu Cys Arg Lys
        195                 200                 205

Ala Ser Ser Val Lys Leu Val Lys Thr Ser Pro Glu Leu Ser Glu Asp
    210                 215                 220

Ser Asn Leu Gln Ala Arg Leu Thr Ser Tyr Glu Thr Leu Lys Lys Ser
225                 230                 235                 240

Leu Ser Lys Ile Arg Glu Glu Ser His Ser Phe Ile His Ala Ala Met
                245                 250                 255

Gly Met Ala Val Thr Trp Cys Ala Ala Ile Met Thr Lys Gly Gln Tyr
            260                 265                 270

Ser Leu Arg Thr Ala Ala Tyr Val Asn Ala Ile Glu Lys Ile Phe Lys
        275                 280                 285

Val Tyr Asn Glu Ala Gly Val Thr Phe Thr Phe Glu Gly Ser Leu Ala
    290                 295                 300

Lys Asn Leu Ser Leu Asn Phe Gln Ala Val Lys Glu Asn Leu Tyr Tyr
305                 310                 315                 320

Glu Val Gly Asp Pro Arg Ala Ala Tyr Phe Arg Gln Ala Glu Asn Asp
                325                 330                 335

Met Tyr Ile Arg Met Ala Leu Leu Ala Thr Val Leu Leu Arg Ser Gln
            340                 345                 350

Met Val Met Lys Met Arg Glu Tyr Phe Cys Asn Leu His Gly Phe Val
        355                 360                 365

Asp Ile Glu Thr Pro Asp Leu Leu Ala Phe Glu Arg Lys Leu Asp Gln
    370                 375                 380

Thr Val Met Arg Lys Arg Leu Asp Ile Gln Glu Ala Leu Lys Ile Lys
385                 390                 395                 400

Arg Glu Lys Cys Trp Lys Asp Ala Thr Tyr Pro Glu Ser Phe His Thr
                405                 410                 415

Leu Glu Ser Val Pro Ala Thr Gly Arg Ser Ser Gln Val Tyr Phe Thr
            420                 425                 430

Ile Asn Val Asn Leu Asp Leu Ser Glu Ala Ala Val Val Thr Phe Ser
        435                 440                 445

Lys Pro Leu Arg Arg Asn Asn Ser Tyr Thr Ser Tyr Ile Met Ala Ile
```

```
    450                 455                 460

Cys Gly Met Pro Leu Asp Ser Phe Arg Thr Thr Cys Leu Ala Val Gly
465                 470                 475                 480

Gly Leu Asp Val Lys Phe Gln Glu Ala Ala Leu Arg Ala Ala Pro Asp
                485                 490                 495

Ile Leu Ile Tyr Glu Phe Asp Tyr His Leu Tyr Gly Gln Asn Ile Thr
            500                 505                 510

Met Ile Met Thr Ser Val Ser Gly His Leu Leu Pro Asp Ser Phe Ser
        515                 520                 525

Ile Pro Tyr Leu Thr Ala Leu Asp Asp Leu Leu Gly Thr Ala Leu Leu
    530                 535                 540

Ala Leu Ser Phe Tyr Ala Thr Ile Leu Glu Met Gln Ala Met Met Thr
545                 550                 555                 560

Leu Asp Pro Gln Asp Ile Leu Leu Ala Gly Asn Met Met Ser Trp Ile
                565                 570                 575

His Cys Trp Lys Tyr Leu Ser Val Gln Ser Gln Leu Phe Arg Gly Ser
            580                 585                 590

Ser Leu Leu Phe Arg Arg Tyr Asp Asn Lys Gly Ile Thr Tyr Leu Phe
        595                 600                 605

Asp Leu Tyr Tyr Glu Ser Asp Glu Phe Thr Val Asp Ala Ala Arg Ala
    610                 615                 620

Gln Ala Ala Lys Asn Lys Gly Asn Lys Tyr Phe Gln Ala Gly Lys Tyr
625                 630                 635                 640

Glu Gln Ala Ile Gln Cys Tyr Thr Gln Pro Met Leu Pro Ile Gly Leu
                645                 650                 655

Ser Asp Ile Pro Asp Glu Ala Met Val Lys Leu Tyr Cys Pro Lys Cys
            660                 665                 670

Met His Arg Gly Ala Ile Tyr Gly Ser Ser Trp Lys Tyr Phe Thr Phe
        675                 680                 685

Ser Gly Tyr Leu Leu Tyr Gln Asp Val Ile Gln Thr Ser Lys Tyr Tyr
    690                 695                 700

Met Arg Asp Val Ile Ala Ile Glu Ser Ala Trp Leu Leu Glu Leu Ala
705                 710                 715                 720

Pro Pro Arg Gly Val Asp Leu Tyr Leu Arg Ile Leu Met Pro Ile Asp
                725                 730                 735

Ser Glu Leu Val Asp Arg Asp Val Val His Gln Ile Glu Gln Asp Ala
            740                 745                 750

Leu Cys Pro Gln Asp Thr Tyr Cys Asp Leu Lys Ser Arg Ala Glu Val
        755                 760                 765

Asn Gly Ala Ala Leu Ala Ser Ala Ile Leu Ser Asp Pro Glu Ser Tyr
    770                 775                 780

Ile Lys Lys Leu Lys Glu Leu Arg Ser Met Leu Met Val Ile Val Leu
785                 790                 795                 800

Asp Ser Ser Gln Gly Asn Ser Val Cys Gln Ile Ala Met Val His Tyr
                805                 810                 815

Ile Lys Gln Lys Tyr Met Lys Ser Val Ser Ile Gln Tyr Leu Glu Ala
            820                 825                 830

Val Lys Arg Leu Lys Ser Glu Gly His Arg Phe Pro Arg Thr Lys Gly
        835                 840                 845

Gly Pro Val Lys Ile Asp Pro Leu Ala Leu Met Gln Ala Ile Glu Arg
    850                 855                 860

Tyr Leu Val Val Arg Gly Tyr Leu Gln Asp Asp Pro Asp Leu Gln Ala
865                 870                 875                 880
```

```
Leu Leu Lys Ala Ser Gln Leu Leu Lys Val Lys Ser Ser Ser Trp Arg
                885                 890                 895

Leu Ile Ala His Met Ile Leu Gly Tyr Arg Tyr Trp Thr Gly Ile Gly
            900                 905                 910

Val Leu Gln Ser Cys Glu Ser Ala Leu Thr Ser Val Asp Gln His Leu
        915                 920                 925

Ala Pro Gly Ala Val Ala Met Pro Gln Ala Ala Ser Leu His Ala Val
    930                 935                 940

Ile Val Glu Ile Ser Val Arg Ile Ala Thr Ile Pro Ala Phe Asp Thr
945                 950                 955                 960

Ile Met Glu Thr Val Ile Gln Arg Glu Leu Leu Lys Thr Ser Arg Glu
                965                 970                 975

Ile Lys Ile Ser Gly Ala Ile Glu Pro Cys Val Ser Leu Asn Ser Lys
            980                 985                 990

Gly Pro Cys Val Gln Gly Leu Ala  Asn Tyr Val Ile Thr  Thr Met Gly
        995                 1000                1005

Thr Ile  Cys Ala Pro Val Arg  Asp Glu Asp Ile Arg  Glu Glu Leu
    1010                1015                1020

Ser Arg  Arg Gln Tyr Ala Glu  Gln Glu Leu Lys Gln  Val Arg Met
    1025                1030                1035

Ala Leu  Lys Lys Ala Glu Lys  Glu Ile Glu Thr Gln  Gln Arg Lys
    1040                1045                1050

Phe Lys  Ala Ser Arg Ala Ser  Ile Leu Ser Glu Met  Lys Met Leu
    1055                1060                1065

Lys Glu  Lys Ser Ile Phe Leu  Asp Asp Asp Ser Asn  Gln Pro Met
    1070                1075                1080

Ala Val  Ser Arg Phe Phe Gly  Asn Val Glu Leu Met  Gln Arg Pro
    1085                1090                1095

Asp Ser  Tyr Val Arg Asp Met  Glu Ile Glu Ala Ala  Ser His His
    1100                1105                1110

Val Tyr  Ala Asp Gln Pro His  Ile Thr Leu Ser Ala  Met Ser Asn
    1115                1120                1125

Pro Arg  Ala Met Gln Val Leu  Leu Gln Ile Gln Gln  Gly Leu Gln
    1130                1135                1140

Thr Leu  Ala Val Met Lys Gly  Thr Leu Glu Tyr Leu  Met Ser Asn
    1145                1150                1155

Thr Pro  Thr Ala Gln Ser Leu  Arg Glu Ser Tyr Ile  Phe Ala Ala
    1160                1165                1170

Glu Leu  Phe His Gln Leu Ser  Gln Ala Leu Lys Val  Leu Thr Asp
    1175                1180                1185

Ala Ala  Ala Arg Ala Ala Tyr  Asp Thr Gly Leu Tyr  Phe Arg Lys
    1190                1195                1200

Ser Tyr  Tyr Met Gln Lys Tyr  Phe Leu Asp Thr Val  Thr Glu Asp
    1205                1210                1215

Ala Lys  Val Cys Arg Asn Asn  Val His Tyr Leu Asn  Asp Gly Asp
    1220                1225                1230

Ala Ile  Ile Tyr His Thr Ala  Ser Ile Gly Ile Leu  His Asp Ile
    1235                1240                1245

Asn Asp  Asn Asn Pro Ser Phe  Pro Thr Gly Lys Met  Lys Leu Glu
    1250                1255                1260

Ile Ser  Glu Ala Leu Ala Pro  Gly Arg Glu Gly Ile  Leu Gln Glu
    1265                1270                1275
```

```
Glu Ser  Ile Tyr Lys Pro Gln  Lys Gln Glu Gln Glu  Leu Arg Ala
    1280                 1285                 1290

Leu Gln  Ala Ile Asn Pro Thr  Met Ile Ile Ser Asn  Thr Leu Ser
    1295                 1300                 1305

Lys Ser  Ala Ile Ala Thr Pro  Lys Ile Ser Tyr Leu  Leu Gln Asp
    1310                 1315                 1320

Leu His  Asn Leu Asn Leu Leu  Ser Leu Tyr Ala Asn  Lys Leu Gln
    1325                 1330                 1335

Thr Val  Ala Lys Gly Thr Phe  Ser Gln Glu Ile Gln  Thr Tyr Ala
    1340                 1345                 1350

Ile Ala  Leu Ile Asn Val Leu  Phe Leu Lys Ala Pro  Glu Asp Lys
    1355                 1360                 1365

Arg Gln  Asp Cys Tyr Asn Tyr  Leu Tyr Arg Met Lys  Ala Leu Asp
    1370                 1375                 1380

Gly Ile  Arg Ala Ser Glu Ile  Pro Phe His Ala Glu  Gly Gln Ser
    1385                 1390                 1395

Ile His  Ser Phe Gln Ser Leu  Glu Glu Ser Ile Ser  Val Leu Pro
    1400                 1405                 1410

Ser Phe  Gln Glu Pro His Leu  Gln Thr Asp Phe Cys  Leu Arg Asn
    1415                 1420                 1425

Leu Asp  Gly Thr Leu Cys Tyr  Leu Leu Asp Lys Glu  Thr Leu Arg
    1430                 1435                 1440

Leu His  Pro Cys Glu Val Thr  Arg Val Lys Ala Val  Arg Ile Leu
    1445                 1450                 1455

Pro Cys  Gly Val Ala Lys Val  Leu Trp Met Gln Gly  Ser Gly Tyr
    1460                 1465                 1470

Asp Ser  Arg Ser Ala Arg Ala  Phe Pro Tyr Ala Asn  Val Ala Phe
    1475                 1480                 1485

Pro His  Leu Thr Ser Ser Ala  Pro Thr Asp Lys Glu  Leu Arg Glu
    1490                 1495                 1500

Ala Met  Ala Leu Leu Ala Ala  Gln Gln Thr Ala Leu  Glu Val Ile
    1505                 1510                 1515

Val Asn  Met Leu Ser Arg Pro  Asp Leu Pro Phe Leu  Ile Ala Ala
    1520                 1525                 1530

Val Phe  Phe Leu Val Val Ala  Val Trp Gly Glu Thr  Leu Leu Tyr
    1535                 1540                 1545

Tyr Thr  Thr Val Arg Ala Leu  Thr Arg His Asn Thr  Met Leu Lys
    1550                 1555                 1560

Ala Met  Phe Ser Gly Arg Met  Glu Gly Tyr Pro Tyr  Asp Val Pro
    1565                 1570                 1575

Asp Tyr  Ala Ser
    1580
```

<210> SEQ ID NO 171
<211> LENGTH: 832
<212> TYPE: PRT
<213> ORGANISM: Artificial Sequence
<220> FEATURE:
<223> OTHER INFORMATION: GAd20-CT26-62 polyneoantigen

<400> SEQUENCE: 171

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Pro Gly Pro
            20                  25                  30
```

```
Gln Asn Phe Pro Pro Gln Asn Met Phe Glu Phe Pro Pro His Leu Ser
        35                  40                  45

Pro Pro Leu Leu Pro Pro Gly Ala Gln Glu Glu Pro Gln Val Glu Pro
    50                  55                  60

Leu Asp Phe Ser Leu Pro Lys Gln Gln Gly Glu Leu Leu Glu Arg Ala
65                  70                  75                  80

Val Phe Ala Gly Ser Asp Asp Pro Phe Ala Thr Pro Leu Ser Met Ser
                85                  90                  95

Glu Met Asp Arg Arg Asn Asp Ala His Ser Gly Gln Asn His Leu Lys
            100                 105                 110

Glu Met Ala Ile Ser Val Leu Glu Ala Arg Ala Cys Ala Ala Ala Gly
        115                 120                 125

Gln Ile Leu Pro Gln Ala Pro Ser Gly Pro Ser Tyr Ala Thr Tyr Leu
    130                 135                 140

Gln Pro Ala Gln Ala Gln Met Leu Thr Pro Met Ser Tyr Ala Glu Lys
145                 150                 155                 160

Ser Asp Glu Ile Thr Lys Asp Glu Trp Met Glu Lys Leu Gly Ala Gly
                165                 170                 175

Lys Gly Lys Tyr Tyr Ala Val Asn Phe Ser Met Arg Asp Gly Ile Asp
            180                 185                 190

Asp Glu Ser Tyr Gly Gln Tyr Arg Gly Ala Asp Lys Leu Cys Arg Lys
        195                 200                 205

Ala Ser Ser Val Lys Leu Val Lys Thr Ser Pro Glu Leu Ser Glu Asp
    210                 215                 220

Ser Asn Leu Gln Ala Arg Leu Thr Ser Tyr Glu Thr Leu Lys Lys Ser
225                 230                 235                 240

Leu Ser Lys Ile Arg Glu Glu Ser His Ser Phe Ile His Ala Ala Met
                245                 250                 255

Gly Met Ala Val Thr Trp Cys Ala Ala Ile Met Thr Lys Gly Gln Tyr
            260                 265                 270

Ser Leu Arg Thr Ala Ala Tyr Val Asn Ala Ile Glu Lys Ile Phe Lys
        275                 280                 285

Val Tyr Asn Glu Ala Gly Val Thr Phe Thr Phe Glu Gly Ser Leu Ala
    290                 295                 300

Lys Asn Leu Ser Leu Asn Phe Gln Ala Val Lys Glu Asn Leu Tyr Tyr
305                 310                 315                 320

Glu Val Gly Asp Pro Arg Ala Ala Tyr Phe Arg Gln Ala Glu Asn Asp
                325                 330                 335

Met Tyr Ile Arg Met Ala Leu Leu Ala Thr Val Leu Leu Arg Ser Gln
            340                 345                 350

Met Val Met Lys Met Arg Glu Tyr Phe Cys Asn Leu His Gly Phe Val
        355                 360                 365

Asp Ile Glu Thr Pro Asp Leu Leu Ala Phe Glu Arg Lys Leu Asp Gln
    370                 375                 380

Thr Val Met Arg Lys Arg Leu Asp Ile Gln Glu Ala Leu Lys Ile Lys
385                 390                 395                 400

Arg Glu Lys Cys Trp Lys Asp Ala Thr Tyr Pro Glu Ser Phe His Thr
                405                 410                 415

Leu Glu Ser Val Pro Ala Thr Gly Arg Ser Ser Gln Val Tyr Phe Thr
            420                 425                 430

Ile Asn Val Asn Leu Asp Leu Ser Glu Ala Ala Val Val Thr Phe Ser
        435                 440                 445

Lys Pro Leu Arg Arg Asn Asn Ser Tyr Thr Ser Tyr Ile Met Ala Ile
```

```
    450                 455                 460

Cys Gly Met Pro Leu Asp Ser Phe Arg Thr Thr Cys Leu Ala Val Gly
465                 470                 475                 480

Gly Leu Asp Val Lys Phe Gln Glu Ala Ala Leu Arg Ala Ala Pro Asp
                485                 490                 495

Ile Leu Ile Tyr Glu Phe Asp Tyr His Leu Tyr Gly Gln Asn Ile Thr
            500                 505                 510

Met Ile Met Thr Ser Val Ser Gly His Leu Leu Pro Asp Ser Phe Ser
        515                 520                 525

Ile Pro Tyr Leu Thr Ala Leu Asp Asp Leu Leu Gly Thr Ala Leu Leu
    530                 535                 540

Ala Leu Ser Phe Tyr Ala Thr Ile Leu Glu Met Gln Ala Met Met Thr
545                 550                 555                 560

Leu Asp Pro Gln Asp Ile Leu Leu Ala Gly Asn Met Met Ser Trp Ile
                565                 570                 575

His Cys Trp Lys Tyr Leu Ser Val Gln Ser Gln Leu Phe Arg Gly Ser
            580                 585                 590

Ser Leu Leu Phe Arg Arg Tyr Asp Asn Lys Gly Ile Thr Tyr Leu Phe
        595                 600                 605

Asp Leu Tyr Tyr Glu Ser Asp Glu Phe Thr Val Asp Ala Ala Arg Ala
    610                 615                 620

Gln Ala Ala Lys Asn Lys Gly Asn Lys Tyr Phe Gln Ala Gly Lys Tyr
625                 630                 635                 640

Glu Gln Ala Ile Gln Cys Tyr Thr Gln Pro Met Leu Pro Ile Gly Leu
                645                 650                 655

Ser Asp Ile Pro Asp Glu Ala Met Val Lys Leu Tyr Cys Pro Lys Cys
            660                 665                 670

Met His Arg Gly Ala Ile Tyr Gly Ser Ser Trp Lys Tyr Phe Thr Phe
        675                 680                 685

Ser Gly Tyr Leu Leu Tyr Gln Asp Val Ile Gln Thr Ser Lys Tyr Tyr
    690                 695                 700

Met Arg Asp Val Ile Ala Ile Glu Ser Ala Trp Leu Leu Glu Leu Ala
705                 710                 715                 720

Pro Pro Arg Gly Val Asp Leu Tyr Leu Arg Ile Leu Met Pro Ile Asp
                725                 730                 735

Ser Glu Leu Val Asp Arg Asp Val Val His Gln Ile Glu Gln Asp Ala
            740                 745                 750

Leu Cys Pro Gln Asp Thr Tyr Cys Asp Leu Lys Ser Arg Ala Glu Val
        755                 760                 765

Asn Gly Ala Ala Leu Ala Ser Ala Ile Leu Ser Asp Pro Glu Ser Tyr
    770                 775                 780

Ile Lys Lys Leu Lys Glu Leu Arg Ser Met Leu Met Val Ile Val Leu
785                 790                 795                 800

Asp Ser Ser Gln Gly Asn Ser Val Cys Gln Ile Ala Met Val His Tyr
                805                 810                 815

Ile Lys Gln Lys Tyr Gly Tyr Pro Tyr Asp Val Pro Asp Tyr Ala Ser
            820                 825                 830


<210> SEQ ID NO 172
<211> LENGTH: 790
<212> TYPE: PRT
<213> ORGANISM: Artificial Sequence
<220> FEATURE:
<223> OTHER INFORMATION: GAd-CT26-1-31 polyneoantigen
```

<400> SEQUENCE: 172

Met Asp Ala Met Lys Arg Gly Leu Cys Cys Val Leu Leu Leu Cys Gly
1 5 10 15

Ala Val Phe Val Ser Pro Ser Gln Glu Ile His Ala Arg Met Lys Ser
20 25 30

Val Ser Ile Gln Tyr Leu Glu Ala Val Lys Arg Leu Lys Ser Glu Gly
35 40 45

His Arg Phe Pro Arg Thr Lys Gly Gly Pro Val Lys Ile Asp Pro Leu
50 55 60

Ala Leu Met Gln Ala Ile Glu Arg Tyr Leu Val Val Arg Gly Tyr Leu
65 70 75 80

Gln Asp Asp Pro Asp Leu Gln Ala Leu Leu Lys Ala Ser Gln Leu Leu
85 90 95

Lys Val Lys Ser Ser Ser Trp Arg Leu Ile Ala His Met Ile Leu Gly
100 105 110

Tyr Arg Tyr Trp Thr Gly Ile Gly Val Leu Gln Ser Cys Glu Ser Ala
115 120 125

Leu Thr Ser Val Asp Gln His Leu Ala Pro Gly Ala Val Ala Met Pro
130 135 140

Gln Ala Ala Ser Leu His Ala Val Ile Val Glu Ile Ser Val Arg Ile
145 150 155 160

Ala Thr Ile Pro Ala Phe Asp Thr Ile Met Glu Thr Val Ile Gln Arg
165 170 175

Glu Leu Leu Lys Thr Ser Arg Glu Ile Lys Ile Ser Gly Ala Ile Glu
180 185 190

Pro Cys Val Ser Leu Asn Ser Lys Gly Pro Cys Val Gln Gly Leu Ala
195 200 205

Asn Tyr Val Ile Thr Thr Met Gly Thr Ile Cys Ala Pro Val Arg Asp
210 215 220

Glu Asp Ile Arg Glu Glu Leu Ser Arg Arg Gln Tyr Ala Glu Gln Glu
225 230 235 240

Leu Lys Gln Val Arg Met Ala Leu Lys Lys Ala Glu Lys Glu Ile Glu
245 250 255

Thr Gln Gln Arg Lys Phe Lys Ala Ser Arg Ala Ser Ile Leu Ser Glu
260 265 270

Met Lys Met Leu Lys Glu Lys Ser Ile Phe Leu Asp Asp Asp Ser Asn
275 280 285

Gln Pro Met Ala Val Ser Arg Phe Phe Gly Asn Val Glu Leu Met Gln
290 295 300

Arg Pro Asp Ser Tyr Val Arg Asp Met Glu Ile Glu Ala Ala Ser His
305 310 315 320

His Val Tyr Ala Asp Gln Pro His Ile Thr Leu Ser Ala Met Ser Asn
325 330 335

Pro Arg Ala Met Gln Val Leu Leu Gln Ile Gln Gln Gly Leu Gln Thr
340 345 350

Leu Ala Val Met Lys Gly Thr Leu Glu Tyr Leu Met Ser Asn Thr Pro
355 360 365

Thr Ala Gln Ser Leu Arg Glu Ser Tyr Ile Phe Ala Ala Glu Leu Phe
370 375 380

His Gln Leu Ser Gln Ala Leu Lys Val Leu Thr Asp Ala Ala Ala Arg
385 390 395 400

Ala Ala Tyr Asp Thr Gly Leu Tyr Phe Arg Lys Ser Tyr Tyr Met Gln
405 410 415

Lys Tyr Phe Leu Asp Thr Val Thr Glu Asp Ala Lys Val Cys Arg Asn
420 425 430

Asn Val His Tyr Leu Asn Asp Gly Asp Ala Ile Ile Tyr His Thr Ala
435 440 445

Ser Ile Gly Ile Leu His Asp Ile Asn Asp Asn Asn Pro Ser Phe Pro
450 455 460

Thr Gly Lys Met Lys Leu Glu Ile Ser Glu Ala Leu Ala Pro Gly Arg
465 470 475 480

Glu Gly Ile Leu Gln Glu Glu Ser Ile Tyr Lys Pro Gln Lys Gln Glu
485 490 495

Gln Glu Leu Arg Ala Leu Gln Ala Ile Asn Pro Thr Met Ile Ile Ser
500 505 510

Asn Thr Leu Ser Lys Ser Ala Ile Ala Thr Pro Lys Ile Ser Tyr Leu
515 520 525

Leu Gln Asp Leu His Asn Leu Asn Leu Leu Ser Leu Tyr Ala Asn Lys
530 535 540

Leu Gln Thr Val Ala Lys Gly Thr Phe Ser Gln Glu Ile Gln Thr Tyr
545 550 555 560

Ala Ile Ala Leu Ile Asn Val Leu Phe Leu Lys Ala Pro Glu Asp Lys
565 570 575

Arg Gln Asp Cys Tyr Asn Tyr Leu Tyr Arg Met Lys Ala Leu Asp Gly
580 585 590

Ile Arg Ala Ser Glu Ile Pro Phe His Ala Glu Gly Gln Ser Ile His
595 600 605

Ser Phe Gln Ser Leu Glu Glu Ser Ile Ser Val Leu Pro Ser Phe Gln
610 615 620

Glu Pro His Leu Gln Thr Asp Phe Cys Leu Arg Asn Leu Asp Gly Thr
625 630 635 640

Leu Cys Tyr Leu Leu Asp Lys Glu Thr Leu Arg Leu His Pro Cys Glu
645 650 655

Val Thr Arg Val Lys Ala Val Arg Ile Leu Pro Cys Gly Val Ala Lys
660 665 670

Val Leu Trp Met Gln Gly Ser Gly Tyr Asp Ser Arg Ser Ala Arg Ala
675 680 685

Phe Pro Tyr Ala Asn Val Ala Phe Pro His Leu Thr Ser Ser Ala Pro
690 695 700

Thr Asp Lys Glu Leu Arg Glu Ala Met Ala Leu Leu Ala Ala Gln Gln
705 710 715 720

Thr Ala Leu Glu Val Ile Val Asn Met Leu Ser Arg Pro Asp Leu Pro
725 730 735

Phe Leu Ile Ala Ala Val Phe Phe Leu Val Val Ala Val Trp Gly Glu
740 745 750

Thr Leu Leu Tyr Tyr Thr Thr Val Arg Ala Leu Thr Arg His Asn Thr
755 760 765

Met Leu Lys Ala Met Phe Ser Gly Arg Met Glu Gly Tyr Pro Tyr Asp
770 775 780

Val Pro Asp Tyr Ala Ser
785 790

<210> SEQ ID NO 173
<211> LENGTH: 281
<212> TYPE: PRT
<213> ORGANISM: Homo sapiens

<400> SEQUENCE: 173

```
Met Ala Asp Ser Ala Glu Asp Ala Pro Met Ala Arg Gly Ser Leu Ala
1               5                   10                  15

Gly Ser Asp Glu Ala Leu Ile Leu Pro Ala Gly Pro Thr Gly Gly Ser
            20                  25                  30

Asn Ser Arg Ala Leu Lys Val Ala Gly Leu Thr Thr Leu Thr Cys Leu
        35                  40                  45

Leu Leu Ala Ser Gln Val Phe Thr Ala Tyr Met Val Phe Gly Gln Lys
    50                  55                  60

Glu Gln Ile His Thr Leu Gln Lys Asn Ser Glu Arg Met Ser Lys Gln
65                  70                  75                  80

Leu Thr Arg Ser Ser Gln Ala Val Ala Pro Met Lys Met His Met Pro
                85                  90                  95

Met Asn Ser Leu Pro Leu Leu Met Asp Phe Thr Pro Asn Glu Asp Ser
            100                 105                 110

Lys Thr Pro Leu Thr Lys Leu Gln Asp Thr Ala Val Val Ser Val Glu
        115                 120                 125

Lys Gln Leu Lys Asp Leu Met Gln Asp Ser Gln Leu Pro Gln Phe Asn
    130                 135                 140

Glu Thr Phe Leu Ala Asn Leu Gln Gly Leu Lys Gln Gln Met Asn Glu
145                 150                 155                 160

Ser Glu Trp Lys Ser Phe Glu Ser Trp Met Arg Tyr Trp Leu Ile Phe
                165                 170                 175

Gln Met Ala Gln Gln Lys Pro Val Pro Pro Thr Ala Asp Pro Ala Ser
            180                 185                 190

Leu Ile Lys Thr Lys Cys Gln Met Glu Ser Ala Pro Gly Val Ser Lys
        195                 200                 205

Ile Gly Ser Tyr Lys Pro Gln Cys Asp Glu Gln Gly Arg Tyr Lys Pro
    210                 215                 220

Met Gln Cys Trp His Ala Thr Gly Phe Cys Trp Cys Val Asp Glu Thr
225                 230                 235                 240

Gly Ala Val Ile Glu Gly Thr Thr Met Arg Gly Arg Pro Asp Cys Gln
                245                 250                 255

Arg Arg Ala Leu Ala Pro Arg Arg Met Ala Phe Ala Pro Ser Leu Met
            260                 265                 270

Gln Lys Thr Ile Ser Ile Asp Asp Gln
        275                 280
```

<210> SEQ ID NO 174
<211> LENGTH: 281
<212> TYPE: PRT
<213> ORGANISM: Sinipera chuatsi

<400> SEQUENCE: 174

```
Met Ala Asp Ser Ala Glu Asp Ala Pro Met Ala Arg Gly Ser Leu Ala
1               5                   10                  15

Gly Ser Asp Glu Ala Leu Ile Leu Pro Ala Gly Pro Thr Gly Gly Ser
            20                  25                  30

Asn Ser Arg Ala Leu Lys Val Ala Gly Leu Thr Thr Leu Thr Cys Leu
        35                  40                  45

Leu Leu Ala Ser Gln Val Phe Thr Ala Tyr Met Val Phe Gly Gln Lys
    50                  55                  60

Glu Gln Ile His Thr Leu Gln Lys Asn Ser Glu Arg Met Ser Lys Gln
65                  70                  75                  80
```

```
Leu Thr Arg Ser Ser Gln Ala Val Ala Pro Met Lys Met His Met Pro
                85                  90                  95

Met Asn Ser Leu Pro Leu Leu Met Asp Phe Thr Pro Asn Glu Asp Ser
            100                 105                 110

Lys Thr Pro Leu Thr Lys Leu Gln Asp Thr Ala Val Val Ser Val Glu
        115                 120                 125

Lys Gln Leu Lys Asp Leu Met Gln Asp Ser Gln Leu Pro Gln Phe Asn
    130                 135                 140

Glu Thr Phe Leu Ala Asn Leu Gln Gly Leu Lys Gln Gln Met Asn Glu
145                 150                 155                 160

Ser Glu Trp Lys Ser Phe Glu Ser Trp Met Arg Tyr Trp Leu Ile Phe
                165                 170                 175

Gln Met Ala Gln Gln Lys Pro Val Pro Pro Thr Ala Asp Pro Ala Ser
            180                 185                 190

Leu Ile Lys Thr Lys Cys Gln Met Glu Ser Ala Pro Gly Val Ser Lys
        195                 200                 205

Ile Gly Ser Tyr Lys Pro Gln Cys Asp Glu Gln Gly Arg Tyr Lys Pro
    210                 215                 220

Met Gln Cys Trp His Ala Thr Gly Phe Cys Trp Cys Val Asp Glu Thr
225                 230                 235                 240

Gly Ala Val Ile Glu Gly Thr Thr Met Arg Gly Arg Pro Asp Cys Gln
                245                 250                 255

Arg Arg Ala Leu Ala Pro Arg Arg Met Ala Phe Ala Pro Ser Leu Met
            260                 265                 270

Gln Lys Thr Ile Ser Ile Asp Asp Gln
        275                 280


<210> SEQ ID NO 175
<211> LENGTH: 27
<212> TYPE: PRT
<213> ORGANISM: Sinipera chuatsi

<400> SEQUENCE: 175

Gly Gln Lys Glu Gln Ile His Thr Leu Gln Lys Asn Ser Glu Arg Met
1               5                   10                  15

Ser Lys Gln Leu Thr Arg Ser Ser Gln Ala Val
            20                  25


<210> SEQ ID NO 176
<211> LENGTH: 16
<212> TYPE: PRT
<213> ORGANISM: Sinipera chuatsi

<400> SEQUENCE: 176

Gln Ile His Thr Leu Gln Lys Asn Ser Glu Arg Met Ser Lys Gln Leu
1               5                   10                  15


<210> SEQ ID NO 177
<211> LENGTH: 187
<212> TYPE: PRT
<213> ORGANISM: Paralichthys olivaceus

<400> SEQUENCE: 177

Met Ser Glu Thr Gln Thr Leu Leu Gly Ala Pro Arg Gln Gln Thr Ala
1               5                   10                  15

Val Asp Val Gly Ala Pro Ala Gln Gly Gly Arg Ser Ala Asn Ala Tyr
            20                  25                  30

Lys Val Val Gly Leu Thr Val Leu Ala Cys Val Leu Val Met Ser Gln
```

```
        35                  40                  45

Ala Met Ile Ile Tyr Phe Leu Val Asn Gln Arg Gly Asp Ile Lys Ser
    50                  55                  60

Leu Glu Glu Gln His Ser Gly Leu Asn Glu Gln Leu Thr Lys Gly Arg
65                  70                  75                  80

Ser Ala Ser Met Ser Met Gln Leu Pro Ser Ser Phe His Ser Leu Thr
                85                  90                  95

Phe Asp Glu Lys Ser Ser Thr Arg Ala Pro Glu Glu Thr Gly Pro Pro
            100                 105                 110

Gln Ala Thr Gln Cys Gln Leu Glu Ala Ala Gly Glu Lys Pro Val Gln
        115                 120                 125

Val Pro Gly Leu Arg Pro Asp Cys Asp Glu Arg Gly Leu Tyr Arg Leu
    130                 135                 140

Lys Gln Cys Leu Lys His Arg Cys Trp Cys Val Asn Pro Ala Asn Gly
145                 150                 155                 160

Glu Gln Ile Pro Gly Ser Leu Gly Lys Glu Asp Val Thr Cys Asn Lys
                165                 170                 175

Gly Val His Ser Val Gly Leu Asp Lys Val Leu
            180                 185


<210> SEQ ID NO 178
<211> LENGTH: 27
<212> TYPE: PRT
<213> ORGANISM: Paralichthys olivaceus

<400> SEQUENCE: 178

Asn Gln Arg Gly Asp Ile Lys Ser Leu Glu Glu Gln His Ser Gly Leu
1               5                   10                  15

Asn Glu Gln Leu Thr Lys Gly Arg Ser Ala Ser
            20                  25


<210> SEQ ID NO 179
<211> LENGTH: 16
<212> TYPE: PRT
<213> ORGANISM: Paralichthys olivaceus

<400> SEQUENCE: 179

Asp Ile Lys Ser Leu Glu Glu Gln His Ser Gly Leu Asn Glu Gln Leu
1               5                   10                  15


<210> SEQ ID NO 180
<211> LENGTH: 197
<212> TYPE: PRT
<213> ORGANISM: Boleophthalmus pectiniros

<400> SEQUENCE: 180

Met Glu His Ala Ser Glu Asp Ala Pro Leu Ala Arg Asp Ser Gly Thr
1               5                   10                  15

Gly Ser Glu Gln Ala Leu Val Val Pro Thr Ala Pro Arg Arg Gly Ser
            20                  25                  30

Asn Ser His Ala Val Lys Ile Ala Gly Ile Thr Thr Leu Val Cys Leu
        35                  40                  45

Leu Val Ser Ala Gln Val Phe Thr Ala Tyr Met Val Phe Asp Gln Lys
    50                  55                  60

Gln Gln Ile Gln Gly Leu Gln Thr Ser Asn Gln Arg Leu Glu Lys Gln
65                  70                  75                  80

Met Gly Gln Arg Pro Arg Glu Ser Leu Lys Lys Ile Val Met Pro Ala
                85                  90                  95
```

-continued

Asn Ser Met Pro Ile Leu Asp Phe Phe Asp Asp Gly Lys Ser Pro Gln
100 105 110

Asn Ser Pro Lys Ala Glu Pro Pro Lys Gln Asp Val Ala Pro Pro Ser
115 120 125

Val Glu Lys Gln Leu Gln Glu Leu Met Lys Val Phe Thr Asp Phe Pro
130 135 140

Gln Met Asn Glu Ser Phe Leu Ala Asn Leu Gln Thr Met Lys Gln Lys
145 150 155 160

Val Ser Glu Thr Asp Trp Lys Ser Phe Glu Ala Trp Met His Tyr Trp
165 170 175

Leu Ile Phe Gln Met Ala Gln Lys Thr Ser Thr Pro Thr Pro Gln Pro
180 185 190

Asp Gly Gly Ser Lys
195

<210> SEQ ID NO 181
<211> LENGTH: 27
<212> TYPE: PRT
<213> ORGANISM: Boleophthalmus pectiniros

<400> SEQUENCE: 181

Asp Gln Lys Gln Gln Ile Gln Gly Leu Gln Thr Ser Asn Gln Arg Leu
1 5 10 15

Glu Lys Gln Met Gly Gln Arg Pro Arg Glu Ser
20 25

<210> SEQ ID NO 182
<211> LENGTH: 16
<212> TYPE: PRT
<213> ORGANISM: Boleophthalmus pectiniros

<400> SEQUENCE: 182

Gln Ile Gln Gly Leu Gln Thr Ser Asn Gln Arg Leu Glu Lys Gln Met
1 5 10 15

<210> SEQ ID NO 183
<211> LENGTH: 11
<212> TYPE: PRT
<213> ORGANISM: Influenza A virus

<400> SEQUENCE: 183

Gly Tyr Pro Tyr Asp Val Pro Asp Tyr Ala Ser
1 5 10

<210> SEQ ID NO 184
<211> LENGTH: 24
<212> TYPE: PRT
<213> ORGANISM: Aphthovirus A

<400> SEQUENCE: 184

Ala Pro Val Lys Gln Thr Leu Asn Phe Asp Leu Leu Lys Leu Ala Gly
1 5 10 15

Asp Val Glu Ser Asn Pro Gly Pro
20